United States Patent
Nakamura et al.

(10) Patent No.: US 9,587,271 B2
(45) Date of Patent: *Mar. 7, 2017

(54) MIXTURES FOR ASSAYING NUCLEIC ACID, NOVEL METHOD OF ASSAYING NUCLEIC ACID WITH THE USE OF THE SAME AND NUCLEIC ACID PROBE TO BE USED THEREFOR

(71) Applicant: NIPPON STEEL & SUMIKIN ECO-TECH CORPORATION, Tokyo (JP)

(72) Inventors: Kazunori Nakamura, Tsukuba (JP); Takahiro Kanagawa, Tsukuba (JP); Naohiro Noda, Tsukuba (JP); Satoshi Tsuneda, Tokyo (JP); Hidenori Tani, Tokyo (JP); Shinya Kurata, Tokyo (JP)

(73) Assignee: NIPPON STEEL & SUMIKIN ECO-TECH CORPORATION, Tokyo (JP)

( * ) Notice: Subject to any disclaimer, the term of this patent is extended or adjusted under 35 U.S.C. 154(b) by 748 days.

This patent is subject to a terminal disclaimer.

(21) Appl. No.: 13/665,566

(22) Filed: Oct. 31, 2012

(65) Prior Publication Data
US 2013/0065237 A1    Mar. 14, 2013

Related U.S. Application Data

(60) Division of application No. 13/089,420, filed on Apr. 19, 2011, now abandoned, which is a continuation of (Continued)

(30) Foreign Application Priority Data

Dec. 19, 2003   (JP) .................................. 2003-423774

(51) Int. Cl.
  *C12Q 1/68*    (2006.01)
(52) U.S. Cl.
  CPC ... *C12Q 1/6818* (2013.01); *Y10T 436/143333* (2015.01)

(58) Field of Classification Search
  None
  See application file for complete search history.

(56) References Cited

U.S. PATENT DOCUMENTS

| | | |
|---|---|---|
| 5,219,727 A | 6/1993 | Wang et al. |
| 5,476,774 A | 12/1995 | Wang et al. |

(Continued)

FOREIGN PATENT DOCUMENTS

| | | |
|---|---|---|
| JP | 7-250700 | 10/1995 |
| JP | 2619866 | 3/1997 |

(Continued)

OTHER PUBLICATIONS

Wittwer et al. Real-time multiplex PCR assays. Methods 25:430-442 (2001).*

(Continued)

*Primary Examiner* — Samuel Woolwine
(74) *Attorney, Agent, or Firm* — Oblon, McClelland, Maier & Neustadt, L.L.P.

(57) ABSTRACT

[Problems] To provide a novel mixture for assaying a target nucleic acid, characterized by enabling a nucleic acid assay while: 1) requiring no step of diluting the target nucleic acid; 2) requiring no procedure of changing a probe concentration depending on a concentration of the target nucleic acid.
[Means for Solving Problems] 1) A mixture which comprises one internal standard nucleic acid and two nucleic acid probes labeled with a fluorescent dye; 2) a mixture for measuring Km value which comprises one internal standard nucleic acid having a partial mutation and one nucleic acid probe labeled with a fluorescent dye; 3) a mixture which comprises one internal standard nucleic acid and one double nucleic acid probe labeled with two fluorescent dyes; and a method for assaying a nucleic acid by making use thereof.

15 Claims, 20 Drawing Sheets

Related U.S. Application Data application No. 12/540,390, filed on Aug. 13, 2009, now Pat. No. 7,951,604, which is a division of application No. 10/583,457, filed as application No. PCT/JP2004/019047 on Dec. 20, 2004, now abandoned.

(56) References Cited

U.S. PATENT DOCUMENTS

| | | | |
|---|---|---|---|
| 5,928,862 | A | 7/1999 | Morrison |
| 6,022,686 | A | 2/2000 | Garman et al. |
| 6,492,121 | B2 | 12/2002 | Kurane et al. |
| 6,495,326 | B2 | 12/2002 | Kurane et al. |
| 6,699,661 | B1 | 3/2004 | Kurane et al. |
| 2003/0082592 | A1 | 5/2003 | Kurane et al. |
| 2003/0104438 | A1 | 6/2003 | Eyre et al. |
| 2003/0165859 | A1 | 9/2003 | Nazarenko et al. |
| 2003/0175728 | A1 | 9/2003 | Belousov et al. |
| 2003/0219823 | A1 | 11/2003 | Alsobrook et al. |
| 2003/0219852 | A1 | 11/2003 | Bank et al. |
| 2004/0063137 | A1 | 4/2004 | Kurane et al. |
| 2004/0166511 | A1 | 8/2004 | Clasina Timmermans et al. |
| 2006/0172293 | A1 | 8/2006 | Kurata et al. |
| 2009/0233308 | A1 | 9/2009 | Kurata et al. |
| 2011/0212442 | A1 | 9/2011 | Sekiguchi et al. |

FOREIGN PATENT DOCUMENTS

| | | |
|---|---|---|
| JP | 10-262700 | 10/1998 |
| JP | 2003-180378 | 7/2003 |
| WO | 02063049 | 8/2002 |
| WO | 03/089669 | 10/2003 |
| WO | 2004/033726 | 4/2004 |

OTHER PUBLICATIONS

Applied Biosystems Standard Dye Sets for Genotyping Applications [online][retrieved on Mar. 26, 2015] retrieved from http://www.uri.edu/research/gsc/docs/ABI%20Dye%20Set%20card.pdf.*

Torimura et al. Fluorescence-quenching phenomenon by photoinduced electron transfer between a fluorescent dya and a nucleotide base. Analytical Sciences 17:155-160 (2001).*

Sauer et al. New fluorescent dyes in the red region for biodiagnostics. Journal of Fluorescence 5(3):247-261 (1995).*

Kurata, Shinya et al., "Fluorescent quenching-based quantitative detection of specific DNA/RNA using a BODIPY® FL-labeled probe or primer", Nucleic Acids Research, vol. 29, No. 6, pp. 1-5, 2001.

Andrew O. Crockett, et al., "Fluorescein-Labeled Oligonucleotides for Real-Time PCR: Using the Inherent Quenching of Deoxyguanosine Nucleotides", Analytical Biochemistry, Mar. 1, 2001, vol. 290, No. 1, pp. 89-97.

B. Terouanne, et al., "Quantitative and Qualitative Analysis of Amplified DNA Sequences by a Competitive Hybridization Assay", Analytical Biochemistry, Sep. 1992, vol. 205, No. 2, pp. 193-199.

GenBank GI:211581525 [online] Nov. 1, 2008 [retrieved on Apr. 8, 2009] retrieved from http://www.ncbi.nlm.nih.gov/nuccore/211581525 (1st page only).

Chen et al., A homogeneous, ligase-medicated DNA diagnostic test. Genome Research 8:549-556 (1998).

Tremmel et al. High-resolution typing for HLA-DRB1*15 and -DRB1*16 by fluorescence-marked sequence-specific priming (TaqMan assay). Tissue Antigens 54:508-516 (1999).

Gen Bank GI:5174458 [online] Jun. 24, 1999 [retrieved on Apr. 8, 2009] retrieved from: (http://www.ncbi.nlm.nih.gov/entrez/viewer.fcgi?5174458:OLD02:500876.

GenBank GI:170522971 [online] Mar. 25, 2008 [retrieved on Apr. 8, 2009] retrieved from: http://www.ncbi.nlm.nih.gov/nuccore/170522971.

GenBank GI:223462484 [online] Feb. 11, 2009 [retrieved on Apr. 8, 2009] retrieved from http://www.ncbi.nlm.nih.gov/nuccore/223462484.

Lyttle et al., New reagents and methods for the synthesis of internal and 3'-labeled DNA. Bioconjugate Chemistry 13:1146-1154 (2002).

Inazuka, et al. Analysis of p53 tumour suppressor gene somatic mutations in rheumatoid arthritis synovium. Rheumatology 39:262-266 (2000).

Marras et al. Efficiencies of fluorescence resonance energy transfer and contact-mediated quenching in oligonucleotide probes. Nucleic Acids Research 30 (21) e122 (2002).

* cited by examiner

FIG. 1
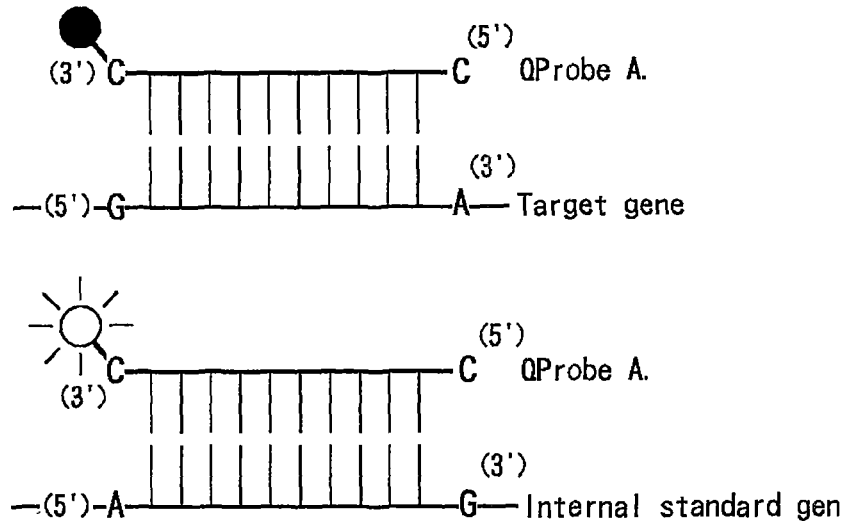
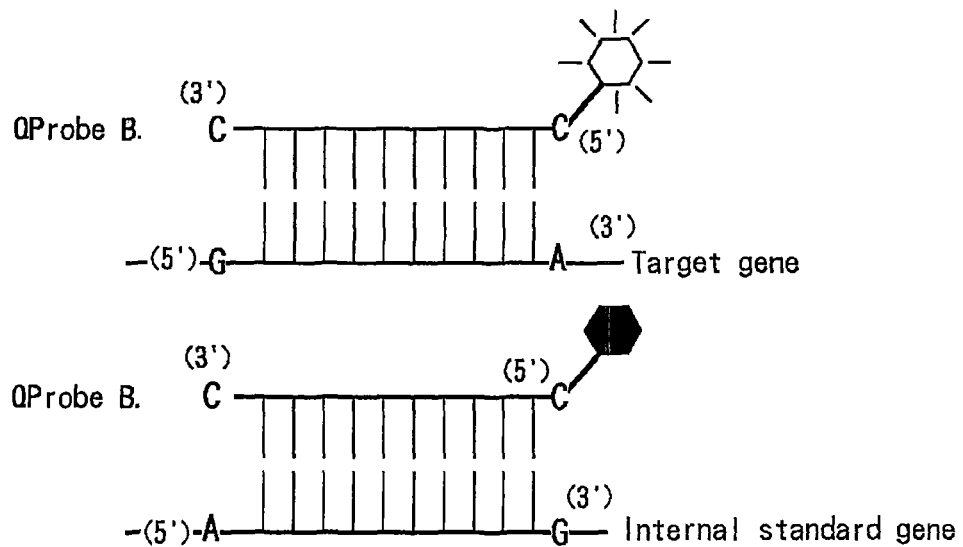

FIG. 3

<In use of two QProbes>

In use of a QProbes for detecting a target gene

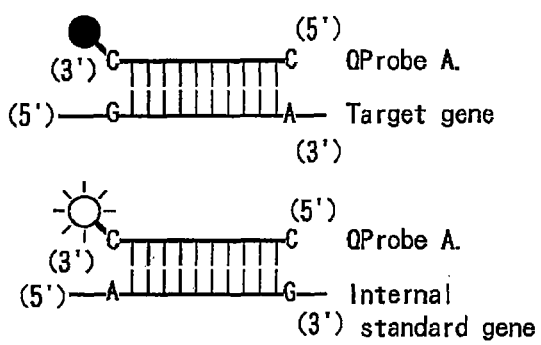

- Hybridization with an Internal standard gene results in no fluorescence-quenching.

In use of a QProbe for detecting an internal standard gene

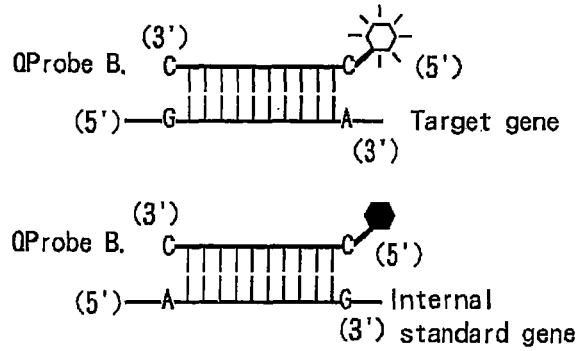

- Hybridization with a target gene results in no fluorescence-quenching.

<In use of Switching QProbe>

Structure of Switching Probe

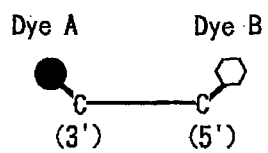

- Both end bases are cytosines
- Both ends are labeled with different dyes respectively

In hybridization with a target gene

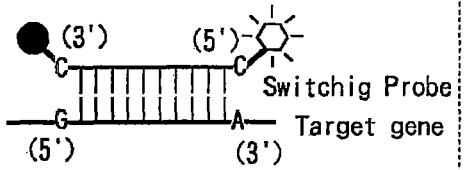

In hybridization with an Internal standard gene

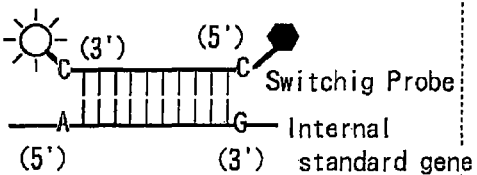

- Hybridization with either of genes results in fluorescence-quenching of dye labeling either of ends.

FIG. 13
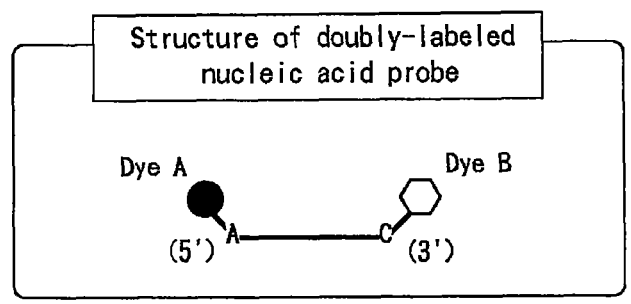
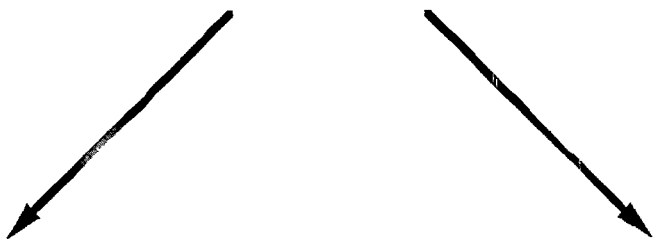
A. Pattern indicating that fluorescence-quenching for dye A is caused with a target nucleic acid; that for dye B with any nucleic acid.
B. Pattern indicating that fluorescence-quenching for dye A is caused with an internal standard gene; that for dye B with any nucleic acid.
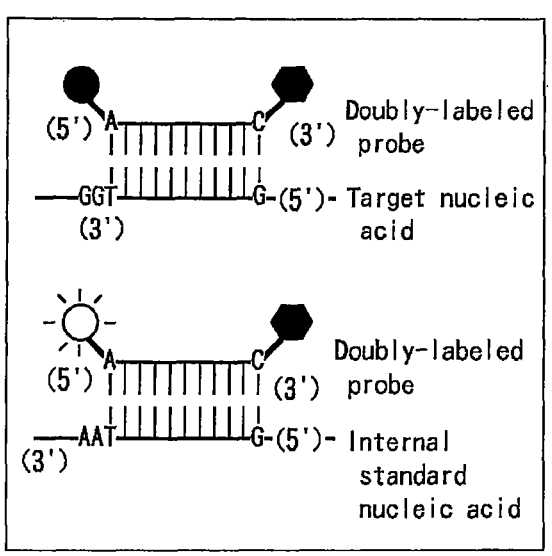
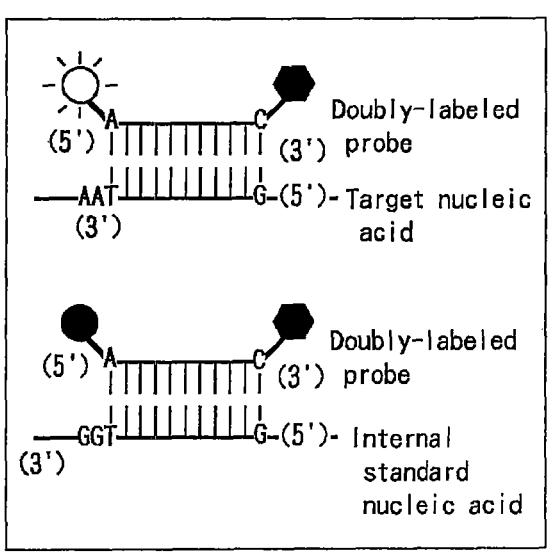

FIG. 15

A. Probe having two fluorescent changes

A. On hybridization with target nucleic acid

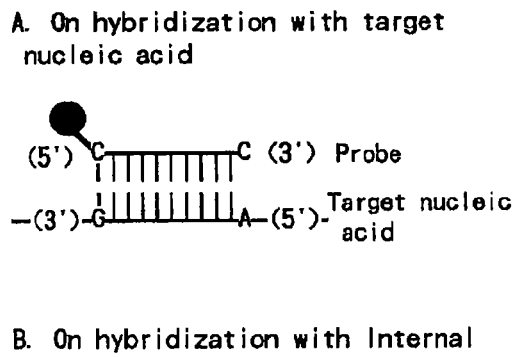

B. On hybridization with Internal standard nucleic acid

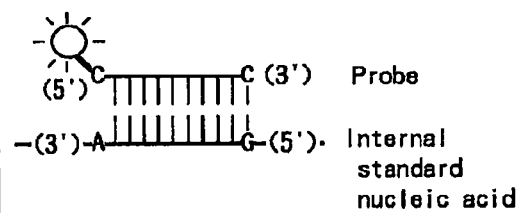

C. On no hybridization with any nucleic acid

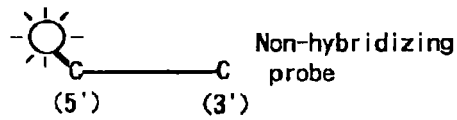

Fluorescent intensity for dye:
Internal standard nucleic acid=
non-hybridizing probe>target nucleic acid B. Probe having three fluorescent changes A. On hybridization with target nucleic acid

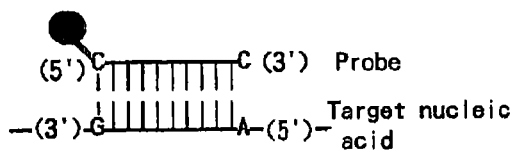

B. On hybridization with Internal standard nucleic acid

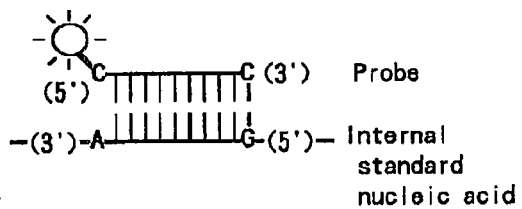

C. On no hybridization with any nucleic acid

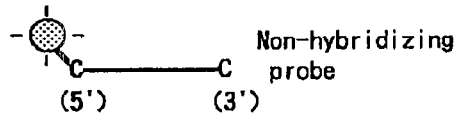

Fluorescent intensity for dye:
Internal standard nucleic acid>
non-hybridizing probe>target nucleic acid

FIG. 17
A. In no presence of fluorescent substance-labeled nucleic acid probe
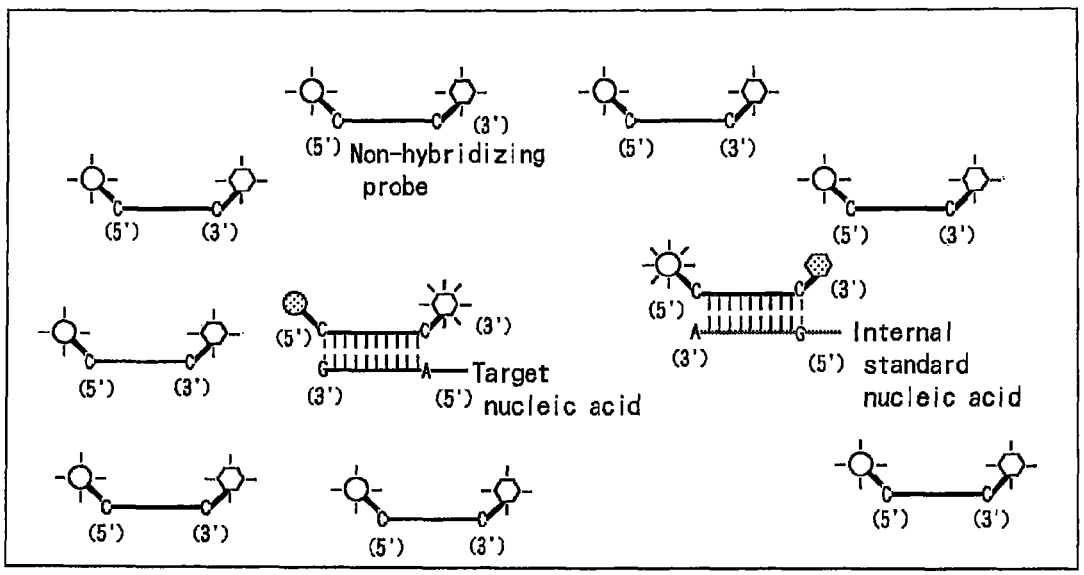
B. In presence of fluorescent substance-labeled nucleic acid probe
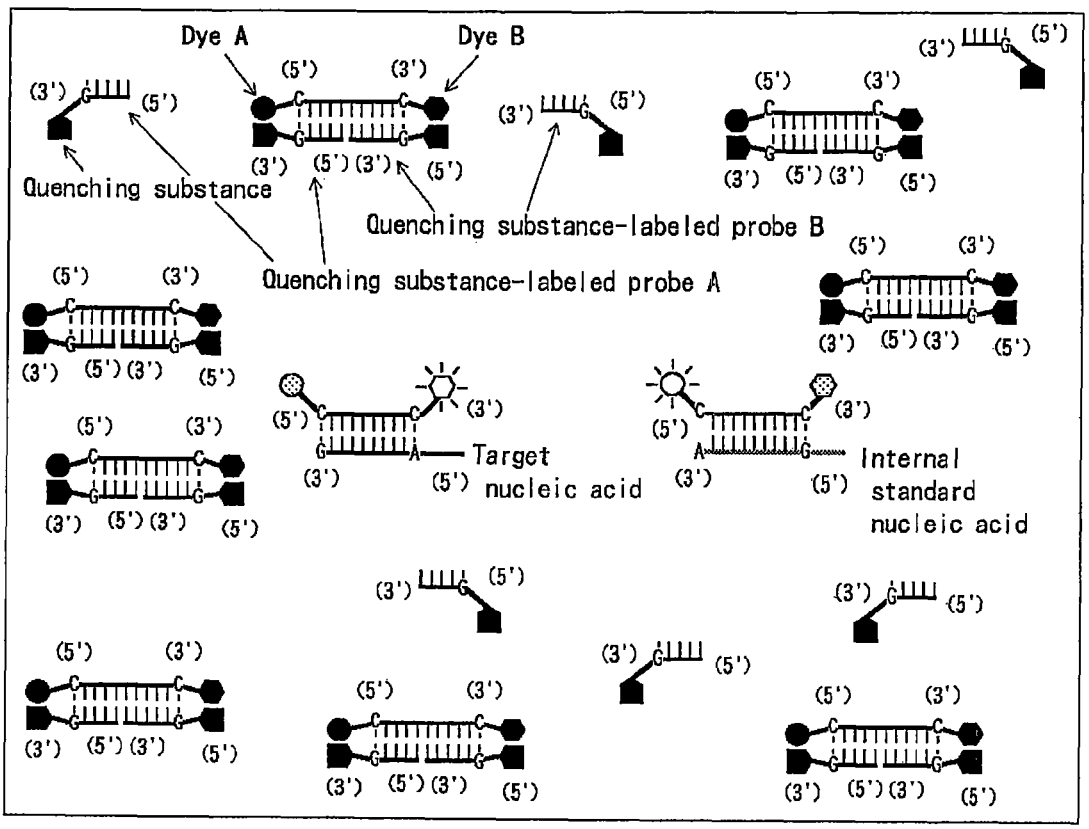

FIG. 18
A. In use of target nucleic acid probe
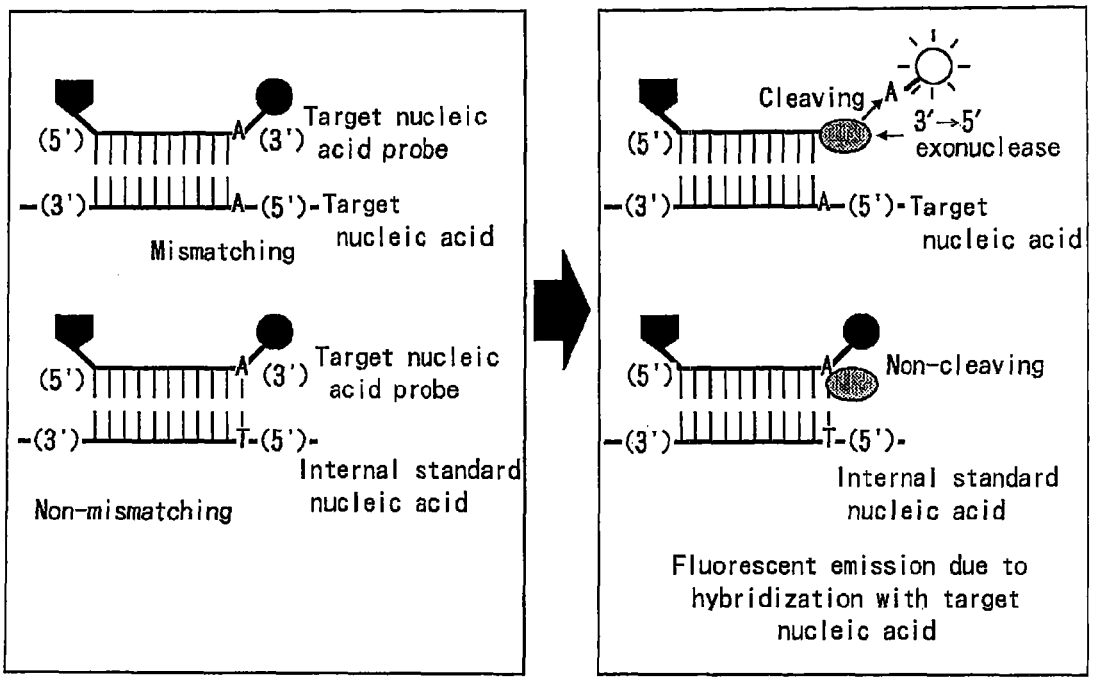
B. In use of Internal standard nucleic acid probe
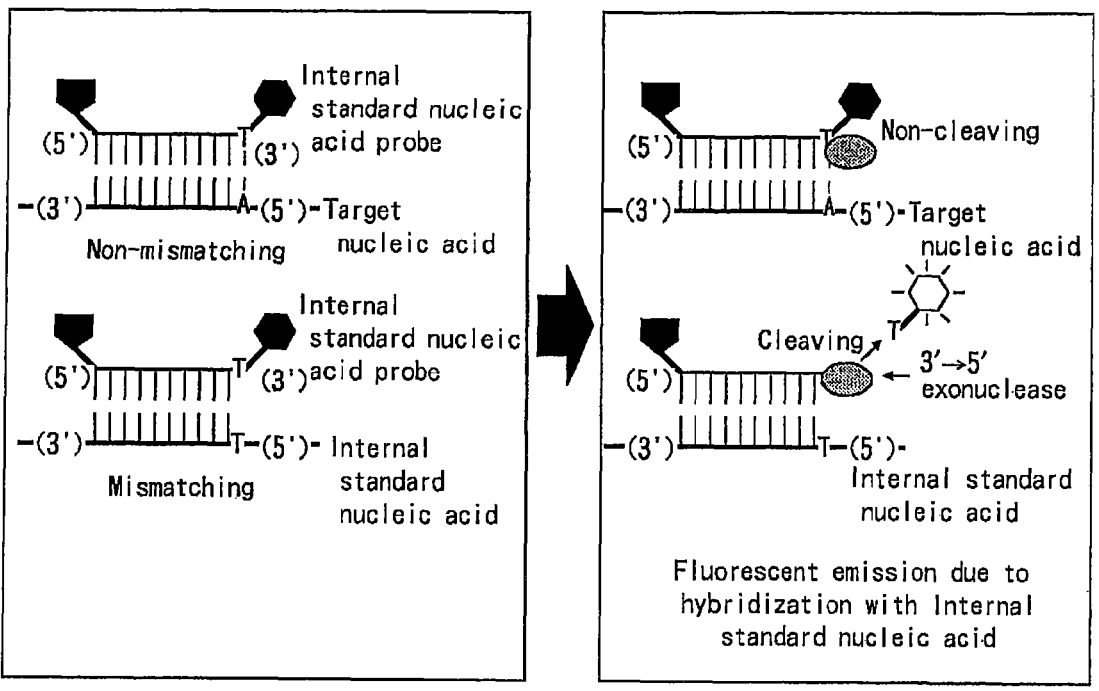

FIG. 20
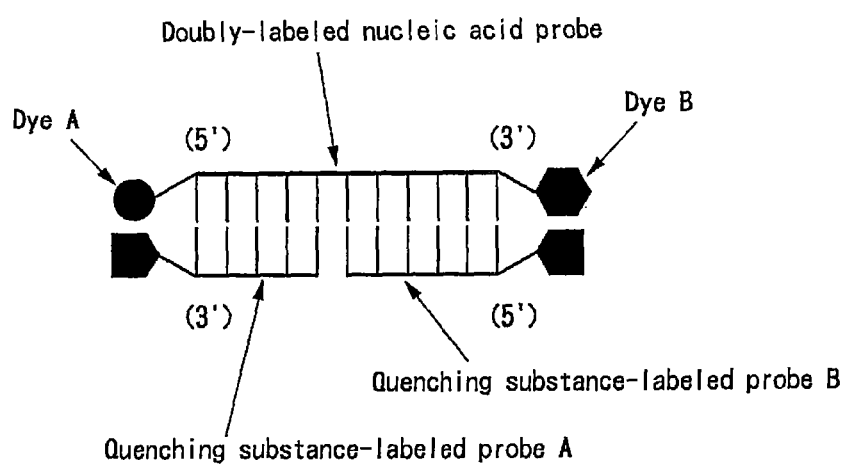
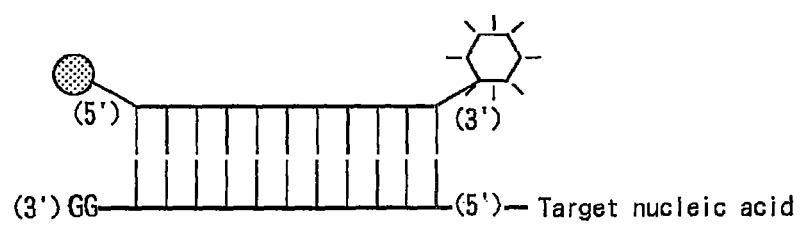
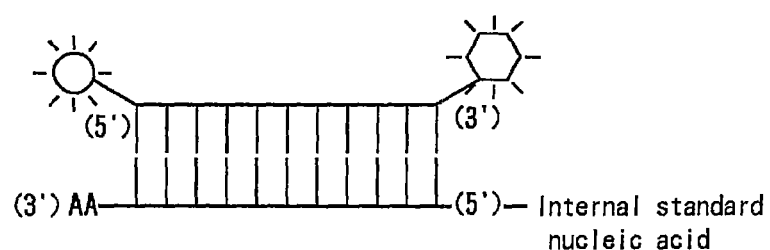

MIXTURES FOR ASSAYING NUCLEIC ACID, NOVEL METHOD OF ASSAYING NUCLEIC ACID WITH THE USE OF THE SAME AND NUCLEIC ACID PROBE TO BE USED THEREFOR

This application is a divisional of U.S. Ser. No. 13/089, 420 filed Apr. 19, 2011, abandoned, which is a continuation of U.S. Ser. No. 12/540,390 filed Aug. 13, 2009, now U.S. Pat. No. 7,951,604, which is a divisional of U.S. Ser. No. 10/583,457 filed Jun. 19, 2006, abandoned, which is a National Stage of PCT/JP04/19047 filed Dec. 20, 2004 and claims the benefit of JP 2003-423774 filed Dec. 19, 2003.

TECHNICAL FIELD

This invention relates to a novel mixture for assaying a nucleic acid, and specifically to a novel mixture for assaying'accurately, conveniently and non-expensively one or plural nucleic acids, and a method for assaying a nucleic acid using the same, and nucleic acid probes to be used for the assaying method and a nucleic acid-assaying kit.

BACKGROUND ART

Many examples of methods for assaying a target nucleic acid are methods for assaying a nucleic acid in a homogenous solution by using a fluorescent dye-labeled target nucleic acid probe having properties changing in fluorescence on hybridizing with a target nucleic acid (called a nucleic acid probe for a homogenous solution system or a target nucleic acid probe, having the same meaning). The method does not require, by this characteristics, 1) any step immobilizing a target nucleic acid (or any step washing a probe) indispensable for common hybridizing method and 2) any step washing out non-reacting probes (or any step immobilizing non-reacting genes); the method, therefore, is a method for assaying easily, rapidly and accurately a target nucleic acid. With such reasons, the method for assaying quantitatively a target nucleic acid has been in a wide used for various methods for analyzing genes (see non-patent reference 1).

In assaying directly a target nucleic acid by a nucleic acid probe for a homogenous solution system, an object could be achieved by using the following procedures.

(1) making a target nucleic acid of known concentrations ready beforehand hybridize with a nucleic acid probe for a homogenous solution system, and, on this hybridization, monitoring a change or the amount of change in an optical character;

(2) preparing a calculating curve for determining a target nucleic acid by preparing an equation relating to the above change or amount of change in an optical character and amounts of a target nucleic acid because the change or the amount of change is positively proportional to amounts of a target nucleic acid;

(3) conducting a procedures similar to the above procedures in regard to an unknown sample, and determining the amount of a target nucleic acid from the above calculating curve based on the obtained change or amount of change in an optical character.

In the method, however, if a target nucleic acid exists greater in concentration than an added nucleic acid probe, a change or the amount of a change in an optical character is at any time stationary. Because of this, the conventional methods need any of the means, 1) diluting a target nucleic acid sample, and 2) preparing in advance plural assaying systems with a probe having various concentrations. The above 1) requires a diluting processing step; the operation become complicated. As results, the above 2) has such problems that (1) long assaying time is needed; (2) diluting errors occur; and (3) on automation of the assaying, an for dilution is needed. In the above 2) also, the reaction time and reaction temperature suitable for hybridization vary with response to the concentrations of an added probe (if a target nucleic acid and a target nucleic acid probe are higher in concentrations, the time for completed hybridization becomes shorter; if contrary to the former, the reaction time becomes longer. If a target nucleic acid and a probe are higher in concentrations, a Tm value is higher; if contrary to the former, it becomes lower); as a result, there is such problems that (1) an assaying system needs to be optimized in every concentration of a probe, and (2) a calculating curve needs to be prepared in every concentration of an added probe.

Non-patent reference 1: Protein, Nucleic Acid and Enzyme; vol. 35, No. 17, Kyoritu Shuppan Co., Ltd.; Experimental Medical; vol. 15, No. 7, 1997, Yodosha Co., Ltd.

DISCLOSURE OF THE INVENTION

Problems to be Solved by Invention

With the foregoing circumstances in view, the present invention has as an object to provide a novel mixture for assaying a target nucleic acid, characterized by enabling a nucleic acid assaying method to assay a target nucleic acid without requiring any processing step of diluting of a target nucleic acid and any procedures of changing a probe concentration, a novel method for assaying a nucleic acid using the same, and a novel nucleic acid probe to be used for these.

Means to be Solved Problems

As a result of an extensive investigation, the present inventors have obtained the following findings and completed the present invention. That is, a target nucleic acid is added to a reaction solution (a hybridizing reaction system) comprising a known concentration of a specific internal standard nucleic acid, a specific target nucleic acid probe labeled with a fluorescent dye for a homogenous solution system and/or a specific internal standard nucleic acid probe labeled with a fluorescent dye and making it possible to hybridize the above internal standard nucleic acid, and then, is allowed to make a hybridizing reaction; while an occurred change of an optical character is measured. Further a measured-value ratio of the internal standard nucleic acid and the target nucleic acid is determined; these steps enabled the present invention to be completed.

Described specifically, the present invention provides:

1) Novel mixture or novel reaction solution (hereinafter, the both together are collectively called simply a "novel mixture".) for assaying one or two or more target nucleic acids, which comprises one or two or more below nucleic acid probes for a homogenous solution system and one or two or more below internal standard nucleic acid, or further one or two or more below internal standard nucleic acid probe:

A) Nucleic acid probe for homogenous solution system (hereinafter, called a "target nucleic acid probe") having below characteristics:

a) said target nucleic acid probe is formed of one stranded oligonucleotide;

b) said target nucleic acid probe is labeled with one or two or more molecule of fluorescent dyes of one or two or more kinds at least one of both end portions and/or at least one of base portions in the chain, at least one of sugar moieties and/or at least one of phosphate moieties of the oligonucleotide;

c) said target nucleic acid probe enables a fluorescent character to change on hybridizing with a target nucleic acid and/or an internal standard nucleic acid;

d) said target nucleic acid probe is capable of hybridizing without discriminating with a target nucleic acid or an internal standard nucleic acid;

e) said target nucleic acid probe is capable of producing a difference between the amount of a change in a fluorescent character on hybridizing with an internal standard nucleic acid and that on hybridizing with a target nucleic acid;

B) Internal standard nucleic acid (called an "internal gene" or an "internal standard gene" in a case) wherein said internal standard nucleic acid has a structure different in at least a portion from the structure of a target nucleic acid of a region corresponding to the above target nucleic acid probe, and is capable of producing a difference between the amount of a change in a fluorescent character produced on hybridizing with the above target nucleic acid probe and one on the hybridization of a target nucleic acid with the above target nucleic acid probe;

C) Internal standard nucleic acid probe:
wherein said internal standard nucleic acid probe has the following characteristics:
said internal standard nucleic acid probe has the above characteristics a) to e) of the above target nucleic acid probe, wherein a fluorescent labeling portion and a fluorescent character of a labeled fluorescent dye each are different from those of the above target nucleic acid probe;

2) a novel mixture according to the above 1), wherein said target nucleic acid probe is a probe having a base sequence not complementary to a target nucleic acid in a partial region;

3) a novel mixture according to the above 1), wherein if said nucleic acids are labeled with two or more fluorescent dyes, the probes are labeled with the fluorescent dyes which are with each other different in their optical character;

4) a novel mixture according to the above 1), wherein the amount of a change in an optical character is the increased amount (for example, a probe labeled with dyes each causing an FRET phenomena) or the decreased amount (for example, a Q probe);

5) a novel mixture according to the above 1) or 3), wherein said target nucleic acid probe and/or said internal standard nucleic acid probe are/is a probe labeled at least two portions (end portions, base portions in an chain, sugar moieties, phosphate moieties) with fluorescent dyes with different fluorescent character occurred on hybridization of a target nucleic acid probe and/or an internal standard nucleic acid probe with a target nucleic acid and/or an internal standard nucleic acid (hereinafter, these probes are called simply "a doubly-labeled nucleic acid probe");

6) a novel mixture according to the above 5), wherein said at least two portions are at least two bases;

7) a novel mixture according to the above 6), wherein said bases are cytosine (hereinafter a cytosine is called simply a "C");

8) a novel mixture according to the above 7, wherein C's are bases of both ends;

9) a novel mixture according to the above 1) or 5), wherein a base sequence of a target nucleic acid probe is complementary to a target nucleic acid and an internal standard nucleic acid excluding both base end portions (portions comprising from the $1^{st}$ base to the $3^{rd}$ base in length; the end base being counted as the "$1^{st}$ base");

10) a novel mixture according to the above 5), wherein said doubly-labeled nucleic acid probe is a doubly-labeled nucleic acid probe making at one portion of the labeled portions a difference between the amount of a change in a fluorescent character on hybridization with a target nucleic acid and that on hybridization with an internal standard nucleic acid, but not making such a difference at the other portion;

11) a novel mixture according to the above 1) or 5), wherein a base sequence of said target nucleic acid probe or said doubly-labeled nucleic acid is at least complementary to a target nucleic acid or an internal standard nucleic acid excluding both end base portions (a base sequence of from at least the $1^{st}$ base to the $3^{rd}$ base in length; with the end base being counted as the $1^{st}$ base);

12) a novel mixture according to the above 1) or 5), wherein a base sequence of said target nucleic acid probe or said doubly-labeled nucleic acid probe is not complementary to a target nucleic acid and/or an internal standard nucleic acid at an end portion opposite an end portion labeled with a fluorescent dye;

13) a novel mixture according to the above 1) or 5), wherein said target nucleic acid or said doubly-labeled nucleic acid has at least a base sequence completely complementary to a target nucleic acid and an internal standard nucleic acid;

14) a novel mixture according to the above 1) or 5), wherein, if the base of a target nucleic acid corresponding to an end base of a target nucleic acid probe or a doubly-labeled nucleic acid probe is counted as $1^{st}$ base, the number of a G of the corresponding target nucleic acid and internal standard nucleic acid in a end base sequence of from the $1^{st}$ base to the $3^{rd}$ base is larger in a target nucleic acid than in an internal standard nucleic acid, or smaller in a target nucleic acid than in an internal standard nucleic acid;

15) a novel mixture according to the above 1) or 5), wherein, if the base of a target nucleic acid corresponding to both end base of a target nucleic acid probe or a doubly-labeled nucleic acid probe is counted as the $1^{st}$ base, the number of G of the corresponding target nucleic acid and internal standard nucleic acid in a end base sequence of from the $1^{st}$ base to the $3^{rd}$ base is larger in a target nucleic acid than in an internal standard nucleic acid in one end region, and in the other end region smaller in a target nucleic acid than or equal in an internal standard nucleic acid in other end region; or in one end region smaller in a target nucleic acid than in an internal standard nucleic acid and in the other end region larger in a target nucleic acid than or equal in an internal standard nucleic acid;

16) a novel mixture according to the above 1) or 5), wherein the base of a target nucleic acid corresponding to one end base of a target nucleic acid probe or a doubly-labeled nucleic acid probe is a base other than a G and the base corresponding to the other end base is a G;

17) a novel mixture according to the above 1) or 5), wherein if any of two bases of a target nucleic acid corresponding to both end bases of a target nucleic acid probe is a G, that of an internal standard nucleic acid is a base other than a G; and if that of a target nucleic acid is a base other than a G, that of an internal standard nucleic acid is a G;

18) a novel mixture according to the above 1) or 5), wherein, if the base of a target nucleic acid corresponding to both end base of a target nucleic acid probe or a doubly-labeled nucleic acid probe is counted as the $1^{st}$ base, the corresponding base sequence of a target nucleic acid and internal standard nucleic acid in a end base sequence of from the 1$^{st}$ base to the 3$^{rd}$ base is different in one end region, but the same in the other end region;

19) a novel mixture according to the above 1) or 5), wherein said mixture comprises further one or two or more sorts of D) fluorescence-quenching substance enabling the fluorescence of a target nucleic acid probe or a doubly-labeled nucleic acid probe having not hybridized with a target nucleic acid and an internal standard nucleic acid to reduce, or one or two or more sorts of oligonucleotide labeled with E) the fluorescence-quenching substance (hereinafter, called simply "quenching substance-labeled probe");

20) a novel mixture according to the above 19), wherein said quenching substance-labeled probe has the below characteristics (1) and/or (2):

The characteristics:

(1) The dissociating temperature of the hybrid complex of a target nucleic acid probe or a doubly-labeled nucleic acid probe and a fluorescent quenching substance-labeled probe is lower than the dissociating temperature of the hybrid complex of a target nucleic acid probe or a doubly-labeled nucleic acid probe and a nucleic acid or an internal standard nucleic acid.

(2) After the hybridization of a target nucleic acid probe or a doubly-labeled nucleic acid probe with a target nucleic acid, or after the hybridization of a target nucleic acid probe or a doubly-labeled nucleic acid probe with a target nucleic acid, a fluorescent quenching substance—labeled probe can hybridize with a probe for a homogenous solution system or a doubly-labeled nucleic acid probe due to the characteristics of the above (1).

21) a novel mixture according the above 1), wherein said novel mixture comprises a) an internal standard nucleic acid, b) a target nucleic acid probe and/or c) an internal standard nucleic acid probe according to the above 1), and d) exonuclease under the below conditions or exonuclease attached to the novel mixture as a kit;

the conditions: a target nucleic acid probe and/or an internal standard nucleic acid probe are not complementary to at least one of a target nucleic acid and an internal standard nucleic acid at a fluorescent-labeled portion region (the region: 1 (one) to 3 base in length, preferably 1 (one) base);

22) a novel mixture according to the above 21), wherein said exonuclease is 3'→5' exonuclease, 5'→3' exonuclease, S1 nuclease or Mung Bean Nuclease;

23) a novel mixture according to the above 1), wherein said novel mixture comprises one or two or more pairs of internal standard probes and target nucleic acid probes;

24) a novel method for assaying a target nucleic acid, comprising assaying one or two or more target nucleic acids using the novel mixture according to the above 1);

25) a novel method for assaying a target nucleic acid according to the above 24), wherein said novel method comprises:

conducting a hybridizing reaction under the presence of one or two or more target nucleic acids and/or one or two or more internal standard nucleic acids;

measuring a change in a fluorescent character of the reaction system, which change is derived from a fluorescent dye labeled at a target nucleic acid probe and/or an internal standard nucleic acid probe and calculating a ratio of the obtained measuring values; and determining concentrations of one or two or more target nucleic acids based on the obtained ratio;

26) a novel method for assaying one or two or more target nucleic acids according to the above 24), wherein said target nucleic acid is a nucleic acid amplified by a gene amplification method (until any phase of an initial phase, a middle phase and a stationary phase);

27) a novel method for assaying one or two or more target nucleic acids according to the above 24), wherein said target nucleic acid is at least one of a target nucleic acid and internal standard nucleic acid amplified by a gene amplification method;

28) a novel method for assaying one or two or more target nucleic acids according to the above 24), wherein said target nucleic acid is at least one of a target nucleic acid and internal standard nucleic acid amplified by a gene amplification method using a same primer set;

29) a novel method for assaying one or two or more target nucleic acids according to the above, wherein said novel mixture according to any one of the above 1) to 23) comprises the following target nucleic acid probe or doubly-labeled nucleic acid probe and a known concentration of an internal standard nucleic acid according to any one of the above 1) to 20);

Target nucleic acid probe (hereinafter, this kind of a probe will be called a "recognizable nucleic acid probe"): a target nucleic acid probe according to any one of the above 1) to 23) is not complementary to any one of a target nucleic acid and an internal standard nucleic acid at at least any one or two or more ones of portions labeled with a fluorescent dye(s).

Doubly-labeled nucleic acid probe (hereinafter, this sort of a probe will be called a "recognizable doubly-labeled nucleic acid"): a doubly-labeled nucleic acid probe according to any one of the above 5) to 23) is not complementary to any one of a target nucleic acid and an internal standard nucleic acid at any one of portions labeled with any one of two sorts of fluorescent dyes.

30) a novel method for assaying one or two or more target nucleic acids according to the above 29), wherein said novel method comprises:

measuring the amount of changes in fluorescent characters derived from a target nucleic acid probe and an internal standard nucleic acid probe;

calculating a ratio of the amount of a change in a fluorescent character from the target nucleic acid probe to the amount of a change in a fluorescent character from the internal standard nucleic acid probe based on the obtained measuring values;

calculating a constituent ratio of the target nucleic acid and the internal standard nucleic acid based on the obtained ratio; and determining a concentration of a target nucleic acid based on the obtained constituent ratio;

31) a novel method for assaying one or two or more target nucleic acids, wherein, in the method for assaying a nucleic acid according to the above 24) or 29), the fluorescence emission are made to quench for a target nucleic acid probe or internal standard nucleic acid probe not hybridized with any of an internal standard nucleic acid and a target nucleic acid;

32) a novel method for assaying one or two or mote target nucleic acids according to the above 31), wherein said quenching of a fluorescent emission is conducted by using a quenching substance having an effect quenching a fluorescence emission and/or a quenching substance-labeled probe having the same effect;

33) a calculating equation represented by the following equation for calculating accurately a target nucleic acid based on measuring values of a change in an optical character in the novel method for assaying a target nucleic acid according to the above 24) or 29);

$$x=(-a'-B+Ba'+b'+A-Ab')/(b'-b-Ab'+Ab-a'+a+Ba'-Ba)$$

wherein said equation is valid under the below conditions; and said signs have the below meanings:

The conditions are as follows: in the novel method, the doubly-labeled nucleic acid probe is used, wherein said nucleic acid probe is labeled with dyes A and B.

The signs are as follows:
y: a proportion of a hybridized probe;
1−y: a proportion of non-hybridized probe;
x: a proportion of a target gene;
1−x: a proportion of an internal standard gene;
A: a ratio of the fluorescent intensity of dye A of the doubly-labeled nucleic acid probe on no hybridization in use of a practical sample to the fluorescent intensity of dye A of the doubly-labeled nucleic probe on no hybridization;
a: a ratio of the fluorescent intensity of dye A of the doubly-labeled nucleic acid probe on its 100%-hybridization with a target nucleic acid to the fluorescent intensity of dye A of the doubly-labeled nucleic acid probe on no hybridization;
a': a ratio of the fluorescent intensity of dye A of the doubly-labeled nucleic acid probe on its 100%-hybridization with an internal standard nucleic acid to the fluorescent intensity of dye A of the doubly-labeled nucleic acid probe on no hybridization;
B: a ratio of the fluorescent intensity of dye B of the doubly-labeled nucleic acid probe on no hybridization using a practical sample to the fluorescent intensity of dye B of the doubly-labeled nucleic probe on no hybridization;
b: a ratio of the fluorescent intensity of dye B of the doubly-labeled nucleic acid probe on its 100%-hybridization with a target gene to the fluorescent intensity of dye B of the doubly-labeled nucleic acid probe on no hybridization;
b': a ratio of the fluorescent intensity of dye B of the doubly-labeled nucleic acid probe on its 100%-hybridization with an internal standard nucleic acid to the fluorescent intensity of dye B of the doubly-labeled nucleic acid probe on no hybridization.

34) a calculating equation represented by the following equation for calculating accurately a target nucleic acid based on measuring values of a change in an optical character in the novel method for assaying a target nucleic acid according to the above 24) or 29);

$$x=(b-B-Ab+A+a'B-a')/(a'B-a'-aB+a)$$

wherein said equation is valid under the below conditions; and said signs have the below meanings:

The conditions are as follows: in the novel method, the doubly-labeled nucleic acid probe is used, wherein said nucleic acid probe is labeled with dyes A and B.

The signs are as follows:
y: a proportion of a hybridized probe;
1−y: a proportion of non-hybridized probe;
x: a proportion of a target gene;
1−x: a proportion of an internal standard gene;
A: a ratio of the fluorescent intensity for dye A of the doubly-labeled nucleic acid probe on use of a practical sample to the fluorescent intensity for dye A of non-hybridizing doubly-labeled nucleic acid probe;
a: a ratio of the fluorescent intensity for dye A of the doubly-labeled nucleic acid probe on its 100%-hybridization with a target nucleic acid to the fluorescent intensity for dye A of non-hybridizing doubly-labeled nucleic acid probe;
a': a ratio of the fluorescent intensity for dye A of the doubly-labeled nucleic acid probe on the 100%-hybridization of the doubly-labeled nucleic acid probe with an internal standard nucleic acid to the fluorescent intensity for dye A of the doubly-labeled probe on 100%-hybridization of the doubly-labeled nucleic acid probe with the quenching substance-labeled probe;
B: a ratio of the fluorescent intensity of dye B of the doubly-labeled nucleic acid probe on use of a practical sample to the fluorescent intensity of dye B of the doubly-labeled nucleic probe on its 100%-hybridization with a quenching substance-labeled nucleic acid probe;
b: a ratio of the fluorescent intensity of dye B of the doubly-labeled nucleic acid probe on its 100%-hybridization with a target gene and an internal standard gene to the fluorescent intensity of dye B of the doubly-labeled nucleic acid probe on its 100%-hybridization with a quenching substance-labeled nucleic acid probe.

35) A kit for assaying a nucleic acid, comprising a novel mixture according to the above 1) or 5);

36) a novel method for assaying a nucleic acid, which comprises: amplifying one or plural target nucleic acids and an internal standard nucleic acid in a reaction system comprising one or plural internal standard nucleic acids until an optional phase of from a beginning phase to a stationary phase by a gene-amplification method; and determining starting concentrations prior to the amplification of one or plural target nucleic acids by using the resultant reaction or the amplified product as a sample;

37) a method for assaying one or plural nucleic acids prior to an amplification according to the above 32), wherein said gene-amplification method is a method for amplifying a target nucleic acid and an internal standard nucleic acid by using a primer set common to the amplification of the target nucleic acid and to that of an internal standard nucleic acid;

38) a method for assaying one or plural nucleic acids prior to amplification according to the above 36), wherein the primer for said amplification is a Q probe;

39) a novel mixture for assaying one or plural target nucleic acids based on measurement of a Tm value, which comprises a pair of a below nucleic acid and a below internal standard nucleic acid;

The target nucleic acid probe: which is one-strand oligonucleotide labeled with one or two or more fluorescent dyes, wherein said oligonucleotide is capable of hybridizing with a target nucleic acid and an internal standard nucleic acid, and enables a change of a fluorescent character of the labeled fluorescent dyes on hybridization with the nucleic acid and internal standard nucleic acid, wherein in plural nucleic acid probes the fluorescent dyes of the probes each are different.

The internal standard nucleic acid: in which the base sequence of a portion of said internal standard nucleic acid hybridizing with said nucleic acid probe is different in part from the base-sequence of a portion of a target nucleic acid hybridizing with said nucleic acid probe.

40) a novel mixture for assaying one or plural target nucleic acids based on measurement of a Tm value according to the above 39), wherein said nucleic acid probe is a single stranded oligonucleotide labeled with a fluorescent dye at a cytosine portion of the oligonucleotide;

41) a novel mixture for assaying one or plural target nucleic acids based on measurement of a Tm value according to the above 39), wherein said change in a fluorescent character for a fluorescent dye is a decrease in fluorescent intensity;

42) a novel mixture for assaying one or plural target nucleic acids based on measurement of a Tm value according to the above 35), wherein said change in a fluorescent character for a fluorescent dye is an increase in fluorescent intensity;

43) a novel method for assaying a target nucleic acid, which comprises measuring fluorescent intensity using said novel mixture according to the above 39) with changing temperature under the presence of plural target nucleic acids; and determining a target nucleic acid by the following procedures:

the procedures comprising:

1) drawing a curve responding to a change in fluorescent intensity measured;

2) differentiating the resulting curve;

3) integrating the resulting peak(s) and determining the area(s) of the peak(s);

4) calculating a ratio(s) between the resulting peak area(s) of the internal standard nucleic acid and the resulting peak area(s) of the target nucleic acid;

5) multiplying the concentration of the internal standard nucleic acid by said ratio.

44) a novel method for assaying a nucleic acid according to the above 37), wherein said target nucleic acid is a nucleic acid product amplified by a gene amplification method in a reaction solution system containing an internal standard nucleic acid according to the above 35);

45) a novel method for assaying a nucleic acid according to the above 43), wherein said primer is a Q probe;

46) a kit for assaying a nucleic acid, which comprises a novel mixture according to the above 1) or 39);

47) a target nucleic acid probe or a doubly-labeled nucleic acid probe, in which said target nucleic acid probe or doubly-labeled nucleic acid probe is described above and has at least any one of the below structures:

1. Structures of said target nucleic acid probe, wherein (1) said structure has a portion not complementary to a target nucleic acid and/or an internal standard nucleic acid at a end portion or both end portions;

(2) in the above (1), said nucleic acid probe is labeled with a fluorescent dye at one portion not complementary to the target nucleic acid and/or an internal standard nucleic acid, having a cytosine (a C) or a guanine (a G) in a range of 1 to 3 bases from the labeled base in a fluorescent dye-labeled portion (the labeled base is numbered as 1 (one));

(3) in the above (1), the one other portion not complementary to a target nucleic acid and/or an internal standard nucleic acid is a portion opposite the one end portion labeled with a fluorescent dye;

(4) in the above (1), one other portion not complementary to a target nucleic acid and/or an internal standard nucleic acid is in a range of 1(one) to 4 bases as the number of bases;

(5) in the above (1), if any of two bases of a target nucleic acid corresponding to the both ends of the target nucleic acid probes is a G, that of the internal standard nucleic acid is a base other than a G; if that of the target nucleic acid is a base other than a G, that of an internal standard is a G.

2. Structures of a doubly-labeled target nucleic acid probe, wherein, (6) portions labeled with fluorescent dyes were at least two bases;

(7) the bases according to the above (6) are two C's;

(8) the two C's according to the above (7) are the bases of both ends;

(9) the base sequence according to the above (6) are complementary to a target nucleic acid or an internal standard nucleic acid excluding both end portion (at least from the $1^{st}$ base to the $3^{rd}$ base, the end base being counted as the $1^{st}$ base);

(10) the doubly-labeled nucleic acid probe according to the above (6) or (9) is a doubly-labeled nucleic acid probe making at one portion a difference between the amount of change in a fluorescent character on hybridization with a target nucleic acid and that on hybridization with an internal standard nucleic acid, but not making such a difference at the other portion;

3. Structures common to a target nucleic acid probe and a doubly-labeled nucleic acid probe: wherein

(11) in any one of the above (1) to (10), a base sequence of a target nucleic acid probe or a doubly-labeled nucleic acid is at least complementary to a target nucleic acid or an internal standard nucleic acid excluding to both end base portions (a base sequence of at least from the $1^{st}$ base to the $3^{rd}$ base; the end base being counted as the $1^{st}$ base);

(12) in any one of the above (1) to (11), a target nucleic acid probe or a doubly-labeled nucleic acid probe has a base sequence completely complementary to a target nucleic acid and an internal standard nucleic acid;

(13) in any one of the above (1) to (12), if the base of a target nucleic acid corresponding to an end base of a target nucleic acid probe or a doubly-labeled nucleic acid probe is taken as the $1^{st}$ base, the number of a G of the corresponding target nucleic acid and internal standard nucleic acid in a end base sequence of from the $1^{st}$ base to the $3^{rd}$ base is larger in a target nucleic acid than in an internal standard nucleic acid, or smaller in a target nucleic acid than in an internal standard nucleic acid;

(14) in any one of the above (1) to (13) if the base of a target nucleic acid corresponding to both end base of a target nucleic acid probe or a doubly-labeled nucleic acid probe is taken as the $1^{st}$ base, the number of G of the corresponding target nucleic acid and internal standard nucleic acid in a end base sequence of from the $1^{st}$ base to the $3^{rd}$ base is larger in a target nucleic acid than in an internal standard nucleic acid in one end region, and in other end region smaller in a target nucleic acid than or equal in an internal standard nucleic acid in other end rejoin; or in one end region smaller in a target nucleic acid than in an internal standard nucleic acid and in other end region larger in a target nucleic acid than or equal in an internal standard nucleic acid;

(15) a novel mixture according to the above 1) or 5), wherein, in any one of the above (1) to (14), the base of a target nucleic acid corresponding to one end base of a target nucleic acid probe or a doubly-labeled nucleic acid probe is a base other than a G and the base corresponding to the other end base is a G.

(16) in any one of the above (1) to (15), if any of two bases of a target nucleic acid corresponding to both end bases a target nucleic acid probe is a G, that of an internal standard nucleic acid is other than a G; and if that of a target nucleic acid is other than a G, that of an internal standard nucleic acid is a G;

(17) in any one of the above, if the base of a target nucleic acid corresponding to both end base of a target nucleic acid probe or a doubly-labeled nucleic acid probe is taken as the $1^{st}$ base, the corresponding base sequence of a target nucleic acid and internal standard nucleic acid in a end base sequence of from the $1^{st}$ base to the $3^{rd}$ base is different in the one end region, but the same in the other end region.

Advantageous Effect of the Invention

A novel method having the following characteristics is completed by using the above novel mixture according to the present invention. That is, in the method for assaying a nucleic acid, 1) processing steps for diluting a target nucleic acid are not required; 2) a change of the concentration of a nucleic acid for use with response to the concentration of a target nucleic acid are not required; 3) plural target nucleic acids can be assayed in a like assaying system; 4) an assaying sensitivity is enhanced; and 5) the combination of a method for assaying a nucleic acid according to the present invention and a method for amplifying a nucleic acid provides the following merits:

(1) subsequent to the completion of a gene amplifying reaction, the combined method makes it possible to assay in a rapid and convenient way a nucleic acid without opening a reaction tube for the gene amplifying reaction; therefore, it does not require a PCR post processing step and can simply, easily and rapidly assay a nucleic acid; (2) to open a gene-amplifying reaction tube is not needed; the combined method does not have any risk of contamination with amplified products; (3) the assay is hard to be affected by inhibitors because the combined method is a competitive method; (4) since a gene-amplifying processing-step and a detecting processing step of a amplified product can be completely divided, a large quantity-sample becomes to be treated; and a sample-treating power can be conveniently and non-expensively improved (for example, subsequent to the gene-amplification by using plural non-expensive PCR-apparatuses not having any fluorescence-measuring function, by analyzing obtained data in order using a fluorescence-measuring apparatus, using even one fluorescence-measuring apparatus, a large quantitative-sample can be treated.); (5) a nucleic acid becomes to be assayed by a markedly simple and non-expensive measuring apparatus because the amplifying processing of a nucleic acid is needed not to be monitored in a real time way and the measuring apparatus is needed to have a thermally-cycling function indispensable to measuring a PCR processing.

BRIEF DESCRIPTION OF THE DRAWINGS

FIG. 1 illustrates an outline of a method for detecting a target gene and an internal standard gene by using a Qprobe.

FIG. 3 illustrates an outline of a method for assaying quantitatively a gene by using a doubly-labeled Qprobe (a switching probe).

FIG. 13 illustrates an outline of a method for detecting a gene by using a doubly-labeled nucleic acid probe (its part 3).

FIG. 15 is an illustrative figure concerning conditions of a probe and a fluorescent change.

FIG. 17 illustrates the detection of a target gene and an internal standard gene under the no presence of a quenching substance-labeled nucleic acid probe or under the presence of it.

FIG. 18 illustrates an outline of a method for using an enzyme having a 3'→5' exonuclease activity.

FIG. 20 illustrates an outline of a method for assaying quantitatively a gene by using a combination of a doubly-labeled nucleic acid probe and a quenching substance-labeled nucleic acid probe.

BEST MODES FOR CARRYING OUT THE INVENTION

Figure 2:
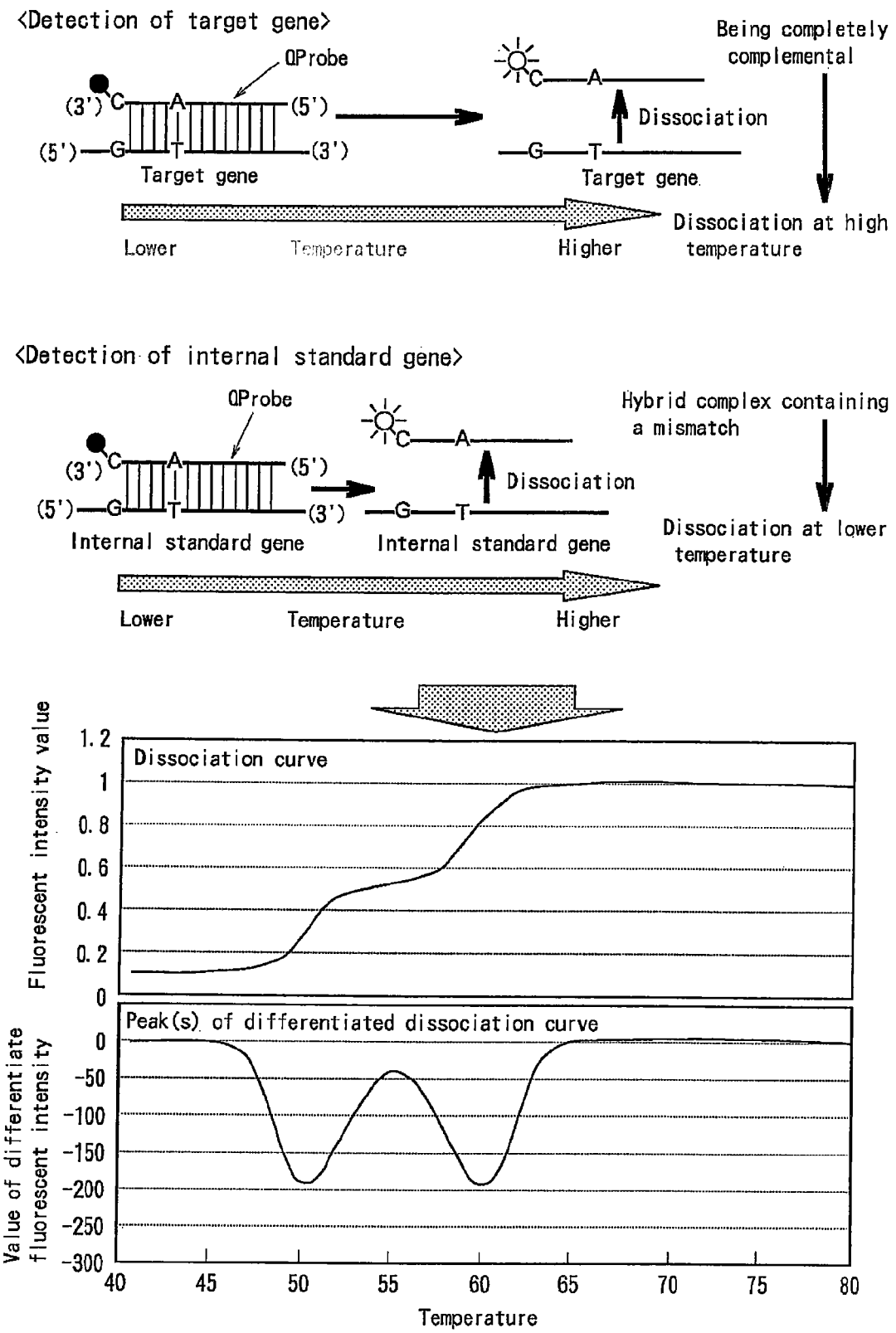
FIG. 2 illustrates an outline of a method for assaying quantitatively a gene by a dissociation curve (Tm) analysis using a Qprobe.
Figure 4:
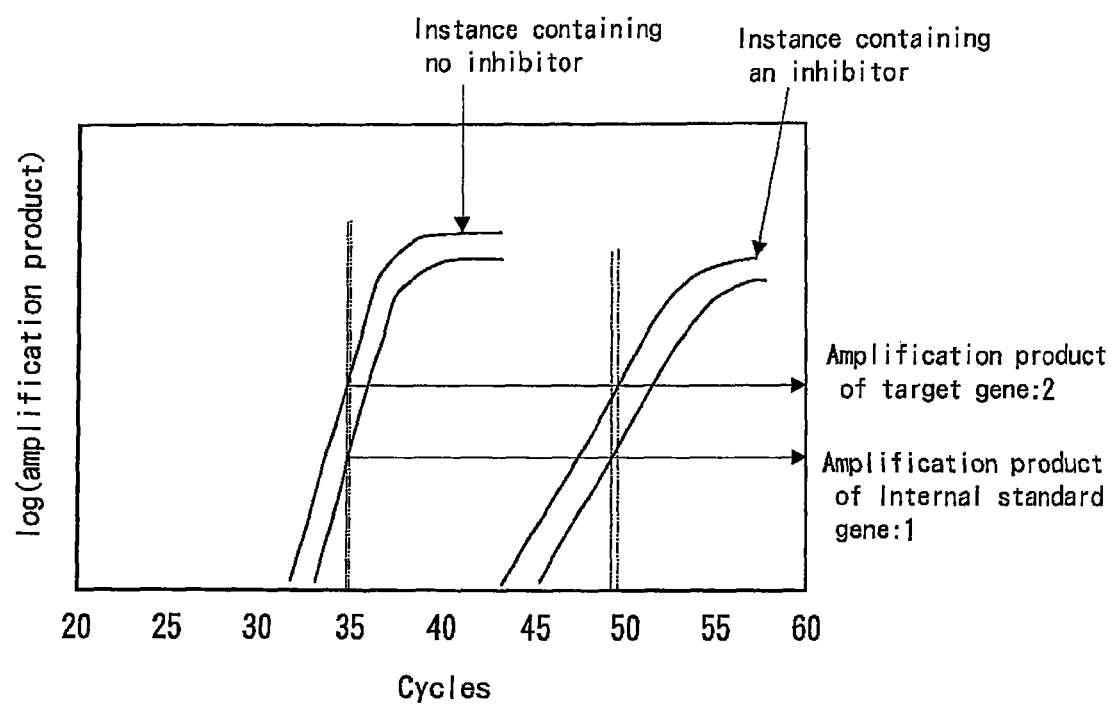
FIG. 4 illustrates an outline of the principle for a competitive PCR method.

The present invention will hereinafter be described in detail. Before describing the present invention in detail, however, definitions will be provided for certain terms used throughout the application including the claims. It is to be noted that the terms employed in the present invention have the same meanings as those used commonly in molecular biology, genetics or genetic engineering, or microbiology or microbial engineering unless otherwise specifically indicated.

The terms "one or two or more", "one or two or more" and "one or plural" as used herein mean "at least one".

The term "target nucleic acid" as used herein means a nucleic acid the detection or quantitatively assaying of which is intended.

A gene should be compassed in the terms "nucleic acid", "target nucleic acid" and "internal standard nucleic acid". In this specification, as general terms, "a target nucleic acid", "an internal standard nucleic acid", or simply "nucleic acid" are used; as specific terms, "target gene", "internal standard gene", or simply "gene" are used.

The term "a nucleic acid contained in a sample" may be also called simply a target nucleic acid or an objective nucleic acid.

The expression "to assay a nucleic acid" or "to measure the concentration of a nucleic acid" as use herein means to perform a quantitative detection of the nucleic acid, to perform a qualitative detection of the nucleic acid, to simply measure or simply monitor the intensity of fluorescence from a nucleic acid polymerization system, or to measure a change or the amount of a change in an optical character of target nucleic acid(s) in an assaying reaction system by using a plural wavelength and then to calculate a ratio between the measuring values, followed by to determine the concentration of the target nucleic acid with the ratio. The above expression should also be interpreted to encompass an operation or the like that the data obtained as described above is studied by the known method of Kurata et al. (EP 1 046 717 A9) to determine the concentration (the number of copies or the like) of a nucleic acid existing in a single system.

Based on the above reason, the term "a nucleic acid contained in a sample" as used herein should be not only limited to any specific nucleic acid(s) to be assayed, but also should be interpreted to include an unspecified nucleic acid capable of be detected by the method according to the present invention with no intention. Needless say, it encompasses genes and the like. These nucleic acids may exist together. In addition, no limitation is imposed on the concentration or size of those. These nucleic acids should be interpreted to encompass further a DNA, an RNA and the modified nucleic acids thereof.

The term "optical character" means one of various absorption spectra and fluorescence emission spectrum of a fluorescent dye, quencher or the like, with which a nucleotide is labeled, or its optical characteristic or the like such as absorption intensity, polarization, fluorescence emission, fluorescence intensity, fluorescence lifetime, fluorescence polarization or fluorescence anisotropy (these optical characteristics will be collectively called "fluorescence intensity"). It may also mean a characteristic determined by totally analyzing one or more measurement values of at least one fluorescent dye or the like, with which a labeled nucleotide or the like is labeled, as measured at at least one measurement wavelength. For example, a fluorescence intensity curve or the like of a modification reaction of a nucleic acid can be used as an optical character.

Further, as a general term, a "optical character" is used; as a specific term, a "fluorescent intensity", or simply "fluorescence" is used.

In the present invention, the expression "from a change or the amount of a change in fluorescence intensity" shall embrace not only a change in fluorescence intensity on the basis of a nucleic acid polymer synthesized in the present invention, but also a change or the amount of a change in fluorescence intensity when a nucleic acid probe for a homogeneous solution system, said nucleic acid probe having been labeled with a fluorescent dye and/or quencher, is hybridized with the amplified nucleic acid.

A hybridization complex between a primer probe and a corresponding nucleic acid is called a "hybrid" or a "hybrid complex", or simply a "nucleic acid-primer, complex" or a "primer-nucleic acid complex".

In the present invention, for example, such terms are used that a nucleic acid probe "complements" or "is complementary to", or in addition "does not complement" or "is not complementary to" a target nucleic acid at a partial region of the probe. These terms "complements" or "is complementary to" means that when two kinds of oligonucleotides exist in a single system, the nucleic acids can bind each other's at corresponding bases by hydrogen bonding. In addition, it means that one of the nucleic acids can hybridize with the other. Further, such a term is used that a partial region of a nucleic acid probe "corresponds with" a partial region of a target nucleic acid: the term "correspond with" in this instance has no concept of the hydrogen bonding between corresponding bases; and it means that simply the nucleic acids have a relation of one to one. Accordingly, the term "correspond" means both of "complement" or "be complementary to" and "do not complement" or "be not complementary to".

The term a "change ratio in an optical character" as used the present invention means a ratio of an optical measuring-value of a fluorescent dye or the like in a reaction system or an assaying system on no hybridization of a nucleic acid probe (a target nucleic acid probe, an internal standard nucleic acid probe) with a target nucleic acid and/or an internal standard nucleic acid to that on hybridization. As an example, an calculating equation such as (a measuring value on hybridization)/(a measuring value on no hybridization)× 100 may be illustrated. If the change is a quenching in fluorescence, it is called a "fluorescence-quenching ratio"; while if an emission in fluorescence, a "fluorescent emission ratio" or the like. The hybridization occurs preferably at 10° C. to 90° C.; the no hybridization occurs at 90° C. or more. There is an intermediate hybridization; accordingly, it is preferable to measure accurately every each experiment.

Incidentally, a portion at which a nucleic acid probe according to the present invention is labeled with a fluorescent dye according to the present invention is called a "fluorescent dye-labeled portion" or "fluorescence-labeled portion"; these terms have, however, the same meanings.

The term "fluorescent dye (which may also be called 'fluorescent substance')" as used in the present invention generally means a fluorescent dye which is generally used to label a nucleic acid probe to assay or detect the nucleic acid. Illustrative are fluorescein and its derivatives [for example, fluorescein isothiocyanate (FITC) and its derivatives], Alexa 488, Alexa 532 (5-(4-Carboxylatophenyl)-1,2,3,7,8,9-hexahydro-2,3,3,7,7,8-hexamethyl-10,12-disulfopyrano[3,2-f:5,6-f']diindole-11-ium), CY3 (1-[6-[(2,5-Dioxo-1-pyrrolidiny)oxy]-6-oxohexyl]-2-[3-[1-[6-[(2,5-dioxo-1-pyrrolidinyl)oxy]-6-oxohexyl]-1,3-dihydro-3,3-dimethyl-5-sulfo-2H-indole-2-ylidene]-1-propenyl]-3,3-dimethyl-5-sulfo-3H-indolium), CY5 (5-[2-[(2,5-Dioxo-1-pyrrolidinyl)oxy]-2-oxoethyl]-2-[5-[[5-[2-[(2,5-dioxo-1-pyrrolidinyl)oxy]-2-oxoethyl]-1,3-dihydro-3,3-dimethyl-1-(4-sodiosulfobutyl)-2H-indol]-2-ylidene]-1,3-pentadienyl]-3,3-dimethyl-1-(4-sulfonatobutyl)-3H-indolium, Sulfoindocyanine succinimidyl ester), 6-JOE (4',5'-dichloro-2',7'-dimethoxyfulorescein), EDANS, rhodamine 6G (R6G) and its derivatives [for example, tetramethylrhodamine (TMR), tetramethylrhodamine isothiocynate (TMRITC), and x-rhodamine], Texas red, "BODIPY FL" (4,4-difluoro-5,7-dimethyl-4-bora-3a,4a-diaza-s-indacene-3-propionic acid "BODIPY" is a trademark, "FL" is a tradename; product of Molecular Probes Corporation, U.S.A.; this will hereinafter apply equally), "BODIPYFL/C3", "BODIPYFL/C6", "BODIPY5-FAM", "BODIPY 493/504", "BODIPY TMR", and their derivatives (for example, "BODIPY TR", "BODIPY R6G"), and "BODIPY 564", "BODIPY 581", TAMRA Carboxytetramethylrhodamine), Pacific Blue (Tradename; 2-Oxo-6,8-difluoro-7-hydroxy-2H-1-benzopyran-3-carboxylic acid Molecular Probes Co., USA), and the like.

Among the above-exemplified fluorescent dyes, TAMRA (Carboxytetramethylrhodamine), FITC, EDANS, Texas Red (Sulforhodamine 101 Sulfonyl Chloride), 6-JOE (4',5'-dichloro-2',7'-dimethoxyfulorescein), TMR, Alexa 488, Alexa 532 (5-(4-Carboxylatophenyl)-1,2,3,7,8,9-hexahydro-2,3,3, 7,7,8-hexamethyl-10,12-disulfopyrano[3,2-f:5,6-f']diindole-11-ium), "BODIPYFL/C3", "BODIPYR6G", "BODIPY FL", "BODIPYFL/C6", "BODIPY TMR", 5-FAM, "BODIPY 493/503", "BODIPY 564", "BODIPY 581", CY3 (1-[6-[(2,5-Dioxo-1-pyrrolidinyl)oxy]-6-oxohexyl]-2-[3-[1-[6-[(2,5-dioxo-1-pyrrolidinyl)oxy]-6-oxohexyl]-1,3-dihydro-3,3-dimethyl-5-sulfo-2H-indole-2-ylidene]-1-propenyl]-3,3-dimethyl-5-sulfo-3H-indolium), CY5 (-[2-[(2,5-Dioxo-1-pyrrolidinyl)oxy]-2-oxoethyl]-2-[5-[[5-[2-[(2,5-dioxo-1-pyrrolidinyl)oxy]-2-oxoethyl]-1,3-dihydro-3,3-dimethyl-1-(4-sodiosulfobutyl)-2H-indol]-2-ylidene]-1,3-pentadienyl]-3,3-dimethyl-1-(4-sulfonatobutyl)-3H-indolium. Sulfoindocyanine succinimidyl ester), x-Rhodamine, Pacific Blue and the like can be mentioned as preferred ones.

The term "quencher" means a substance, which acts on the above-described fluorescent dye and reduces or quenches the emission of fluorescence from the fluorescent dye. Illustrative are Dabcyl, "QSY7" (product of Molecular Probes Corporation), "QSY33" (product of Molecular Probes Corporation), Ferrocene and its derivatives, methyl viologen, and N,N'-dimethyl-2,9-diazopyrenium, BHQ, Eclipse, with Dabcyl being preferred.

By labeling a specific position of an oligonucleotide with a fluorescent substance and a quencher substance as above, the fluorescent emission of the fluorescent substance is susceptible to a quenching effect of a quencher.

On a method for amplifying nucleic acid as used in the present invention may be not imposed any limitation, if it serves the achievement of an object of the present invention.

A method for amplifying a nucleic acid as used in the present invention is a method for amplifying in vitro a nucleic acid. It may be a known one or a unknown one. It should encompass, for example, a PCR method, an LCR method (ligase chain reaction), a TAS method, an ICAN method (Isothermal and Chimeric primer-initiated Amplification of Nucleic acids), an LAMP method, an NASBA method, an RCA method, a TAMA method, a WAN method and the like. A PCR method using primer probes or a simple probe is preferable.

The above PCR method can preferably have any system.

It should encompass, for example, a quantitative PCR method, a real-time quantitative PCR method, an RT-PCR method, an RNA-primed PCR method, an Stretch PCR method, a reverse PCR method, an Alu-sequence-using PCR method, a multiple PCR method, a mixed-primer probe-using PCR method, a PNA-using PCR method, and also a method for examining or analyzing a dissociating curve in regard to a nucleic acid amplified by a PCR method.

A "Q probe" or "Qprobe" is a probe proposed by KURATA et al. (Kurata et al., Nucleic Acids Research, 2001, Vol. 29, No. 6, e34.). This probe is a nucleic acid probe for a homogeneous solution system, in which a single-stranded oligonucleotide is labeled with a fluorescent dye. The base labeled with the fluorescent dye is a G or a C, or there is a G or a C at a position 1 to 3 bases apart from a base in a target nucleic acid, said base corresponding to a labeled base and being counted as the $1^{st}$ base.

A labeling portion of an oligonucleotide to be labeled with a fluorescent dye can be an end portion or in its chain. A labeling position thereof can be a sugar moiety, a phosphate moiety or a base moiety. The labeling can be labeled on the 3'-OH group or 2'-OH group of the sugar moiety at the 3'-end, or the 5'-OH group of the sugar moiety obtained by dephosphorylation at the 5'-end. In the phosphate portion, the phosphate group can be replaced with a sulfonate group, or sulfinyl group. The labeling portion is preferably a portion containing a C or a G or their selves, with a portion containing a C being the most preferable.

The present invention comprises four invention, with each comprising further sub-invention.

A novel mixture according to the present invention can be in a liquid, a powder, a tablet, or a capsule; any can be preferably used; and the form is in particular not limited. In the following description, no form of the novel mixture is, therefore, mentioned.

In addition, the following target nucleic acid or an internal standard nucleic acid should, encompass an amplified product until an optional amplification phase (including a stationary phase).

Further, a target nucleic acid should contain a product amplified concurrently in a reaction system from together a target nucleic acid and an internal standard nucleic acid corresponding thereto, its resultant reaction solution, or an one isolated therefrom together with the target nucleic acid and internal standard nucleic acid. In this case, a same probe can be used, or not be used. A nucleic acid-amplification method can be a conventional one as described below.

The nucleic acid probe (a target nucleic acid and/or an internal standard nucleic acid) as used in the present invention is a nucleic acid probe changing its optical character; a nucleic acid probe decreasing or increasing in a fluorescent intensity can be exemplified. For example, exemplified can be the above mentioned Qprobe as one decreasing in a fluorescent intensity, a nucleic acid probe labeled with two dyes related to FRET phenomena as one increasing (Proc. Natl. Acad. Sci. USA, Vol. pp 8790-8794, 1988; U.S. Pat. No. 4,996,143; JP H05-50152A; JP H08-313529A; JP H10-215897A; JP Application H11-292861) and the like.

A) First Invention

The present invention is related to a novel mixture or novel reaction solution (hereinafter, the both together are collectively called simply a "novel mixture".) for assaying one or two or more target nucleic acids, which comprises one or two or more below nucleic acid probes for a homogenous solution system and one or two or more below internal standard nucleic acid or further below internal standard nucleic acid probes:

A) A nucleic acid probe for a homogenous solution system (hereinafter, called "the target nucleic acid probe") having below characteristics:

a) It is formed of a single strand oligonucleotide. It has a length of 10 to 100 bases, preferably 15 to 60 bases, more preferably 20 to 40 bases. It can be oligodeoxynucleotide or an oligoribonucleotide. It can also be a chimeric oligonucleotide.

b) one molecule of it is labeled with one or two or more molecules of fluorescent dyes and with one or two or more kinds of fluorescent dyes at an end portion and/or a base portion in the chain of the oligonucleotide, and at a sugar moiety and/or a phosphate moiety;

c) it can cause the labeling fluorescent dye to change in an fluorescent character on hybridizing with any one of a target nucleic acid and an internal standard nucleic acid;

d) it can hybridize with both a target nucleic acid and an internal standard nucleic acid;

e) it can produce a difference between the amount of a change in a fluorescent character before and after on hybridizing with an internal standard nucleic acid and that on hybridizing with a target nucleic acid;

f) if it is labeled with two kinds or more of fluorescent dyes, it can discriminate each between a target nucleic acid and an internal standard nucleic acid based on a change in an fluorescent character on hybridization;

g) its chain length is preferably the same as that of an internal standard nucleic acid or similar to;

h) its chain length is preferably the same as that of an internal standard nucleic acid probe or similar to.

B) An internal standard nucleic acid:

a) It comprises a single strand oligonucleotide. Its chain length is 40 to 2000 bases, preferably 60 to 500 bases, more preferably 80 to 150 bases. The oligonucleotide can be an oligodeoxynucleotide or an oligoribonucleotide. Those can be a chimeric oligonucleotide; and b) it has a structure different in at least a portion from structure of a target nucleic acid of a region corresponding to the above target nucleic acid probe, and is capable of producing a difference between the amount of change in a fluorescent character produced before and after on hybridizing with the above target nucleic acid probe and one on the hybridization of a target nucleic acid with the above target nucleic acid probe.

C) Internal standard nucleic acid probe, it having the following characteristics:

It has the above characteristics a) to h) of the above target nucleic acid probe, wherein a fluorescent labeling portion and the fluorescent character of a labeled fluorescent dye each are different from the ones of the above target nucleic acid probe;

The present invention relates to a novel mixture, wherein the above target nucleic acid probe, internal standard nucleic acid, and an internal standard nucleic acid as included therein each can have preferably at least any one of the following structures, and each those can preferably have the following relationship.

1) Target Nucleic Acid Probe:

(1) It is at least complementary to a target nucleic acid;

(2) it is complementary to an internal nucleic acid except for at least one or two or more regions;

(3) it has a region wherein the one or two or more region of it are not complementary to a target nucleic acid;

(4) if it is labeled with two or more kinds of fluorescent dyes, the structures of the labeled portions are at least different from each others';

(5) the above structure are a base sequence;

(6) the above base sequence is at least 2 or 3' or more bases as the integral number of a base;

(7) the portions which have complementary structures as mentioned above are labeled with fluorescent dyes;

(8) the portions which have non-complementary structures as mentioned above are labeled with fluorescent dyes;

(9) a fluorescent dye-labeled portion of the above target nucleic acid is a guanine (a G) base portion and/or a cytosine (a C) portion, or a portion wherein a G and/or a C exists in a range near a base of a labeled portion (in a range from the 1st base to the 3rd base to a 3'-end or 5'-end (the labeled base being counted as the $1^{st}$ base)

(10) the portion labeled with a fluorescent dye as mentioned above is a 3'- or 5'-end portion;

(11) the end portion as described above is an end base moiety, a sugar moiety (any one of a 2'- or 3'-OH group of the 3'-end, and a 5'-OH group (being obtainable by dephosphorylation)), and a phosphate moiety (or the phosphate moiety should encompass a sulfonate group or a sulfite group).

(12) the plural probes as described above are different from each other's;

(13) the nucleic acid probe as described above is labeled at least two portions (end portions, base moieties in the chain, sugar moieties, phosphate moieties) with fluorescent dyes having characters different from each other's (hereinafter, called "a doubly-labeled nucleic acid probe");

(13-2) the fluorescent dyes with fluorescent characters different from each other's are fluorescent dyes not producing FRET (fluorescence resonance energy transfer) at two portions;

(13-3) the fluorescent dyes with fluorescent characters different from each other's are fluorescent dyes producing FRET at two portions;

(14) the at least two portions as described in the above (12) are at least two bases; the length as the number of a base between two bases is 1 (one) to 100 bases, preferably 10 to 60 bases, more preferably 20 to 40 bases;

(14-2) two portions with such distance between those that no FRET phenomena occur are labeled with the fluorescent dyes having different fluorescent character as described above;

(14-3) two portions with such distance between those that FRET phenomena occur are labeled with two fluorescent dyes having different fluorescent character as described above;

(15) the base as described in the above (12) is cytosine (hereinafter abbreviated "C");

(16) C's as described in the above (12) are bases of both ends;

(17) the base sequence of the target nucleic acid probe as described above is complementary to a target nucleic acid and an internal standard nucleic acid excluding both base end portions (two portions comprising from the 1st base to the 3rd base in length; the end base is counted as the $1^{st}$ base);

(18) the doubly-labeled nucleic acid as described above is a doubly-labeled nucleic acid probe making at one portion a difference between the amount of a change in a fluorescent character on hybridization with a target nucleic acid and that on hybridization with an internal standard nucleic acid, but not making such a difference at the other portion;

(19) The base sequence of said target nucleic acid probe or said doubly-labeled nucleic acid as described above is at least complementary to a target nucleic acid or an internal standard nucleic acid excluding both end base portions (a base sequence of at least from the 1st to the 3rd base in length; the end base is counted as the $1^{st}$ base);

(20) the base sequence of the target nucleic acid probe or said doubly-labeled nucleic acid probe as described above has a base sequence complementary to a target nucleic acid and/or an internal standard nucleic acid;

(21) if the base of a target nucleic acid corresponding to an end base of a target nucleic acid probe or a doubly-labeled nucleic acid probe is taken as the $1^{st}$ base, the number of G of the corresponding target nucleic acid and internal standard nucleic acid in a base sequence the end portion of a range of the $1^{st}$ base to the $3^{rd}$ base is larger in a target nucleic acid than in an internal standard nucleic acid, or smaller in a target nucleic acid than in an internal standard nucleic acid;

(22) if the base of a target nucleic acid corresponding to both end base of a target nucleic acid probe or a doubly-labeled nucleic acid probe is assumed as the $1^{st}$ base, the number of a G of the corresponding target nucleic acid and internal standard nucleic acid in a base sequence of the end portion in a range of from the $1^{st}$ base to the $3^{rd}$ base is larger in a target nucleic acid than in an internal standard nucleic acid in one end region, and in the other end region smaller in a target nucleic acid than or equal in an internal standard nucleic acid in the other end region; or in one end region smaller in a target nucleic acid than in an internal standard nucleic acid; and in the other end region larger in a target nucleic acid than or equal in an internal standard nucleic acid;

(23) the base of a target nucleic acid corresponding to one end base of a target nucleic acid probe or a doubly-labeled nucleic acid probe is a base other than G and the base corresponding to the other end base is a G;

(24) if any of two bases of a target nucleic acid corresponding to both end bases of a target nucleic acid probe is a G, that of an internal standard nucleic acid is a base other than a G; and if that of a target nucleic acid is a base other than a G, that of an internal standard nucleic acid is a G;

(25) a novel mixture according to the above 1) or 5), wherein, if the base of a target nucleic acid corresponding to both end bases of a target nucleic acid probe or a doubly-labeled nucleic acid probe is assumed as 1 (one), the corresponding base sequence of a target nucleic acid and internal standard nucleic acid in a end base sequence of from the 1st base to the 3rd base is different in one end region, but the same in the other end region;

(26) the nucleic acid probe and doubly-labeled nucleic acid probe as described above are a fluorescence-quenching probe (for example, a Qprobe);

(27) the nucleic acid probe and doubly-labeled nucleic acid probe as described above are a fluorescence-emitting probe;

(27) the doubly-labeled nucleic acid probe as described above is labeled with a quenching dye and a fluorescence-emitting dye;

(28) when the target nucleic acid probe or doubly-labeled target nucleic acid probe as described above hybridizes with a target nucleic acid or an internal standard nucleic acid, the above target nucleic acid probe has a base sequence designed so that at least one G is present in a range of from the $1^{st}$ base to $3^{rd}$ base to the 3' end- or 5' end-direction from the labeled base (the labeled base is counted as the $1^{st}$ base);

(29) the end portion opposite the fluorescent dye-labeling portion as described above is not complementary to a target nucleic acid and/or an internal standard nucleic acid (an optional base sequence of from the 1st base to the 5th base, with a preferable base sequence being of from the 1st base to the 3rd base, wherein an end base is counted in the above number of the base sequence.);

(30) at least one of the both ends as described above can be any of a oligonucleotide, trinucleotide and mononucleotide, wherein these nucleotides may be formed of a deoxynucleotide or riboxynucleotide.

(31) the position of the fluorescent dye-labeling as described above in the end sugar moiety is any one of the OH group of the 5' C of the 5'-end sugar (the OH group being formed by dephosphorylation) and the OH group of the C or 2'C of the 3'-end sugar (the 2'-OH group is in the case of a ribonucleotide);

(32) in the presence of at least one of G and C in two regions of a target nucleic acid, the target nucleic acid probe or doubly-labeled nucleic acid probe as described above is a probe having a base sequence(s) designed so that the base sequence(s) is corresponding to one or two of these regions including a G or a C (corresponding to the above regions), wherein the base sequence is labeled with a fluorescent dye.

A novel mixture according to the present invention comprising, in addition, one or two or more fluorescence-quenching substances capable of quenching the fluorescence of a target nucleic acid probe or a doubly-labeled nucleic acid probe not hybridizing with a target nucleic acid or an internal standard nucleic acid, or one or two or more oligonucleotides labeled with the above substance (hereinafter, called a "quenching substance-labeled probe") in addition to the components of the mixture as, described above.

The novel mixture as described above, wherein the above quenching substance-labeled probe has the following characteristics (1) and/or (2):

Characteristics:

(1) The dissociating temperature of the hybrid complex of a target nucleic acid probe or a doubly-labeled nucleic acid probe and a fluorescent quenching substance-labeled probe is lower than the dissociating temperature of the hybrid complex of a target nucleic acid probe or a doubly-labeled nucleic acid probe and a nucleic acid or an internal standard nucleic acid.

(2) After the hybridization of a target nucleic acid probe or a doubly-labeled nucleic acid probe with a target nucleic acid, and after the hybridization of a target nucleic acid probe or a doubly-labeled nucleic acid probe with a target nucleic acid, a fluorescent quenching substance-labeled probe can hybridize with a probe for a homogenous solution system or a doubly-labeled nucleic acid probe due to the above characteristics (1).

2) Internal Standard Nucleic Acid it has at least one of the following characteristics:

(1) An internal standard nucleic acid is not complementary to a target nucleic acid in one or two or more regions.

(2) An internal standard nucleic acid is not complementary to a target nucleic acid in one or two or more regions.

(3) An internal standard nucleic acid id complementary to a target nucleic acid in all regions.

(4) There is G or C in a portion region of the internal standard nucleic acid corresponding to a fluorescence-labeled portion of a target nucleic acid probe.

(5) There is not a G or a C in a portion region of the internal standard nucleic acid corresponding to a fluorescence-labeled portion of a target nucleic acid probe.

(6) There is not a G or a C in a portion region of the internal standard nucleic acid corresponding to one or two or more fluorescence-labeled portions of a target nucleic acid probe.

(7) There is a G or a C in the portion regions of the internal standard nucleic acid corresponding to one of two or more fluorescence-labeled portions of the target nucleic acid probe; but there is not a G or a C in the portion regions corresponding to another fluorescence-labeled portions of the target nucleic acid probe.

(8) There is a G or a C in a portion region of the internal standard nucleic acid corresponding to any one of fluorescence-labeled portions of a doubly-labeled nucleic acid probe.

3) Relation between Target Nucleic Acid and Internal Standard Nucleic Acid.

(1) In such case that a target nucleic acid probe is complementary to a target nucleic acid at the fluorescent dye-labeled region of the target nucleic acid probe, the target nucleic acid probe is not complementary to an internal standard nucleic acid at the region.

(2) In such case that a target nucleic acid probe is complementary to an internal standard nucleic acid at the fluorescent dye-labeled region of the target nucleic acid probe, the target nucleic acid probe is not complementary to a target nucleic acid at the region.

4) Internal Standard Nucleic Acid Probe

The internal standard nucleic acid probe has at least the same characteristics as that of the above target nucleic acid probe and the same structure, but its fluorescent dye-labeled portion has a structural portion different from that of the above target nucleic acid probe. For example, the fluorescent dye-labeled portion of the above target nucleic acid probe is the 3' end; while that of the internal standard nucleic acid is the 5' end. In contrary to the former, further its relation become contrary in response to this.

B. Second Invention

It is a novel method for assaying a nucleic acid, characterized by assaying one or two or more target nucleic acids by using the above novel mixture according to the first invention. No limitation is imposed on this invention. All a method for assaying a nucleic acid by using the above mixture according to the first invention is within the scope of the present invent.

A target nucleic acid is an optional nucleic acid and in particular not limited. For example, the method can have various modes by the combination of the above probe for a homogenous solution system and the internal standard nucleic acid, and further by the combination of those and the internal standard nucleic acid probe. For example, 1) It is a reaction product amplified by a gene-amplifying method (a product amplified until an optional phase reaching to a stationary phase (any phase of an initial phase, a middle phase and a stationary phase)).

2) It is at least one of a target nucleic acid and an internal standard nucleic acid amplified by a gene amplifying method.

3) It is at least one of a target nucleic acid and internal standard nucleic acid amplified by using a same primer.

The method can have various modes by the combination of the above probe for a homogenous solution system and the internal standard nucleic acid, and further by the combination of those and the internal standard nucleic acid probe. For example, the second invention according to the present invention is divided largely to the following modes.

Incidentally, a specific method for assaying a nucleic acid according to the present invention comprises, any instance, conducting a hybridization in the presence of a target nucleic acid and/or an internal standard nucleic acid; measuring a change in an optical character of a reaction system, with the change being derived from a fluorescent dye of a target nucleic acid probe and/or an internal standard nucleic acid probe; calculating a ratio of the obtained measuring values or a ratio of measured changing ratios of the optical character; and determining a concentration of the target nucleic acid based on the calculated ratios.

Assaying Method A:

The method comprises conducting a hybridization in the presence of one or two or more target nucleic acids and/or internal standard nucleic acids, and determining concentrations of one or plural target nucleic acids.

Assaying Method B:

The method comprises assaying a target nucleic acid by using a nucleic acid probe capable of discriminating a target nucleic acid and an internal standard nucleic acid according to the present invention (a nucleic acid capable of discriminating).

Assaying Method C:

In the above method, this method comprises assaying a target nucleic acid by quenching the fluorescence from a target nucleic acid probe or internal standard nucleic acid probe not hybridizing with an internal standard nucleic acid and a target nucleic acid.

Assaying Method D:

In the above method, this method comprises adding, subsequent to the hybridization, an exonuclease into an assaying system, and measuring a change in an optical character of an assaying system.

The assaying method A will first described.

Assaying Method A:

This method is divided by combining a probe for a homogenous solution system with an internal standard probe, and further divided by combining the combined method with an internal standard nucleic acid probe in the following way.

(1) A method using a mixture comprising the above probe for a homogenous solution system and an internal standard nucleic acid.

This method can be divided by a method for measuring an assaying system to the following two methods.

(2) In the above (1), this method is a method using a doubly-labeled nucleic acid in stead of the above probe for a homogenous solution system.

(3) In the above (1), this method is a method using a mixture comprising an internal standard nucleic acid probe.

Next, the above methods will be described in the above order by illustrating a specific target nucleic acid probe, internal standard nucleic acid, or further an specific internal standard nucleic acid probe. More specifically, these methods will be illustrated in the examples. The examples should not limit the present invention.

Figure 9:
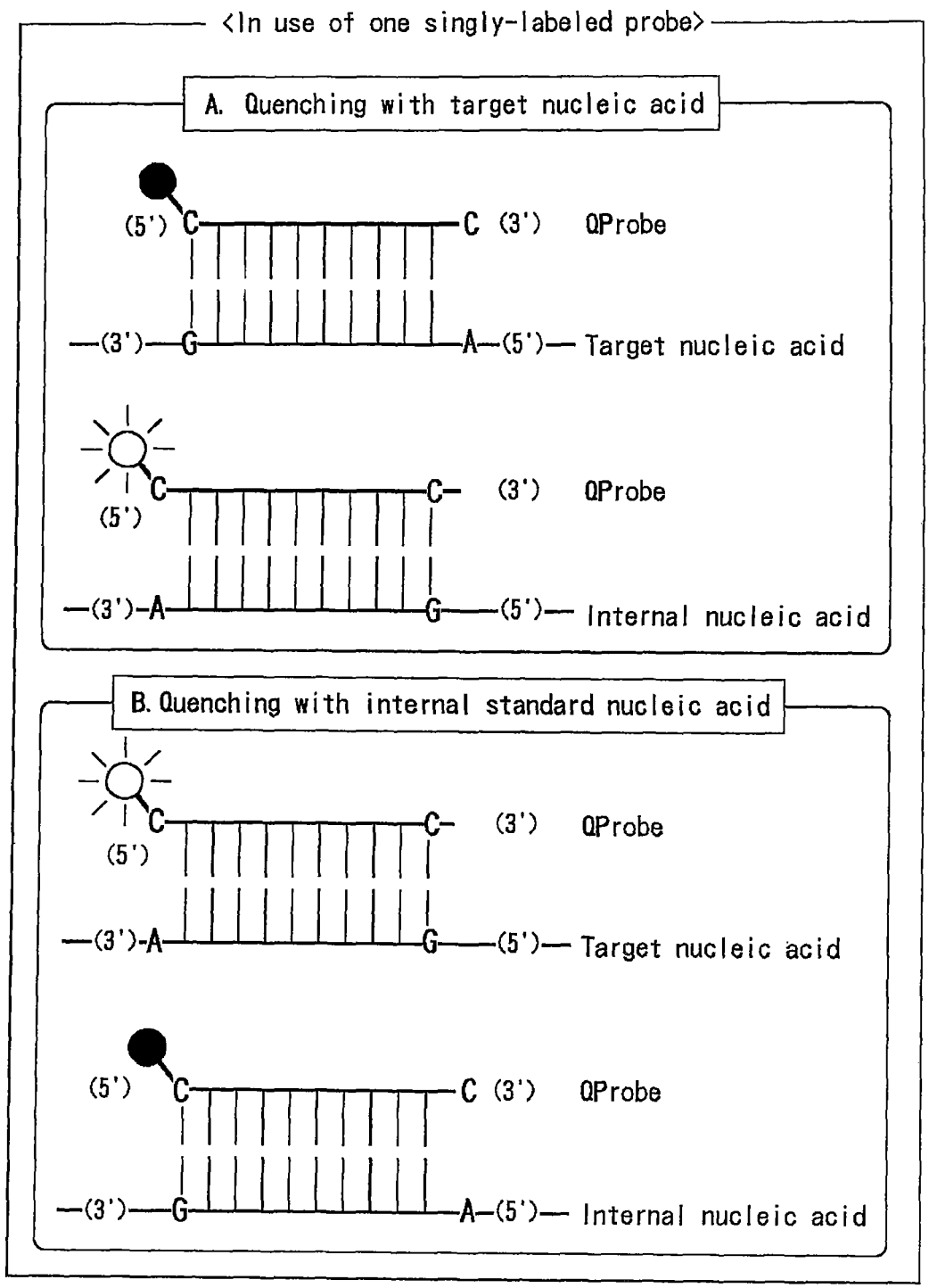
FIG. 9 illustrates an outline of the method for assaying quantitatively a constituent ratio of genes by using a target nucleic acid probe.

Assaying Method 1-1 (see Example 5 and FIG. 9)

Preferable examples will be next described.

FIG. 9 illustrates a method for assaying a nucleic acid according the present invention, in which the simplest labeled nucleic acid and internal standard nucleic acid are used.

The illustrated method adopts a Q probe (called a "Qprobe") as a target nucleic acid probe. Any of the above probes is preferably usable as a target nucleic acid probe in the present invention. The most preferable target nucleic acid probe is a probe in which an end portion opposite a fluorescent dye-labeled portion is not complementary to a target nucleic acid and/or an internal standard nucleic acid (an optional base sequence comprising a range of from the 1st base to the 5th base, preferably of 1 to 3 bases; in this counting an end base is counted as the 1st base).

The simplest target nucleic acid and internal standard nucleic acid are illustrated in FIG. 1, in which a singly-labeled nucleic acid is illustrated as a Qprobe.

Target Nucleic Acid Probe:

In addition, the target nucleic acid probe, the singly-labeled probe, is designed so that a change (decreasing (quenching)) in an optical character (fluorescent emission) of a labeling fluorescent dye occurs on its hybridization with a target nucleic acid. That is, a probe, as a singly-labeled nucleic acid probe, is arranged such that, as a base sequence of the portion of the target nucleic acid capable of hybridizing with the singly-labeled nucleic acid probe, the base corresponding to the fluorescence-labeled end base of this singly-labeled nucleic acid probe is a G or a C; and a base corresponding to non-fluorescence-labeled end base is a base other than a G. On other hand, a base sequence is chosen as a base sequence of the portion of an internal standard nucleic acid capable of hybridizing with the singly-labeled nucleic acid probe such that the base corresponding to the fluorescence-labeled end base of this singly-labeled nucleic acid probe is a base other than a G; and a base corresponding to non-fluorescence-labeled end base is a G or a C. In this case, the base sequence of the singly-labeled nucleic acid probe should be a base sequence complementary to a target nucleic acid and an internal standard nucleic acid except for bases of both ends. The base of a fluorescence-labeled end of the singly-labeled nucleic acid probe should be complementary to the target nucleic acid, but not to the internal standard nucleic acid; the base of a non-fluorescence-labeled end should be contrary to the fluorescence-labeled end. These are in detail indicated in FIG. 9A.

In addition, the singly-labeled nucleic acid probe is possible to design so that, when it hybridizes with an internal standard nucleic acid, a change (decreasing (quenching) in an optical character of a fluorescent dye used for the singly-labeled nucleic acid probe occurs). A base sequence in the region of the internal standard nucleic acid hybridizing with the singly-labeled nucleic acid probe should be arranged so that a base of the internal standard nucleic acid corresponding to a fluorescence-labeled end base of the singly-labeled nucleic acid probe is a G or a C and a base corresponding to a fluorescence-unlabeled end base is a base other than a G. On the other hand, the base sequence in the region of the target nucleic acid hybridizing with the singly-labeled nucleic acid probe should be chosen so that a base of the internal standard nucleic acid corresponding to the fluorescence-labeled end base of the singly-labeled nucleic acid probe is a base other than a G, and a base corresponding to a non-fluorescence-labeled end base is a G or a C. In this instance, a base sequence of the singly-labeled nucleic acid probe should be a base sequence complementary to the internal standard nucleic acid and the target nucleic acid with excluding both end bases; the fluorescence-labeled end base of the singly-labeled nucleic acid probe should be complementary to the internal standard nucleic acid, but not complementary to the target nucleic acid. In the non-fluorescence-labeled end base, the above matters should be contrary. FIG. 9B demonstrates the above description.

Internal Standard Nucleic Acid

A base sequence of the internal standard nucleic acid should preferably be identical to the target nucleic acid except both end bases. In the following description, a preferable internal standard nucleic acid is described.

The base of the internal standard nucleic acid corresponding to the base of a fluorescent dye-labeled portion of the above probe should be designed so as to be complementary to the base of a fluorescent dye-labeled portion of the above probe. That is, when the base of a fluorescent dye-labeled portion of the above probe is a C, the base of the internal standard nucleic acid corresponding to that of the above probe should be a G; or, when the base of a fluorescent dye-labeled portion of the above probe is a G, the base of the internal standard nucleic acid corresponding to that of the probe should be a C. In addition, the base of the internal standard nucleic acid corresponding to the base of a fluorescent dye-unlabeled portion of the probe should be designed so as to be not complementary to the base of the probe. Its base is preferably an adenine (an A) or a thymine (a T).

On the other hand, the base sequence region of a target nucleic acid should be chosen such that, when the base of a fluorescent dye-labeled portion of the probe is a C, the base of a target nucleic acid corresponding to that base is a G; or when the base of a fluorescent dye-unlabeled portion of the probe is a G, the base of the target nucleic acid corresponding to that base is a C; and the base of the target nucleic acid corresponding to the base of a fluorescent dye-labeled portion of the probe is not complementary to the base of the fluorescent dye-labeled portion of the probe.

On the basis of the above description, the number of base-pairs formed between the target nucleic acid probe and a target nucleic acid and GC contents of the probe or the nucleic acid become equivalent to that between the target nucleic acid probe and the internal standard nucleic acid and GC contents of the nucleic acid or the internal standard nucleic acid. As a result, there is almost no difference between the heat stability of the hybridizing complex formed by the target nucleic acid probe and the target nucleic acid and that by the internal standard nucleic acid probe and the target nucleic acid. Owing to those, the both probes is considered to hybridize equally with the target nucleic acid and the internal standard nucleic acid.

The above described pattern is related to a pattern such that fluorescence increases on the hybridization of a singly-labeled nucleic acid probe with an internal standard nucleic acid; while the method having a pattern contrary to the above pattern (namely, a pattern showing decreasing fluorescence upon the hybridization of the singly-labeled nucleic acid with the target nucleic acid) is practicable in the present invention. In other wards, the base sequence of the internal standard nucleic acid should be designed such that, when the base of a fluorescent dye-labeled portion of the singly-labeled nucleic acid probe is a C, the base of the internal standard nucleic acid corresponding to that of the probe is a G; or when the base of a fluorescent dye-unlabeled portion of the probe is a G, the base of the internal standard nucleic acid corresponding to that of the fluorescent dye-unlabeled portion of the probe is a C; and the base of the internal standard nucleic acid corresponding to the base of a fluorescent dye-labeled portion of the probe is not complementary to that of the probe. The pattern is suitably shown in FIG. 8A.

Further, these patterns will be more practically interpreted under using FIG. 9. In FIG. 9A, a Qprobe receives a markedly fluorescence-quenching effect (decreased intensity of fluorescence; hereinafter having the same concept) on hybridization with a target nucleic acid; such effect produces from the presence of a G in a position complementary to fluorescence-labeled (fluorescent dye-labeled) a C. The base sequence of an internal standard gene should be designed so that an adenine (an A) of the gene presents in a position complementary to a C of the 5'-end of a Qprobe; and a G of the gene presents in a position complementary to a C of the 3'-end of a Qprobe. When a Qprobe has hybridized with the internal standard gene, a G does not present in a position complementary to the fluorescence-labeled 5'-end of a Qprobe; as a result, it does not receive any fluorescence-quenching effect. On the contrary, when a Qprobe has hybridized with the target nucleic acid, it receives a markedly fluorescence-quenching effect owing to the presence of a G. A Qprobe can, therefore, specifically detect a target nucleic acid based on a difference of fluorescence-quenching rates.

The change in fluorescence in FIG. 9B is contrary to that of Fig. A. In other wards, a Qprobe receives a markedly fluorescence effect on hybridizing with an internal standard nucleic acid, which effect is caused by the presence of a G of the internal standard nucleic acid in a position corresponding to a C of the fluorescence-labeled 5'-end of the probe; on hybridization with the target gene, a Qprobe is not found to receive any markedly fluorescence-quenching effect because an A is present in a position of the target gene complementary to a C of the fluorescence-labeled 5'-end. A Qprobe can, therefore, specifically detect an amplifying product from the internal standard gene.

Assaying Method 1-2 for Assaying Nucleic Acid (FIG. 2 should be Referred)

It is a method for assaying a nucleic acid by determining a Tm value, which determination is conducted using a below model of a novel mixture selected from the above-described mixtures comprising an internal standard nucleic acid and a target nucleic acid probe. FIG. 2 illustrates specifically the method.

a) Novel Mixture

1) It comprises one or two or more pairs of one or two or more types of the below target nucleic acid probes and one or two or more types of the below internal standard nucleic acids.

The target nucleic acid probe: Any target nucleic acid probe as described above can be used, insofar as it is caused a fluorescent character to change on the hybridization with the internal standard nucleic acid. In particular, it preferably has a portion (including a portion of one base) not complementary to the internal standard nucleic acid in one or two or more portions of the probe other than a fluorescence-labeled portion.

The internal standard nucleic acid: in particular, it is a preferable one having a portion (including a portion of one base) not complementary to the target nucleic acid in one or two or more portions of the internal standard nucleic acid. Further, it is a preferable one having a base-sequence structure (including a structure of one base) such that a region other than a region corresponding to a fluorescence-labeled portion of the target nucleic acid probe is different in one or two or more portion in a region of the internal standard nucleic acid corresponding to the hybridization region of the target nucleic acid probe with the target nucleic acid.

In the present invention, the following instances are preferable.

1) A fluorescent dye-labeled portion of the target nucleic acid is a portion including a C or a G, or these bases (within a portion of from the 1st base to the 3rd base, the labeled is counted as the 1st base).

2) The target nucleic acid probe is a Q probe.

3) The labeled portion of the above 1) is the 3'-end or 5'-end.

b) The Method for Assaying a Nucleic Acid

1) This method is an illustrative method applicable when it is a method for assaying a target nucleic acid by determining a Tm value using the above novel mixture. The method as described in the below 2) is preferable.

2) The method is a method comprising adding one or plural target nucleic acids into the above-described novel mixture; conducting a hybridization; measuring a fluorescent intensity of the hybridizing solution with increasing temperature; and determining the target nucleic acids by the below procedures.

Procedures:

(1) drawing a curve dependent to changed fluorescent intensity measured;

(2) differentiating the resulting curve;

(3) integrating the resulting peak(s) and determining the area(s) of the peak(s);

(4) calculating a ratio(s) of the resulting peak area(s) of the internal standard nucleic acid and the resulting peak area(s) of the target nucleic acid;

(5) multiplying the concentration of the internal standard nucleic acid by said ratio.

Further, the present invention relates to kits comprising the above-described nucleic acid probe and internal standard nucleic acid.

These are hereinafter described with reference of FIG. 2.

On dissociation of the hybridizing complex of a Qprobe and a target nucleic acid, an interaction between a fluorescent dye and guanine is cancelled; the probe becomes to again emit fluorescence. A dissociation curve can be rapidly and easily determined by monitoring fluorescence in continuation with changing temperature; a dissociation peak can be obtained by differentiating the resulted dissociating curve. A peak area ratio of the dissociation peaks varies depending upon a constituent ratio of genes (a existing ratio of target nucleic acids). This method is related to a method for determining a gene-constituent ratio based on the dissociation peaks.

This method comprises a processing step adding an internal standard nucleic acid; the usable internal standard nucleic acid is an internal standard nucleic acid having mutation incorporated into the region hybridizing with a QProbe. When there is no mismatching pair between a QProbe and the target nucleic acid, thereby, no mismatching pair becomes to be present between a QProbe and the internal standard nucleic acid. In this instance, the dissociation between the internal standard nucleic acid and a QProbe occurs in lower temperature than that between the target gene and a QProbe. When a target gene and an internal standard gene are present together, therefore, the dissociation curve becomes such a curve that two curves have been fused. If a difference between a Tm value of a hybridizing complex formed with an internal standard gene and a QProbe and that with an target nucleic acid and a QProbe is enough, the dissociation curve can be completely separated into two (FIG. 2 should be referred). A height ratio of the peaks is highly co-relative to a gene-constituent ratio; a gene-constituent ratio among genes in a system can be determined based on a height ratio of peaks obtained from a dissociation curve. A target gene is, thereby, quantitatively assayed.

In this method, it can be mentioned, as the requirement meeting a preferable internal standard nucleic acid, that dissociation peaks in a target gene and dissociation peaks in an internal standard nucleic acid are separated so that a gene ratio among genes in a system are determined. Therefore, this method is an illustrative method applicable when an internal standard gene meets the above requirement.

This method, like the method for assaying a gene using the below-described two QProbes (a target nucleic acid probe and an internal standard nucleic acid probe), a method for assaying quantitatively a target gene by determining a gene constituent ratio. Thereby, even when the concentration of a probe is lower than a total sum concentration of a target gene and an internal standard gene, it is possible to quantitatively determine correctly a concentration of the target gene insofar as the concentration of an internal standard gene is suitable for determining a gene constituent ratio. On account of this, this method has following features: 1) no requirement for a processing step for diluting a target gene; 2) no requirement for changing a concentration of a probe; it is possible to solve conventional problems.

Assaying Method 2

It is a method using the above-described doubly-labeled nucleic acid probe; it will be illustrated with reference of FIGS. 3, 11, 12, 13, 14 and 15.

Problems for a novel method for assaying a gene by using an internal standard nucleic acid as described above.

i) Only two fluorescent dyes are known as a fluorescent dye such that it is different in fluorescent characteristics such as fluorescence-quenching effect by interaction with guanine, an exiting wavelength, and a fluorescence-emitting wavelength. It is impossible to detect at the same time two or more genes exiting in a homogenous solution system. Because of this deficiency, if two or more genes are asked for detecting, there is no means except for increased number of samples; as a result, a method for assaying a gene using QProbe has been expensive.

ii) Two probes for a homogenous solution are used for a method for assaying a gene using two QProbes, which method is the above-described novel method for assaying a gene. Each probe causes a fluorescence-quenching effect on hybridization with any one of the target gene and the internal standard gene. In addition, a QP probe using in this method can hybridize with a target gene and an internal standard gene without differentiating both genes, on other wards, half portions of the probe hybridizing with a target gene or an internal standard gene causes no fluorescence-quenching effect. As a result, the resulting fluorescence-quenching rate is not great as an expected rate; in particular when a target gene is little in the amount, there are problems such that analyzing errors become greater.

The foresaid problems can be solved by the above described method according to the present invention. That is, the problems have been expected to be capable of being solved by each of the both ends of a QProbe being labeled with one sort of fluorescent dye being different from the other dyes. (see FIG. 3). By using one sort of doubly-labeled probe (called a "Switching probe") obtainable by doubly-labeling both ends of a QProbe with two sorts of dye different from each other, when the probe hybridizes with any of a target gene and an internal standard gene, a fluorescence-quenching effect is caused, namely, any of the hybridized probes causes a fluorescence-quenching effect. Owing to this fluorescence-quenching effect, a fluorescence-quenching rate is theoretically enhanced two times or more as compared with that using two sorts of QProbes; as a result, a detecting sensitivity is possible to improve two times or more (see FIGS. 3, 11, and 13).

This method is specifically not limited insofar as it is a method using a novel mixture comprising the above described doubly-labeled nucleic acid probe and internal standard nucleic acid. Further, it can be a method using the doubly-labeled nucleic acid probe and internal standard nucleic acid described above.

It is, however, preferable to use a novel mixture comprising the below doubly-labeled nucleic acid probe and internal standard nucleic acid, or to use the below doubly-labeled nucleic acid probe and internal standard nucleic acid.

The doubly-labeled nucleic acid probe: Any doubly-labeled nucleic acid probe as described above is usable without any specified limitation. If changes in optical characters of two sorts of fluorescent dyes labeled to the doubly-labeled nucleic acid probe fall within, as one example, the following instances, the probe is preferable.

1) It is a doubly-labeled nucleic acid probe such that, upon hybridization of the above nucleic acid probe with a target nucleic acid, the fluorescence of any one of two labeled dyes is quenched, and the other emits fluorescence; and in this instance, upon hybridization with an internal standard nucleic acid, the fluorescence-quenched dye emits fluorescence and the fluorescence of the fluorescence-emitted dye is quenched. The right drawing of FIG. 3 and FIG. 13 should be referred to. The base sequence of a probe corresponding to this instance can have optional bases as bases of both of the dye-labeled portions, but on other, hand, the base sequence of a target nucleic acid is designed such that a portion of the target nucleic acid corresponding to a portion labeled with any one of both dyes used in the probe includes a G, and that corresponding to a portion labeled with the other dye does not include a G, but includes only an A and/or a T. The base sequence of the internal standard nucleic acid is designed such that it is contrary to that of the target nucleic acid.

2) It is a doubly-labeled nucleic acid probe such that, upon hybridization of the above nucleic acid probe with a target nucleic acid, the fluorescence of both of labeled dyes is quenched, or the both emit fluorescence; and in this instance, upon hybridization with an internal standard nucleic acid, the fluorescence of any one of both of the labeled dyes is quenched, and the other dye emits fluorescence; or in the instance contrary to the above, on hybridization with an internal standard nucleic acid, the fluorescence of both of the labeled dyes is quenched, or the both emit fluorescence; and in this instance, upon hybridization with a target nucleic acid, the fluorescence of any one of both of the labeled dyes is quenched, and the other dye emits fluorescence; See FIG. 13.

In the base sequence of the probe in an instance as above, as an illustrative base sequence, a base of a dye-labeled portion of the probe can be optional; a base sequence in a target nucleic acid side should be designed so that both regions of the target nucleic acid corresponding to both portions labeled with two dyes in the probe include a G, or does not a G. On other hand, a base sequence in the internal standard nucleic acid should be designed so that any one of both of the regions includes a G.

As an additional illustrative base sequence, a base of a dye-labeled portion of the probe can be optional; a base sequence in a target nucleic acid side should be designed so that any one of both regions of the target nucleic acid corresponding to both portions labeled with two dyes in the probe include a G. On other hand, a base sequence in the internal standard nucleic acid should be designed so that both of the regions include a G, or does not a G. See FIG. 13.

In the present invention, such a probe as described above is preferably usable.

Internal standard nucleic acid: The above description of the above doubly-labeled nucleic acid should be referred to.

Incidentally, in this invention also, as a doubly-labeled nucleic acid is a Qprobe preferable. In addition, a characterizing form of the above nucleic acid probe is preferably similar to that in the first invention except the above-described characteristics.

The illustrative method for assaying a nucleic acid is described as follows:

The following instance is a preferable method; this instance imposes no limitation on the present invention.

It comprises: adding one or plural target nucleic acid into the above-described mixture and conducting hybridizing reaction; measuring a change in an optical character from both dyes in the reaction system; calculating a ratio of the resulting measuring values, or a rate of an changed optical character (one example: a fluorescence-quenching rate); and determining a concentration of the target nucleic acid. An illustrative method will be described in examples 6 and 7.

Assaying Method 3

It is a method using a mixture obtained by adding further an internal standard nucleic acid probe into the mixture as described in the foregoing (1). See FIG. 1.

Insofar as the method is a method using a novel mixture containing an internal standard nucleic acid probe in addition to the ingredient in the mixture as described above, any method can be applicable; the following method is preferable.

The method is characterized, in that the method comprises: adding one or plural target nucleic acid into the above-described mixture and conducting hybridizing reaction; measuring a change in an optical character from each dye in the reaction system; calculating a ratio of the resulting measuring values, or a rate of changing in an optical character (a decreasing rate or a emitting rate); and determining concentrations of one or plural target nucleic acids.

The method for assaying a target nucleic acid according to the present invention is shown in FIG. 1, in which it uses a reaction solution prior to a reaction, including the simplest target nucleic acid probe, internal standard nucleic acid probe and internal standard nucleic acid. However, the present invention can not be limited by an illustrative method of FIG. 1.

In FIG. 1, a QProbe is used as a target nucleic acid probe or internal standard nucleic acid probe for simplifying.

The method will be described hereinafter with reference to FIG. 1 by using the simplest target nucleic acid probe, internal standard nucleic acid probe and internal standard nucleic acid. In a method shown in FIG. 1, QProbe A is used as a target nucleic acid probe and QProbe B as an internal standard nucleic acid probe.

Target Nucleic Acid Probe

It is designed such that it hybridizes indiscriminately a target gene (hereinafter, called a "target nucleic acid") and an internal standard gene (hereinafter, called an "internal standard nucleic acid"); and only on hybridization with a target nucleic acid, a change (for example, the figure shows decreasing (quenching)) in an optical character (fluorescence-emission) of dyes used for labeling the probe can occur. The probe is, in this instance, preferably designed such that the end region opposite a labeled portion of the probe is not complementary to a target nucleic acid. That the number of non-complementary bases of the target nucleic acid probe is caused to be equal to that of bases of the internal standard nucleic acid probe, which bases are complementary to the target nucleic acid in a fluorescence-labeled portion of the internal standard nucleic acid is preferable because the thermo-stability of the hybridizing complex between a target nucleic acid probe and a target nucleic acid comes to be identical to that between an internal standard nucleic acid probe and an internal standard nucleic acid.

That is, an fluorescent dye-labeled end portion of the probe is caused to be complementary to a region of the target nucleic acid corresponding to the fluorescent dye-labeled end portion of the probe and is caused to be not complementary to the region of the internal standard nucleic acid corresponding to that of the probe. On other hand, the end portion opposite the fluorescence-labeled portion is caused to be not complementary in the target nucleic acid and to be complementary in the internal standard nucleic acid.

Specifically, a fluorescence-labeled portion of the probe is caused to be a portion containing a G or a C, or to be a G or C self. A base sequence of the region of the target nucleic acid corresponding to the labeled portion of the probe is designed such that the corresponding region is caused to contain a C or a G, to be a C or G self. This designing means that the base of the target nucleic acid corresponding to the labeled base of the probe is not necessarily a C or a G; and at least one base of a C or a G is included within a region (in a range of one base to three bases in a direction of the 5'- or 3'-end apart from the base corresponding to a labeled base of the probe, wherein the corresponding base is counted as the $1^{st}$ base) of the target nucleic acid containing the base corresponding to a labeled base of the probe.

On the other hand, a base sequence of the other end region of the probe should be designed such that the base sequence is caused to be not complementary to a target nucleic acid, but to be complementary to an internal standard nucleic acid. Since this region of the internal standard nucleic acid corresponding to the other end region of the probe has been designed so as to be complementary to a fluorescence-labeled portion of an internal standard nucleic acid probe, the region includes at least one base of a C or a G. Accordingly, the other end region of the target nucleic acid probe includes at least one base of a C or a G, or is a portion of self thereof. The correspondence should be that the region of the internal standard nucleic acid corresponding to the other end region of the probe includes a G or a C, or is a portion of self thereof; that of a target nucleic acid includes a C, or is a portion of C self. On the contrary, when a corresponding region of an internal standard nucleic acid includes a C, or is a portion of self thereof, that of a target nucleic acid should include a G, or should be a portion of G self. These correspondences are shown in FIG. 1.

Internal Standard Nucleic Acid Probe:

Its base sequence should be the same as that of a target nucleic aid probe, wherein a fluorescence-labeled portion should be contrary to that of the target nucleic acid probe as shown in FIG. 1. Further, a fluorescent dye to be labeled should be different from that of the target nucleic acid. It is designed such that it hybridizes indiscriminately a target gene and an internal standard gene; and only on hybridization with a target nucleic acid, changes (for example, the figure shows decreasing (quenching)) in optical characters (fluorescence-emission) of dyes used for labeling the probe can occur. The probe is, in this instance, preferably designed such that the end region opposite a labeled portion of the probe is not complementary a target nucleic acid. That the number of non-complementary bases of the target nucleic acid probe is caused to be equal to that of bases of the internal standard nucleic acid.

Internal Standard Nucleic Acid

It is designed such that it is caused to hybridize indiscriminately a target nucleic acid probe and an internal standard nucleic acid probe; and only on hybridization with an internal standard nucleic acid probe, changes in optical, characters of dyes used for labeling the probe can occur. Insofar as an internal standard nucleic acid meets this requirement, any internal standard nucleic acid with any structure is preferably applicable. For example, the base sequence of the internal standard nucleic acid is preferable to make identical to that of the target nucleic acid except both end bases.

It should be designed such that the base of the internal standard nucleic acid corresponding to the base of a fluorescent dye-labeled portion of an internal standard nucleic acid probe is complementary to the base of the internal standard nucleic acid probe. On the other ward, when the labeled region of the internal standard nucleic acid probe contains a C, or is a portion of C self, the corresponding region of the internal standard nucleic acid contains a, or is a portion of G self; and when the labeled region of the internal standard nucleic acid probe includes a G, or is a portion of G self, the corresponding region of the internal standard nucleic acid contains a C, or is a portion of C self.

It should be designed such that the region of the internal standard nucleic acid corresponding to the base of a fluorescent dye-unlabeled portion of an internal standard nucleic acid probe is not complementary to the base of the internal standard nucleic acid probe. That is, when the unlabeled region of the internal standard nucleic acid probe includes a G, or is a portion of G self, the corresponding region of the internal standard nucleic acid is caused not to contain a C, and is caused to be a portion containing only a G, an A or a T, or to be a portion of each self thereof, preferably being caused to be a portion including only an adenine (a A) and/or a thymine (a T), or to be a portion of each self thereof. On the contrary, when a corresponding region of an internal standard nucleic acid probe contains a C, or is a portion of C self, a corresponding region of an internal standard nucleic acid is caused not to contain a G, and is caused to be a portion containing only a C, an A, a T, or a portion of each self thereof.

By the above designing, the thermo-stability of the hybridizing complex between a target nucleic acid probe and a target nucleic acid comes to be identical to that between an internal standard nucleic acid probe and an internal standard nucleic acid; both probes are expected to be capable of hybridizing with a target nucleic acid and an internal standard nucleic acid indiscriminately.

In the following description, this assaying method will be illustrated with reference to FIG. 1. On hybridization of QProbe A with a target nucleic acid, a G of the target nucleic acid comes at a position complementary to a fluorescence-labeled C (labeled with a fluorescent dye); the fluorescence emission of QProbe A is markedly quenched (a fluorescent intensity is reduced) (hereinafter, meaning the same). A base sequence of an internal standard nucleic acid is arranged such that an adenine (a A) of the internal standard nucleic acid comes at a position complementary to the 5'-end base C of QProbe A; as a result, on hybridization of QProbe A with the internal standard nucleic acid, the fluorescence-emission of Qprobe A is not quenched because G is not present in a position complementary to the fluorescence-labeled 5'-end. On hybridization with the target nucleic acid, the fluorescence-emission of QProbe A is markedly quenched, because G comes at the complementary position: In this way, a QProbe can detect specifically a target nucleic acid based on the difference of quenching rates.

Further, on hybridization of QProbe B with the internal standard, the fluorescence-emission of QProbe B is markedly quenched, because G of the target nucleic acid comes at a position complementary to a fluorescence-labeled 3'-end C; on hybridization of QProbe B with the target nucleic acid, the fluorescence-emission of Qprobe B is not found to be quenched because an A comes at a position complementary to the fluorescence-labeled 3'-end C of the QProbe B. In this way, Qprobe B can detect, on the contrary to QProbe A, specifically a PCR-amplified product from the internal standard nucleic acid.

Method for Assaying Target Nucleic Acid

Since the novel mixture according to the present invention comprises the above-described constituents, the assaying method comprises: adding one or plural target nucleic acid into the mixture and conducting hybridizing reaction; measuring a change in an optical character from the target nucleic acid probe and a change in an optical character from the internal standard nucleic acid probe; calculating a ratio of the resulting measuring values, and determining a concentration of the target nucleic acid by multiplying a used concentration of the internal standard by an obtained calculating value.

That is, each of the above-described QProbe A and QProbe B can hybridize with the target gene and the internal standard gene indiscriminately. Thereby, the hybridization of any of the probes with any of genes relies completely on an existing ratio of genes. On this reason, a ratio between measuring values obtained by measuring changes in optical characters from QProbe A and that from QProbe B becomes to be a constituent ratio between the target nucleic acid and the internal standard nucleic acid.

The novel method for assaying a target nucleic acid is, as described above, a method for determining a gene constituent ratio. Thereby, even when the total sum concentration of a target nucleic acid and an internal standard nucleic acid is higher than a total sum concentration of a target nucleic acid probe and an internal standard nucleic acid probe (such case as that a nucleic acid concentration is higher than a probe concentration), it is possible to determine a constituent ratio of a target nucleic acid and an internal standard nucleic acid insofar as the concentration of an internal standard nucleic acid is suitable for determining a nucleic acid constituent ratio (insofar as a concentration of an internal standard nucleic acid is enough close to a concentration of a target nucleic acid). As a result this method can accurately determine quantitatively a concentration of a target nucleic acid. On account of this, in this method, 1) it is not necessary to dilute a solution containing a target gene, and 2) it is not required to change an additive concentration of a probe, because the additive concentration of a probe can be adjusted at the lowest concentration fallen in a concentration range detectable by an instrument used for fluorescence-detecting. It is concluded that this method has following features: 1) no requirement for a processing step for diluting a target gene; and 2) no requirement for changing a concentration of a probe; it is possible to solve conventional problems.

In an additional aspect of the present invention, there is provided the following probes and kits.

1) One or plural pairs of nucleic acids comprising the above-described target nucleic acid probes and internal standard nucleic acid probes.

2) Kits for assaying a target nucleic acid, comprising one or plural pairs of nucleic acids comprising the above-described target nucleic acid probes and internal standard nucleic acid probes; and one or plural internal standard nucleic acids corresponding to pairs of the nucleic acid probe as described in above 1).

Assaying Method B:

The method has the following two ways.

The method is based on hybridization without discriminating a target gene and an internal standard gene; that any of the probes hybridizes with any of genes relies completely on an existing ratio of genes. Owing to this, for example, it is expected that a constituent ratio of genes can be determined, based on hybridizing ratio between the hybridization of QProbe A with a nucleic acid and the hybridization of QProbe B with a nucleic acid. Fluorescence-quenching is excitingly caused on hybridization of QProbe A with a nucleic acid or on hybridization of QProbe B with an internal standard nucleic acid. On this reason, a ratio between a fluorescence-quenching rate from QProbe A and that from QProbe B is positively proportional to a constituent ratio between the target nucleic acid and the internal standard nucleic acid; as a result, a constituent ratio of genes can be determined based on the ratio, of fluorescence-quenching rates.

The method will be explained below.

Assaying Method 1

It is a novel method for assaying a nucleic acid, wherein the novel mixture according to the present invention comprises any one of the following target nucleic acid probe, doubly-labeled nucleic acid probe, and multiply-labeled nucleic acid probe and the predetermined amount of an internal standard nucleic acid. Hereinafter, these will be called "recognizable nucleic acid probe". The novel mixture in this method comprises one or two or more nucleic acids as described below. In the novel mixture comprising two or more nucleic acids, sorts of dyes, with which each probe is labeled, are different from each others; and the dyes have different optical characters from each others, as described above.

Novel Mixture

It comprised one or two or more nucleic acids and internal standard nucleic acids as described below.

Target Nucleic Acid Probe

The target nucleic acid probe of the present invention is not complementary to a target nucleic acid and an internal standard nucleic acid at one or two or more portions of a fluorescent dye-labeled region.

Doubly-labeled Nucleic Acid Probe

The doubly-labeled nucleic acid probe according to the present invention is not complementary to any one of a target nucleic acid and an internal standard nucleic acid at a labeled portion with any of two dyes used for labeling the doubly-nucleic acid.

The method according to the present invention can, subsequent to determination of an existing ratio of a target nucleic acid and an internal standard nucleic acid, determine correctly a concentration or amount of the target nucleic acid based on the obtained existing ratio.

Multiply-labeled Nucleic Acid Probe

It is a probe to which the described doubly-labeled probe is applied. An A, a C or a G containing portion (preferably C) of region one (1) to region n of a single stranded oligonucleotide (including an end portion, a base moiety, a sugar moiety, or a phosphate moiety of a portion in its chain; n stands 10, preferably 5, more preferably 3.) is labeled with each of dye 1 to dye n, respectively, which each dye can cause a change in an optical character on its hybridization with a target nucleic acid. Sorts of dye 1 to dye n each independently are different fluorescent dyes. In addition, region 1 to region n independently are different regions. The structure of a labeled portion in the probe and the structure of a target nucleic acid corresponding to the probe are like those as described above.

Incidentally, a preferable example of the multiply-labeled nucleic acid probe is a QProbe; further, its preferable labeled portion is a portion of C self or a region containing the portion.

Internal Standard Nucleic Acid

It is a nucleic acid like the internal standard nucleic acid used in the assaying method using a doubly-labeled nucleic acid probe. Further, as described in the above, the structure of its portion corresponding to each of the fluorescent dye-labeled portions of the multiply-labeled nucleic acid probe should be different from that of a nucleic acid. The "different structure" herein means whether or not a structure is complementary to a fluorescent dye-labeled portion of the probe. These structures each have a structure applied correspondingly to the above both structures. In the case of two or more target nucleic acids, two or more internal standard nucleic acids become to be needed correspondingly; the above-described novel mixture of the present invention should comprise two or more internal standard nucleic acids.

Assaying Method

Its method comprises: adding one or two or more target nucleic acids into the novel mixture in this method; conducting hybridization; measuring a change or changing rate (for example, a quenching rate) in an optical character of each fluorescent dye labeled to each probe in the hybridizing system using one or two or more measuring wave length, in that the change is caused by the hybridization of a target nucleic acid or internal standard nucleic acid and a corresponding probe; calculating a ratio between a measuring value in regard to the target nucleic acid and that in regard to the internal standard nucleic acid; and determining one or two or more target nucleic acids on the basis of the obtained ratio because the concentrations of the internal standard nucleic acids have been predetermined.

Assaying Method 2

It is a method based on the determination of a Tm value.

A usable novel mixture may be an one like the mixture as described above.

Assaying Method:

The method is a method comprising adding one or plural target nucleic acids into the above-described novel mixture; conducting a hybridization; measuring a fluorescent intensity of the hybridizing solution with increasing temperature; and determining a existing ratio of the target nucleic acids by the below procedures.

Procedures: (Conducting this Operation in Every Probes)

(1) drawing a curve dependent to a change in an optical character measured;

(2) differentiating the resulting curve;

(3) measuring the height value(s) of a resulting peak(s), or integrating the resulting peak(s) and determining the area value(s) of the peak(s);

(4) subsequent to election of a peak (a referential peak of a target nucleic acid), calculating a ratio(s) of the resulting peak height value(s) or area value(s) of the internal standard nucleic acid to the resulting peak height(s) or area(s) of the target nucleic acid (the peak height value of an other target nucleic acid/the referential peak height value, or the peak area value of another target nucleic acid/the referential peak area value);

(5) calculating a existing ratio of the referential nucleic acid to the comparative nucleic acid;

(6) determining a concentration or amount of the target nucleic acid on the basis of the obtained existing ratio, because the concentration of the internal standard nucleic acid has been predetermined.

The above method will be illustrated using a QProbe.

On dissociation of the hybridizing complex of a Qprobe and a target nucleic acid, an interaction between a fluorescent dye and guanine is cancelled; the probe becomes to again emit fluorescence. Thereby, a dissociation curve can be rapidly and easily determined by monitoring fluorescence in continuation with changing temperature; a dissociation peak can be obtained by differentiating the resulted dissociating curve. A peak area ratio of the dissociation peaks varies depending upon a constituent ratio of genes (a presence ratio of target nucleic acids). This method is related to a method for determining a gene-constituent ratio based on the dissociation peaks.

This method is a method for determining a existing ratio of genes. Thereby, even when the total sum concentration of a target gene and an internal standard gene is higher than a total sum concentration of QProbe A and QProbe B (such case as that a gene concentration is higher than a probe concentration), it is possible to determine a constituent ratio of a target gene and an internal standard gene insofar as the concentration of an internal standard gene is suitable for determining a gene constituent ratio (insofar as a concentration of an internal standard gene is enough close to a concentration of a target gene). As a result, this method can determine accurately and quantitatively a concentration of a target gene.

On account of this, in this method, 1) it is not necessary to dilute a solution containing a target gene, and 2) it is not required to change an additive concentration of a probe, because the additive concentration of a probe can be adjusted at the lowest concentration fallen in a concentration range detectable by an instrument used for fluorescence-detecting. It is concluded that this method has following features: 1) no requirement for a processing step for diluting a target gene; and 2) no requirement for changing a concentration of a probe; it is possible to solve conventional problems.

Assaying Method C:

In the above method, this method comprises assaying a target nucleic acid by quenching the fluorescence from a target nucleic acid probe or internal standard nucleic acid probe not hybridizing with either an internal standard nucleic acid or a target nucleic acid. An object of the present invention is capable of being achieved by using illustrative quenching substances or quenching substance-labeled probes as described below. These are mere examples; these cannot impose any limitation on the present invention. See Example 9.

Quenching substance: Illustrative are the above quenchers. Any one of the illustrative substances can be preferably used. Preferably illustrative are Dabcyl, BH, Eclipse, Elle Quencher.

Quenching substance-labeled probe: Preferably usable is a probe labeled with any one of the above quenchers at a portion of an oligonucleotide (any of a deoxynucleotide body and ribonucleotide body can be usable). Specifically see Example 9. As a labeling portion or position can be preferably usable any portion or position insofar as those can cause a change in an optical character (for example, a fluorescence emission or quenching) of a target nucleic acid probe and/or internal standard nucleic acid probe not hybridizing with a target nucleic acid and/or an internal standard nucleic acid. In particular, there is no limitation in this instance.

Assaying Method D:

It comprises, subsequent to adding an exonuclease into an assaying system of the present invention specifically upon hybridization reaching to equilibrium, measuring a change in an optical character of the assaying system before and after the addition. See Example 10. The hybridization with equilibrium induces a change (for example, fluorescence emission or quenching) in the optical character(s) of a target nucleic acid probe and/or an internal standard nucleic acid. The action of the exonuclease to the probe(s) under such conditions can make a mononucleotide labeled with a fluorescent dye free from the nucleic acid probe(s). The free mononucleotide labeled with a fluorescent dye does not any longer express any specific optical characteristics manifested on hybridization of a nucleic acid probe with a nucleic acid. This method measures that change. The specific method for assaying a nucleic acid will be described in Examples.

Incidentally, preferable conditions for assaying are described in the following.

Conditions: The labeled target nucleic acid probe and/or internal standard nucleic acid probe are (is) not complementary to at least one of the nucleic acid and internal standard nucleic acid in a region containing a fluorescence-labeled portion (the region: a sequence of one base to three bases, preferably of one base).

A novel mixture according to the present invention contains an enzyme; the mixture containing the enzyme is not in a form such that the enzyme is mixed with a mixture comprising a target nucleic acid probe and/or an internal standard nucleic acid probe and an internal standard nucleic acid, but the enzyme is preferably in a form attached at a set to the novel mixture.

Examples of usable exonucleases: (however, the examples impose no limitation on the present invention.)

1) 3'→5' Exonuclease

Exonuclease I (Armersham Biosciene Corp.), Vent DNA polymerase (New England Biolabs), T7 DNA polymerase (New England Biolabs), Klenow Fragment DNA polymerase (New England Biolabs), Phi29 DNA polymerase (New England Biolabs), Exonuclease III (Fermendas).

2) 5'→3' Exonuclease

Taq DNA polymerase, Exonuclease VII (Armersham Biosciene Corp.)

3) Other Usable Enzyme

S1 Nuclease (Armersham Biosciene Corp.), Mung Bean Nuclease (Armersham Biosciene Corp.).

Third Invention

It is an invention wherein the above-described inventions are combined with a nucleic acid-amplifying method. In this invention, a product amplified by the nucleic acid-amplifying method is assayed by using the above method for assaying for assaying a nucleic acid. This method is applicable to any product amplified by a gene-amplifying method. This method comprises, in particular, amplifying one or plural target nucleic acids in a reaction system of the above invention containing one or plural internal standard nucleic acids by a gene-amplifying method; assaying a nucleic acid in the obtained reaction solution or amplified product as a sample by using the above-described nucleic acid-assaying method.

The invention comprises inventions A, B, C and D.

1. Invention A

1) This method comprises, in particular, amplifying one or plural target nucleic acids in a reaction system comprising one or plural internal standard nucleic acids until a stationary phase (including an initial phase, middle phase and stationary phase) by a gene-amplifying method; and assaying a nucleic acid in the obtained reaction solution or amplified product as a sample by a conventionally-known nucleic acid-assaying method.

2) The method comprises; assaying a nucleic acid in the amplified product as described in the above 1) as a sample by a novel nucleic acid-assaying method of the present invention.

3) This method comprises amplifying one or two or more nucleic acids in a reaction system comprising an internal standard nucleic acid of the present invention by a gene-amplifying method; and assaying one or two or more nucleic acids prior to the amplification.

4) In the method for assaying a nucleic acid according to any one of the above 1) to 3), the gene-amplifying method is a nucleic acid-amplifying method using the same primer as a primer of a target nucleic acid and a primer of an internal standard nucleic acid; and the method for assaying a nucleic acid is a method for assaying one or two more nucleic acids prior to an amplification.

5) In the method for assaying a nucleic acid according to the above 3) or 4), the gene-amplifying method is a method using a Qprobe as a primer; and the method for assaying a nucleic acid is a method for assaying one or two more nucleic acids prior to an amplification.

6) In the method for assaying a nucleic acid according to any one of the above 3) to 5), the gene-amplifying method is a method using a primer which is caused an optical character of the primer to increase upon hybridization of the primer with a target nucleic acid and/or internal standard nucleic acid; and the method for assaying a nucleic acid is a method for assaying one or two more nucleic acids prior to an amplification.

This invention is applicable to any product obtained by a gene-amplifying method. In particular, it is preferably applicable to amplified product of a gene, which makes it impossible to assay, that is, the amplified product of a gene amplified until a stationary phase (including a stationary phase).

Invention B

1) It is related to a method for assaying a target nucleic acid, wherein said method comprises: amplifying one or two or more target nucleic acids by a gene-amplifying method in a reaction system comprising one or two or more internal standard nucleic acid, which is used in a method for assaying one or two or more target nucleic acids by a method for determining a Tm value as described in the above; and assaying one or two or more target nucleic acids using the obtained amplified product as a sample by a conventional method.

2) It is a method for assaying one or two or more target nucleic acids prior to the amplification of the target nucleic acids using the above sample by a method for determining a Tm value according to the present invention.

3) It is a method for assaying a target nucleic acid according to the above 2), wherein said method is a method for assaying one or two or more target nucleic acids prior to the amplification of the target nucleic acids.

4) It is a method for assaying a target nucleic acid according to the above 3), wherein said method comprises amplifying a target nucleic acid by using the same primer as a primer of the target nucleic acid and as a primer of an internal standard nucleic acid.

5) It is a method for assaying a target nucleic acid according to the above 4), wherein the using primer is Qprobe.

6) It is a method for assaying a target nucleic acid according to the above 4), wherein the change in an optical character is an increase.

This invention is applicable to any product obtained by a gene-amplifying method. In particular, it is preferably applicable to amplified product of a gene, which makes it impossible to assay, that is, the amplified product of a gene amplified until a stationary phase (including a stationary phase).

Invention C

1) It is a novel method for assaying a target nucleic acid, wherein said method comprise amplifying one or plural target nucleic acids in a reaction system comprising one or plural internal standard nucleic acids as described in invention 2 of the $2^{nd}$ invention; assaying one or two or more target nucleic acids prior to the amplification of the nucleic acids using the obtained reaction solution or amplified product as a sample, or 2) It is a novel method for assaying a target nucleic acid, wherein said method comprise amplifying one or plural target nucleic acids in a reaction system comprising one or plural internal standard nucleic acids as described in invention 2 of the $2^{nd}$ invention; assaying using a novel mixture according to any one of the above 1) to 3) of invention 2 of the $2^{nd}$ invention one or two or more target nucleic acids prior to the amplification of the nucleic acids using the obtained reaction solution or amplified product as a sample, or, 3) It is a novel method for assaying a target nucleic acid, wherein said method comprise amplifying one or plural target nucleic acids in a reaction system comprising the internal standard nucleic acids as described in invention 2 of the $2^{nd}$ invention until a stationary phase (including a stationary phase); assaying using the novel mixture according to any one of the above 1) to 3) of invention 2 of the $2^{nd}$ invention one or two or more target nucleic acids prior to the amplification of the nucleic acids using the obtained reaction solution or amplified product as a sample, or, 4) It is a method for assaying one or plural target nucleic acids prior to the amplification of the target nucleic acids according to any one of the above 1) to 3), wherein said method comprises using the same primer as a primer of the target nucleic acid and as a primer of the internal nucleic acid, or, 5) It is a method for assaying one or plural target nucleic acids prior to the amplification of the target nucleic acids according to the above 4), wherein said primer is a Qprobe, or, 6) It is a method for assaying one or plural target nucleic acids prior to the amplification of the target nucleic acids according to the above 5), wherein the change in an optical character is an increase upon hybridization of the primer with a target nucleic acid and/or an internal standard nucleic acid.

This invention is applicable to any product obtained by a gene-amplifying method. In particular, it is preferably applicable to amplified product of a gene, which makes it impossible to assay.

Assaying Method D, END POINT-assaying Method

Problems of a Gene-assaying Method through an Gene-amplifying Method

The gene-assaying method through an gene-amplifying method is a method comprising amplifying a gene and determining the amplified gene; it is highly sensitive and can assay even a mere-existing gene. Thereby, the method is one of a gene-assaying methods used at present the most popularly. In the gene-assaying method through a gene-amplifying method, various methods are known; and those have problems such as described subsequently. These detailed contents will be mentioned below.

(1) Problems in Conventional Methods i) Problem 1: A Real-time Quantitative PCR Method In a PCR method that is a gene-amplifying method used the most widely at present, the reaction is known to proceed in a exponential function until the amplified product accumulates to a certain level. With increasing an amplified product, however, its amplification efficiency is lowered and reaches to a fixed level (reaching to a plateau); this indicates that the obtained amplified product is constant regardless the initial amount of a gene on enough amplifying reaction. Thereby, the initial amount of a gene is incapable of being assayed based on the amount of the amplified gene product after completed amplification (at an endpoint). This problem is common to a known gene-amplifying method, a PCR method being not restricted.

However, a gene-amplification efficiency of a common gene-amplifying method is constant at an initial phase of the reaction regardless the initial amount of a gene. Therefore, a cycle number of the reaction, in that the amplified product reaches to a threshold, varies on initial amounts of a gene insofar as an amplified product is increased in an exponential function; for example, upon amplification of a predetermined gene diluted in some diluting rates, the cycle number (a CT value) on an amplified product reaching to a threshold is in reverse correlation to an initial concentration of the gene.

This is, as described in the former, due to a fact that an amplification efficiency of an initial phase is fixed regardless various amounts of the gene. A relative equation obtained in thus way is usable as a calculation curve for assaying the unknown amount of a target nucleic acid in an unknown sample. In a usual case, an amplification efficiency of a target gene in an unknown sample is expected to be constant; the initial concentration of the target gene can be determined quantitatively from the above calculating curve, following the determination of a Ct value obtained in a similar manner as above. Accordingly, an initial concentration of a gene can be assayed insofar as an amplified product can be monitored in real time.

The gene-assaying method based on this principal is a real time quantitative PCR method. This method does not requires (1) post-PCR processing steps and (2) to open a reaction tube, so that this method has excellent features such that the assaying is simple and rapid; and the content of the tube is not contaminated with a foreign matter. On the other hand, however, since an amplification process is necessary to monitor in real time, this method embrassed problems such that (1) the apparatus is rendered larger and expensive; and (2) since the method is a method based on an assumption that the amplification efficiency of the gene used for preparing a calculation curve is the same as that of the gene in an unknown sample, thereby, if there is an inhibitor against a gene amplification in an unknown sample, this assumption is capable not to be established, that is, it is difficult to obtain an appropriate value always in this method; (3) since the amplification process is necessary to monitor in real time, one assaying instrument comes to be occupied during assaying. Therefore, its sample-treating power is naturally limited.

ii) Problem 2 in a Conventional Method: a Competitive PCR Method

As a method for assaying a target nucleic acid in high sensitivity, a competitive PCR method is known commonly. This method comprises: adding a primer for amplifying a target gene and the target gene of the predetermined amount (called an internal standard gene) for being amplified by the same primer as in the target nucleic acid into a reaction system; amplifying at the same time together the target gene and internal standard nucleic acid; subsequent to completed amplification, isolating and quantitatively determining the amplified product from the target gene and the amplified product from the internal standard gene by using an electrophoresis and the like; calculating a ratio of the amplified products (the amplified product from the internal standard gene/that from the target gene); and determining a concentration of the target gene by multiplying the amount of the internal standard gene added at the start of amplification by the obtained ratio, because the amplification efficiency of the target gene and that of the internal gene is expected to be the same owing to the amplification using the same primer as a primer for the target gene and as that for the internal standard gene.

This method is difficult to be affected by an amplification inhibitor because a target gene and an internal standard gene are amplified in the coexistence thereof; the reliance on the obtained determining value is high (its cause: for example, even if the inhibitor is present in a assaying system, an amplification efficiency is at all lowered likely in regard to a target gene and a internal standard gene; the existing inhibitor does not affect a ratio of amplified products; as a result, an accurate determining value is obtainable in the competitive PCR.). The characteristics can be mentioned such that the instrument for assaying is comparatively simple and non-expensive.

However, in this method, problems are pointed out such that (a) subsequent to completed gene-amplification, the amplified product is necessary to assay, so that it results in troublesome and time-expensive operation; (b) on the determination of an amplified product, a reaction tube is necessary to be open, and owing to the opening, the reaction solution has a possibility of contamination with a foreign amplified product; and (c) the operation of this method is troublesome and is difficult to be automated, so that its sample-treating power is lower.

iii) Problem 3 in Conventional Method: an Real Time Competitive PCR Method.

The real time competitive method is a method for assaying an initial concentration of a target gene prior to the amplification of the target gene, wherein it is an improved competitive PCR method and comprises: conducting an amplification of a target gene and an internal gene in the coexistence thereof using a TagMan probe, a QProbe or the like; monitoring at the same time in real time an amplified product from the target gene and an amplified product from the internal standard gene; and determining an initial concentration of a target gene prior to the amplification of the target gene based on the fluorescent signal amount from each the amplified products from the target gene and internal standard gene.

This method embraces excellent features such that it does not requires (1) post-PCR processing steps and (2) to open a reaction tube, and (3) further it is, however, difficult to be affected by an inhibitor because of a competitive method. There are problems like the real time quantitative PCR method in this method such that (i) the apparatus usable for assaying is larger and expensive, and (ii) its sample-treating power is lower, because it is required in this method to monitor at the same time in real time an amplified product from an internal standard gene and that from a target gene. The problems as described above are summarized in the following table. The conventional gene-assaying method is recognized to have some problems.

TABLE 1

Problems in conventional gene-assaying methods

| Problems | Real time Quantitative PCR method | Competitive PCR method | Real time Competitive PCR method | Preferable method |
|---|---|---|---|---|
| Rapidity and simplicity of operation | o | x | o | o |
| Prevented contamination with amplification product | o | x | o | o |
| Affection by inhibitor | | o | o | o |
| Expensiveness of apparatus | x | o | x | o |
| Sample-treating power | x | x | x | o | o: Meeting for requirement
x: Non-meeting for requirement

Incidentally, the above described gene-assaying methods are applicable to any gene-assaying methods other than a PCR method such as an NASBA method, an LAMP method, an RCA method, an ICAN method; the methods are at present applied to many gene-determining method through various gene-amplifying method. These methods embraces problems at all common to gene-amplifying methods; even in any gene-assaying method through any gene-amplifying method, the above-described problems are desired to be solved.

(2) Strategy for Solving these Problems

As described above, it is possible to assay an initial concentration of a target gene prior to the amplification of the target gene based on a ratio of an amplified product from a target gene and that from an internal standard gene. If this ratio of amplified products are capable of being assayed in a rapid and simple way without opening a reaction tube after completed gene-amplification, (1) it does not require a PCR post processing step and can simply, easily and rapidly assay a target gene; (2) it is not needed to open a gene-amplifying reaction tube, so that it does not have any risk of contamination with foreign amplified products; (3) the assay is difficult to be affected by inhibitors because the method is a competitive method; (4) since a gene-amplifying processing-step and a detecting processing step of a amplified product can be completely divided, a large quantity-sample becomes to be capable of being treated, so that a sample-treating power can be conveniently and non-expensively improved (for example, subsequent to the gene-amplification by using plural non-expensive PCR-apparatuses not having any fluorescence-measuring function, it comes to be possible to treat large quantitative-samples by analyzing obtained data in order, for example, even using only one fluorescence-measuring instrument); 5) it is possible to assay a target gene by using a markedly simple and non-expensive measuring instrument because the amplifying processing of a nucleic acid is not necessary to monitor in a real time way and the measuring instrument is not requisite for having a thermally-cycling function indispensable to a PCR, so that it is possible to assay a gene by a very concise and non-expensive instrument. This gene-assaying method is expected to be capable of becoming an excellent gene-assaying method with such characteristics as above.

A conventional competitive PCR method makes it possible to determine a ratio of amplified products at an end point, but a reaction tube is necessary to open; so the ratio is capable of being rapidly determined. A real time competitive PCR method, being conventional like the above method and using a fluorescence-labeled probe, does not require to open a reaction tube and is capable of detecting rapidly an amplified product. A ratio of fluorescent signals obtained using a conventional fluorescence-labeled probe in that method, however, does not always reflect usually a quantitative ratio of amplified products; namely, a regional gene reflecting correctly it is limited. In order to determine a ratio of amplified products, each of amplified products requires to be detected in a regional gene where a fluorescent signal ratio is quantitatively proportional to an amplified product ratio. Thereby, a real time competitive PCR method has to be always monitored. As stated above, no method is present until now for determining an amplified product ratio at an endpoint and rapidly with closing a reaction tube.

In view of the above situation, the inventors have proceeded to examine those problems to lead the discover of a novel method enabling it to determine an amplified product ratio at an end point. This invention is related to a novel method for assaying a gene and a novel nucleic acid probe usable therefore. In the following description, those details will be described.

i) An End Point Assaying Method for a Gene Using a QProbe

<Specific Detection of a Target and Internal Standard Nucleic Acid by a Qprobe>

It is an object of certain embodiments of the present invention to provide with a method for detecting an amplified product using the above described doubly-labeled QProbe (a Switching probe) or two QProbes. This description is an embodiment of a determining method using a Switching probe. The Switching probe has features such that (1) the base of each of both ends of the probe is a C, and (2) the both ends are labeled with dyes having colors different in fluorescent emission. The base sequence of a target nucleic acid is designed such that a G is present at a position complementary to a C of the 5'-end of the Switching probe, and an A is present at a position complementary to a C of the 3'-end; on the other hand, in the base sequence of an internal standard gene, the above G is replaced by an A, and the above A by G. Under such a situation, on hybridization of the Switching probe with an amplified product amplified from the internal standard gene, the absence of a G at a position of the amplified product corresponding to its 5'-end does not result in a markedly fluorescence-quenching effect in the dye labeled at its 5'-end; the presence of G complementary to its 3'-end does result in.

On the other hand, on hybridization with an amplified product from the target gene, the presence of G at a position of the amplified product corresponding to its 5'-end results in a markedly fluorescence-quenching effect in the dye labeled at its 5'-end; the absence of G complementary to its 3'-end does not result in. In conclusion, each of the amplified products comes to be capable of specifically being detected by the observation of fluorescence-quenching of any dye labeled at any the both ends.

<Features of Internal Standard Gene>

The base sequence of the internal standard gene has features such that (1) the internal standard gene is capable of be amplified by using a primer common to that of a target gene, (2) a GC content of a target gene is the same as that of the internal standard gene, (3) a length of the base sequence of a portion of the internal standard gene completely complementary to the target gene on hybridization with an amplification product amplified from the target gene is the same as that of the target gene complementary to the internal standard gene on hybridization with an amplification product amplified from the internal standard gene, and (4) a base sequence of the target nucleic acid is the same as that of the internal standard gene except the bases complementary to both ends of a QProbe.

Based on the above description, it is considered that there is no difference between an affinity of the Switching probe to an amplification product from a target gene and that from an internal standard gene. In conclusion, a Switching probe can hybridize at random with an amplification product from a target gene and that from an internal standard gene without differentiating those; a ratio between Switching probe binding to an amplification product from a target gene and Switching probe binding to that from an internal standard gene is completely identical to a ratio of an amplification product from the target gene and that from the internal standard gene. Thereby, Based on a ratio between fluorescence-quenching rates of the two dyes labeled to both ends of the Switching probe, a ratio of amplification products can be determined.

In addition, it is understood that a gene-amplification rate is the same in a target gene and internal standard gene because (1) a primer of a target gene and internal standard gene is common, (2) a GC content of a target gene is completely the same as that of the internal standard gene, and (3) the base sequences of a target gene and a internal standard gene are the same except that two portions are different. Further, based on the above (2) and (3), no bias generated by re-bonding of amplification products could occur. Therefore, a constituent ratio of genes comes to be capable of keeping having a starting ratio. However, as requirements for an internal standard gene's presence in an assay system, the subsequent two matters will be described: (1) a starting gene ratio prior to gene-amplification is kept in any phase of the amplification (an amplification efficiency of an internal standard gene is the same as that of a target gene.), (2) a probe making use is capable of hybridizing at random with an amplification product from a target gene and that from an internal standard gene without differentiating those. Insofar as an internal standard gene meets these requirement, an internal standard gene may or may not be required to have the above features.

As described above, an amplification product can be quantitatively determined based on fluorescence-quenching rates of two dyes labeled to the both ends of a Switching probe.

From the above description, a ratio of amplification products can be quantitatively determined by using an internal standard gene and a Switching probe, wherein said determination can be rapidly and simply carried out at an end point without opening a reaction tube; many samples can be treated.

A method for assaying quantitatively a gene is a method comprising amplifying a target gene; then determining a ratio of amplification products from a target gene and an internal standard gene; and making quantification of the target gene. Insofar as a method for amplifying a gene is capable of amplifying together a target gene and internal standard gene with keeping a starting gene-constituent ratio, the method is applicable to any method for amplifying a gene regardless of its sort. Thereby, this method is applicable to an LAMP method, an RCA method, an ICAN method and the like, and further, a method for amplifying a gene other than a PCR method.

ii) End Point Gene-determining Method by a Dissociation Curve Analysis Method Using a QProbe.

As mentioned above, a gene-constituent ratio can be determined by analyzing a dissociation curve obtainable by a QProbe; this method is expected to be applicable to a competitive gene-assaying method through a gene-amplifying method.

An internal standard gene usable in this method should be a probe such that a mutation is inserted into a portion of said probe capable of hybridizing with a QProbe. Subsequent to completed amplification of a gene, a dissociation curve is prepared of the obtained amplification products using the QProbe, followed by preparation of dissociation peaks based on the obtained dissociation curve. A gene-constituent ratio can be determined based on a peak-height ratio of the dissociation peaks because the peak-height ratio is highly co-relative to a gene-constituent ratio. It becomes possible to determine a concentration of a target gene, subsequent to co-amplification of both of an internal standard gene of a predetermined concentration—the gene-amplification efficiency of the internal standard gene being the same as that of the target gene—and the target gene—using various gene-amplification method, by the determination of a ratio of an amplification product from a target gene to an amplification product from the internal standard gene.

In this method, as requirements for an internal standard gene, two requirements can be mentioned such that (1) a starting gene ratio prior to gene-amplification is kept in any phase of the amplification (an amplification efficiency of an internal standard gene is the same as that of a target gene.), and (2) a dissociation peak derived from a target gene are enough separated from a dissociation peak derived from an internal standard gene so that a gene-constituent ratio can be determined. Insofar as an internal standard gene meets these requirement, an internal standard gene is not always required to have the above features.

Insofar as a method for amplifying a gene is capable of amplifying together a target gene and internal standard gene with keeping a starting gene-constituent ratio, the method is applicable to any method for amplifying a gene regardless of its sort. Thereby, this method is applicable to an NASBA method, an LAMP method, an RCA method, an ICAN method and the like, and further, a method for amplifying a gene other than a PCR method.

D. 4$^{th}$ Invention

This invention is a method for determining accurately a target nucleic acid using a measuring value obtained by the methods of the present invention. The details will be described in Examples 8 and 11.

EXAMPLES

In this examples, various nucleic acid probes, internal standard nucleic acids, and target nucleic acids are used as an oligodeoxynucleotide, unless otherwise specifically indicated.

In various nucleic acid probes, an fluorescence-labeled portion or position is the 5'-OH group of a sugar of the 5'-end in regard to the 5'-end (the group is obtainable by dephosphorylation); on the other hand, the 3'-OH group of a sugar of the 3'-end in regard to the 3'-end:

Example 1

A novel mixture comprising two QProbes and a novel method for assaying a gene making use thereof.

Novel Mixture

The novel mixture having the following composition was prepared.

The following QProbe A (a QProbe for detecting a target gene): 200 nM;

the following QProbe B (for detecting an internal standard gene): 200 nM;

the following internal standard nucleic acid: the ones having each of the following concentrations were prepared:

a) 1/10, 1/5, 1/2, 4/5, and 9/10 of 200 nM b) 1/10, 1/5, 1/2, 4/5, and 9/10 of 800 nM;

Buffer composition: 10 mM Tris-HCl buffer (pH: 8.3), KCl: 50 mM, MgCl$_2$: 1.5 mM Novel Assaying Method (1) Experimental Method It is examined whether or not a ratio between genes existing a system is capable of being determined using the above mixture added with a target gene and using two QProbes. In the experiment after DNA solutions with varied ratios between a target gene and an internal standard gene had be prepared, and therein added with the QProbe for detecting a target gene and the QProbe for detecting an internal standard gene, a fluorescent measurement was implemented. The fluorescent measurement was conducted at 60° C. and 95° C. (the measuring values at 60° C. were those on hybridization of the probe with a target gene; the measuring values at 95° C. were those on complete cleavage of the hybrid complex of the probe and the target gene). Incidentally, the measuring values at 95° C. were taken as a reference so as to determine a fluorescence-quenching rate. In addition, a relation of a ratio of the fluorescence-quenching rates of the each probes and a existing ratio of the target gene and the internal standard gene was examined; it was examined whether or not a gene existing ratio could be determined based this relative equation.

Detailed experimental conditions were indicated in the following.

(2) Experimental Conditions

Target Gene and Internal Standard Gene

Target gene and internal standard gene: oligonucleotides were used.

Synthesis of oligonucleotide: by relying custom synthesis services (Espec oligoservices Inc.).

Base sequence of target gene: 5'-AGTTC CGGAA AGGCC AGAGG AG-3'

Base sequence of internal standard gene: 5'-GGTTC CGGAA AGGCC AGAGG AA-3'

Total final concentration as combined of internal standard gene and target gene: 200 nM, 800 nM (target: internal standard=9:1, 4:1, 1:1, 1:4, 1:9).

QProbe

Synthesis: by relying custom synthesis services (Espec oligoservices Inc.).

Sequence: 5'-CTCCT CTGGC CTTTC CGGAA CC-3'

Dye: the QProbe A (a Qprobe for detecting a target gene) was in fluorescence labeled with BODIPY FL (Molecular probes Inc., D-6140); the QProbe B (a QProbe for detecting an internal standard gene) was labeled with TAMRA (Molecular probes Inc., C-6123).

Final concentration of each QProbe: 200 nM (as a total concentration: 400 nM)

Buffer: 10 mM Tris-HCl buffer (pH: 8.3), KCl: 50 mM, $MgCl_2$: 1.5 mM.

Used apparatus: fluorescence measurements were carried out by a fluorometer, LS50B (PerkinElmer Inc.) with an temperature-controlling instrument (Inc.); the measurements were conducted at 480 nm excitation wavelength and 520 nm fluorescence wavelength for the QProbe A, and at 550 nm excitation wavelength and 580 nm fluorescence wavelength for the QProbe B.

Fluorescence measurements on hybridization were conducted 60° C. A fluorescent intensity at the temperature (95° C.) as a reference, the temperature completely de-hybridizing from a probe; fluorescent quenching rates were determined based on the following equation.

A fluorescent quenching rate (%)=(1−($F60/F95$)/(only $F60$ probe/only $F95$ probe))×100, wherein F60: a fluorescent intensity value at 60° C. in presence of a target gene;

F95: a fluorescent intensity value at 95° C. in presence of a target gene;

Only F60: a fluorescent intensity value at 60° C. in absence of a target gene

Only F95: a fluorescent intensity value at 95° C. in absence of a target gene.

(3) Experimental Results and Discussion

Figure 5:
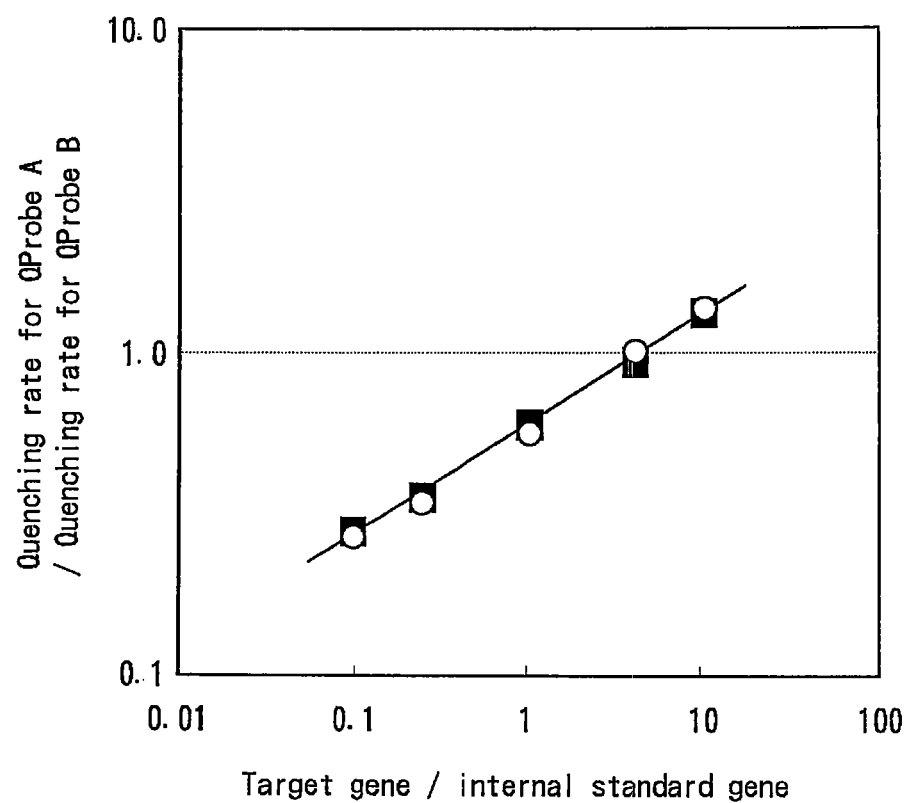
FIG. 5 illustrates an outline of the relation of a fluorescence-quenching ratio and a constituent ratio of genes.
  ○ total gene amount=200 nM, ■ total gene amount=800 nM

FIG. 5 illustrates the experimental results. On the basis of the graphs, it was cleared that a constituent ratio of a target gene/an internal standard gene was highly correlative to a ratio of QProbe A quenching rate/a QProbe B quenching rate. This method was, thereby, suggested to enable a target gene to be assayed.

Even when the total sum amount of a target gene and an internal standard gene was more than the additive amount of a probe (800 nM), the above co-relation was observed also like when less (200 nM) than the additive amount; it is suggested that this method could be determined accurately and quantitatively. Based on the above findings, it is suggested that this method is a method having features such that (1) a processing step for diluting a gene is not necessary; and (2) it is not necessary to make a concentration of a probe vary.

Example 2

2-2 Screening of Novel Dye Capable of Quenching Fluorescence due to its Co-reaction with a Guanine (1) Experimental Method A probe was prepared in which said probe was labeled at a C of a sugar of the 3'-end with a dye to be screened. A fluorescence-quenching rate was assayed by making the prepared probe hybridize with a corresponding chain in a solution.

Experimental Procedures (2) Experimental Conditions

Target Gene

Target gene: an oligo DNA was used.

Synthesis of oligonucleotide: by relying custom synthesis services (Espec oligoservices Inc.).

Base sequence of target gene: 3' ggggg ggggg ggAAAAAA5'

Base sequence of internal standard gene:

Final concentration: 320 nM.

Probe

Synthesis of oligonucleotide: by relying custom synthesis services (Espec oligoservices Inc.).

Base sequence: 5'CCCCC CCCCC CCTTT TTT3'

Dye: PacificBlue (2-Oxo-6,8-difluoro-7-hydroxy-2H-1-benzopyran-3-carboxylic acid, P-10163), TET (2',4,7,7'-tetra-chlorofluorescein, C-6166), TBSF (C-6166), HEX (2',4,4',5',7,7'-hexachlorofluorescein, T-20091), and R6G (C-6127) were tested.

Final concentration: 40 nM.

Buffer: 10 mM Tris-HCl buffer (pH: 8.3), KCl: 50 mM, $MgCl_2$: 1.5 mM.

Used Apparatus

Fluorescent measurements were conducted by a fluorometer, LS50B (PerkinElmer Inc.) with a temperature-controlling instrument (PerkinElmer Inc.). Conditions for fluorescent measurements were determined by measuring maximum excitation wavelengths and maximum fluorescence wavelengths of each dyes using LS50B. In order to fluorescent quenching rates, measurements were conducted by using the obtained maximum excitation wavelength and maximum fluorescent wavelength. The maximum excitation wavelengths and maximum fluorescent wavelengths of each dyes were shown the description of the below result section. The slit width to measure was 5 nm in both excitation and fluorescent wavelengths.

Figure 8:
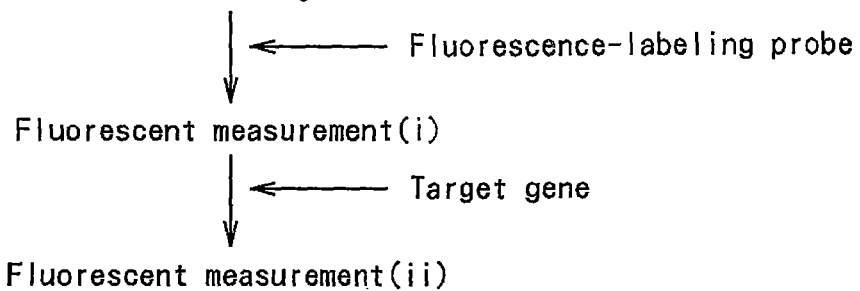
FIG. 8 illustrates the experimental procedures in Example 2

FIG. 8 indicates the experimental procedures. The fluorescent measurement was conducted at 35° C.

The fluorescent quenching rate was determined by the following equation.

Fluorescent quenching rate (%)=(measuring value ($i$)−measuring value ($ii$))÷measuring value ($i$)×100

(3) Experimental Results and Discussion

As ascertained from the below Table, fluorescent quenching was confirmed in all dyes tested. Specifically the fluorescent quenching was marked in PacificBlue (2-Oxo-6,8-difluoro-7-hydroxy-2H-1-benzopyran-3-carboxylic acid) and R6G; the fluorescent quenching rates were higher in those than in dyes known so far. Further, PacificBlue, (its implement unknown), R6G (its implement unknown), BODIPY FL, 4,4-difluoro-5,7-dimethyl-4-bora-3a,4a-diaza-s-indacene-3-propionic acid (its implement known) and TAMRA, Carboxytetramethylrhodamine (its implement known) each were different in fluorescent character thereof; by using four probes labeled with the above dyes, four genes being present in the same could be detected concurrently.

TABLE 2

Relation between fluorescent dye and quenching rate thereof

| | Fluorescent dye | Fluorescence-quenching rate (%) | Maximum excitation wavelength (nm) | Maximum emission wavelength (nm) |
|---|---|---|---|---|
| Unknown use of dye | PacificBlue (P-10163) | 94.0 | 395 | 450 |
| | TET (C-6166) | 56.6 | 515 | 530 |
| | TBSF (C-6166) | 86.5 | 520 | 540 |
| | HEX (T-20091) | 68.3 | 530 | 542 |
| | R6G (C-6127) | 93.1 | 517 | 543 |
| Known use of dye | BODIPY FL (D-6140) | 91.8 | 499 | 522 |
| | TAMRA (C-6123) | 89.2 | 547 | 579 |

Example 3

2-3 Method for Assaying a Gene Using a Switching Probe

Novel Mixture

The novel mixture having the following composition was prepared.

The below Switching probe: 400 nM;
the following internal standard nucleic acid: the ones having the following concentrations each were prepared:
(a) 1/10, 1/5, 1/2, 4/5, and 9/10 of 600 nM
Buffer composition: 10 mM Tris-HCl buffer (pH: 8.3), KCl: 50 mM, MgCl$_2$: 1.5 mM.

In addition, in order to verify the experimental data obtained by using the Switching probe, a novel mixture was prepared by replacing the following QProbe A and QProbe B for the Switching probe in the above reaction solution The following QProbe A (for detecting a target gene): 200 nM;
The following QProbe B (for detecting an internal standard gene): 200 nM.

Novel Assaying Method

A target gene was assayed by adding the target gene in the above novel mixture. Further, the fluorescent quenching rates obtained by using the Switching probe and the fluorescent quenching rates obtained by using two QProbe were compared.

(1) Experimental Method

It was examined whether or not the existing ratios of target genes added in the novel mixture could determined even using the Switching probes like using two QProbes. In addition, the comparison between the fluorescent quenching rates obtained on making use of a Switching probe and those obtained on making use of two QProbes was conducted.

Detailed experimental conditions are shown in the following.

(2) Experimental Conditions

Target Gene and Internal Standard Gene

Target gene and internal standard gene: oligonucleotides were used.

Synthesis of oligonucleotide: by relying custom synthesis services (Espec oligoservices Inc.).

Base sequence of target gene: 5'-TTTAG ATGAC TGACT GACTG ACTGA CGAGA TTT-3'.

Base sequence of internal standard gene: TTTAG ATGAC TGACT GACTG ACTGA CGAGG TTT-3'.

Total final concentration as combined of internal standard gene and target gene: 600 nM (target: internal standard=9:1, 4:1, 1:1, 1:4, 1:9).

QProbe

Synthesis: by relying custom synthesis services (Espec oligoservices Inc.).

Base Sequence and Structure of Switching Probe

BODIPY FL-5'CCTAC TGACT GACTG ACTGA CTGCT CC3'-TAMRA

Base Sequence and Structure of QProbe

<QProbe A (for detecting a target gene)
BODIPY FL-5'CCTAC TGACT GACTG ACTGA CTGCT CC3'

<QProbe B (for detecting an internal gene)
5'CCTAC TGACT GACTG ACTGA CTGCT CC3'-TAMRA Incidentally, used fluorescent dyes were like those of Example 1.

Final concentration: 400 nM (400 nM as a total sum in making use of two QProbes)

Buffer: 10 mM Tris-HCl buffer (pH: 8.3), KCl: 50 mM, MgCl$_2$: 1.5 mM.

Used apparatus, used instrument, assaying conditions, and method for determining a fluorescent quenching rate were like those of Example 2-1

(3) Experimental Results and Discussion

Figure 6:
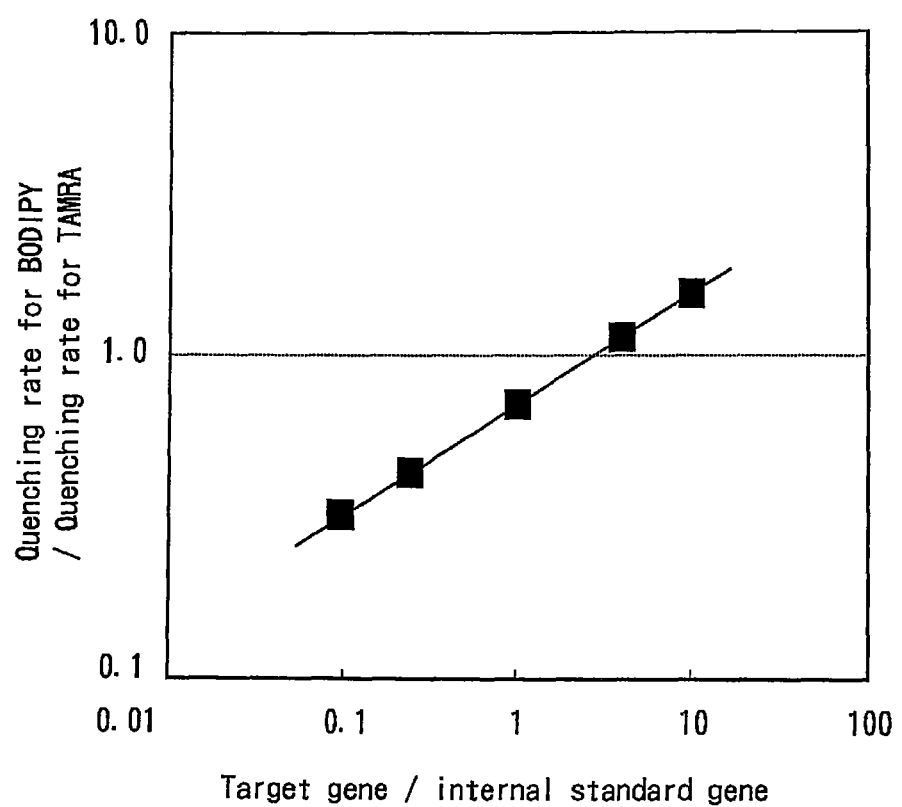
FIG. 6 illustrates the relation of a fluorescence-quenching ratio and a constituent ratio of genes (in using a switching probe).
Figure 7:
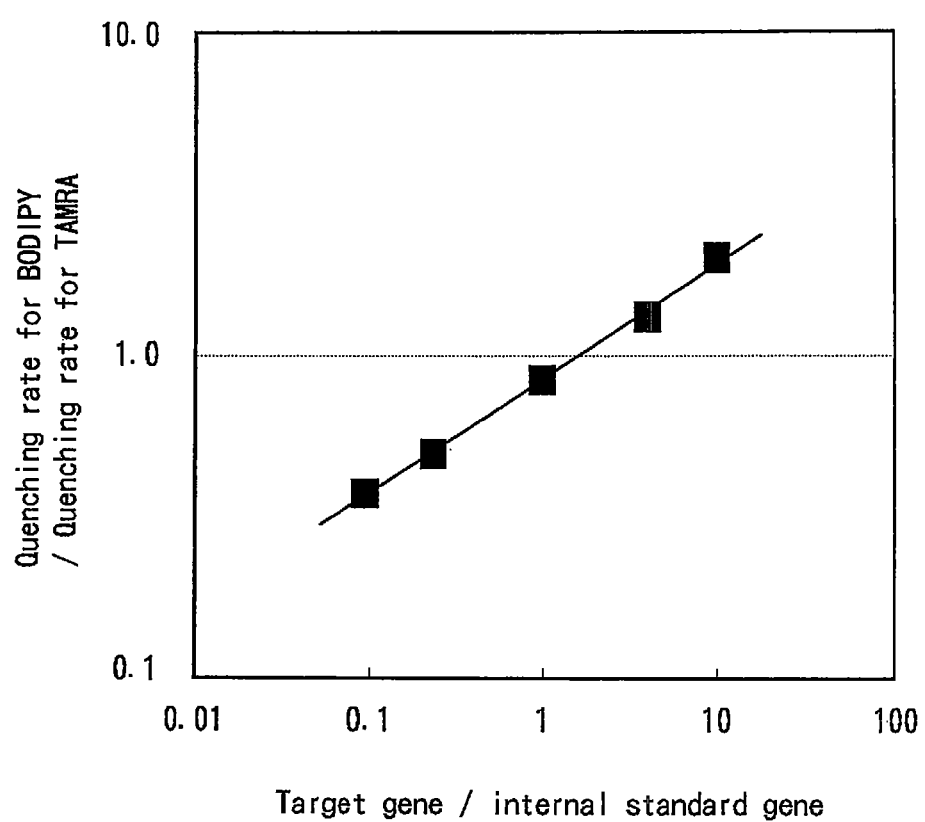
FIG. 7 illustrates the relation of a fluorescence quenching ratio and a constituent ratio of genes prior to a nucleic acid-amplification reaction (PCR) (in using an end-point gene-quantitatively-assaying method through a gene-amplification method using a switching probe).

BODIPY FL, 4,4-difluoro-5,7-dimethyl-4-bora-3a,4a-diaza-s-indacene-3-propionic acid was labeled on C of the 5'-end; the hybridization with a target gene resulted in a marked fluorescent quenching. On the other hand, TAMRA, Carboxytetramethylrhodamine was labeled on C of the 3'-end; the hybridization with an internal standard gene resulted in a marked fluorescent quenching. Thereby, a ratio between the quenching rate for BODIPY FL and the quenching rate for TAMRA was expected to be highly co-relative to an existing ratio of a target gene and an internal standard gene. FIG. 6 illustrates the experimental results. It is ascertained that a ratio between the quenching rate for BODIPY FL and the quenching rate for TAMRA is highly co-relative to an existing ratio of a target gene and an internal standard gene. These results indicate that a target gene is capable of being determined quantitatively even by making use of a Switching probe.

The fluorescent quenching rates obtained on making of the Switching probe and the fluorescent quenching rates obtained on making use of two QProbe were compared. Those results are shown in Table 3. As confirmed from this table also, the fluorescent quenching rates obtained on making use of Switching probe is about two-times higher than those obtained on making use of two QProbes. This fact indicates that the use of a Switching probe enables more accurate determination of a target gene than the use of two QProbes.

TABLE 3

Comparison between quenching rate on use of Switching probe and that on use of two QProbes

| | Results | | Conditions for use | | |
|---|---|---|---|---|---|
| | | | Concentration of Probes (nM) | Target | Concentration of target (nM) |
| Switching probe | BODIPY FL Quenching rate | 35.2% | 400 | Target gene | 600 |
| | TAMRA Quenching rate | 72.5% | 400 | Internal standard gene | 600 |
| Two QProbes | QProbe A Quenching rate | 21.2% | 400 | Target gene | 600 |
| | QProbe B Quenching rate | 44.2% | 400 | Internal standard gene | 600 |

Example 4

2-4 Method for Assaying a Target Gene at an End Point through a Gene-amplifying Method (1) Experimental Method It was tried to ascertain whether or not a target gene could be assayed precisely by the method for assaying a target gene at an end point. A PCR method was adopted as a gene-amplifying method; and a Switching probe was adopted a probe.

(2) Experimental Conditions

Target Gene and Internal Standard Gene

Target gene: a PCR product of a soybean (round-up soybean) recombinant RRS gene; the base sequence of the target gene: 5'-<u>A</u>GTTC CGGAA AGGCC AGAGG A<u>G</u>-3'

(the underlined portions are different from those of an internal standard gene. The probe can hybridize with the described sequence. The sequence other than those is common to that of the target gene or internal standard gene; thereby, it is not described.).

Internal standard gene: a PCR product of a soybean (round-up soybean) recombinant RRS gene artificially incorporated with a mutation.

Base sequence of the internal standard gene: 5'-<u>G</u>GTTC CGGAA AGGCC AGAGG A<u>A</u>-3'

(The underlined portion is different from that of the target gene. The probe was capable of hybridizing with the described sequence. The sequence other than those was common to that of the target gene or internal standard gene; thereby, it is not described.).

Total final concentration as combined of internal standard gene and target gene: 1000 copy Starting constituent ratio: target:internal standard=9:1, 4:1, 1:1, 1:4, 1:9.

Preparation of Switching Probe

Synthesis: by relying custom synthesis services (Espec oligoservices Inc.).

Base Sequence and Structure of Switching Probe

```
BODIPY FL-5'CTCCT CTGGC CTTTC CGGAA CC3'-TAMRA
```

(Dyes are like the above)
Final concentration of probe: 400 nM
Conditions of PCR
Denaturing: 95° C. (60 seconds)
Annealing: 56° C. (60 seconds)
Extension: 72° C. (60 seconds)
Enzyme for amplification of gene: Gene Taq (Nihon Gene Inc.) was used as a Taq polymerase Primer
Synthesis: by relying custom synthesis services (Espec oligoservices Inc.).
Base sequence of forward primer: 5' CCTTT AGGAT TTCAG CATCA GTGG3'
Base sequence of reverse primer: 5' GACTT GTCGC CGGGA ATG3'
Final concentration of primer: each 1000 nM
Preparation of Internal Standard Gene An oligoDNA having a base sequence of a internal standard gene as targeted was prepared by relying custom synthesis services (Espec oligoservices Inc.). The obtained oligoDNA was amplified, using itself as a temperate, by a PCR amplification method using the above primer for detecting; the amplification product was purified using Microcon PCR (Millipore Inc.). Following the purification, the amplification product was assayed quantitatively using PicoGreen (Molecular probes Inc.); the amplification product obtained in such a way is used as an internal standard gene.

Preparation of PCR Product of Target Gene

It was prepared like the preparation method of the internal standard gene.

Used Apparatus and Measuring Conditions

Used apparatus, used instrument, assaying conditions, and method for determining a fluorescent quenching rate on determination of fluorescent quenching rates were like those of Example 2-1

Quantitative determination using PicoGreen was conducted at 480 nm as an excitation wavelength and 520 nm as a fluorescent wavelength. Used slit width was 5 nm in any wavelengths. The PCR was conducted using a thermal cycler (iCycler, Biorad Inc.).

(3) Experimental Results

It was ascertained that a ratio between a fluorescent quenching rate for BODIPY FL and a fluorescent quenching rate for TAMRA was highly co-relative to the existing ratio between a target gene and an internal standard gene based on the obtained relative equation between those. From these results, it was suggested that a target gene and an internal standard gene was amplified with keeping a starting gene-constituent ratio. In addition, this method was shown to be capable of assaying a target gene through a gene amplification method.

Example 5

In regard to a novel mixture comprising a nucleic acid probe for a homogenous solution system and an internal standard nucleic acid and a method for assaying a gene by use thereof, preferable examples are shown in the following.

(1) Experimental Method

A possibility was examined of determining an existing ratio of a target gene and internal standard gene by making use of a probe for a homogenous solution system (a QProbe was used here). In the experiment, after preparation of a DNA solution containing a target gene and an internal standard gene with varied existing ratios thereof, a QProbe was added in the DNA solution and then fluorescent measurements were conducted. The fluorescent measurements were conducted at 60° C. and 95° C. (the measuring values at 60° C. were those on hybridization of the probe with a target gene; the measuring values at 95° C. were those on complete cleavage of the hybrid complex of the probe and the target gene). Incidentally, the measuring values at 95° C. were taken as a reference so as to determine a fluorescence-quenching rate. In addition, a relation of a ratio of the fluorescence-quenching rates of the each probes and a existing ratio of the target gene and the internal standard gene was examined; it was examined whether or not a gene existing ratio could be determined based this relative equation.

Detailed experimental conditions are shown below.

(2) Experimental Conditions

Target Gene and Internal Standard Gene

Target gene and internal standard gene: oligonucleotides were used.

Synthesis of oligonucleotide: by relying custom synthesis services (Espec oligoservices Inc.).

Base sequence of target gene: 5'-AGTTC CGGAA AGGCC AGAGG AG-3'

Base sequence of internal standard gene: 5'-GGTTC CGGAA AGGCC AGAGG AA-3'

Total final concentration as combined of internal standard gene and target gene: 200 nM, 400 nM, 800 nM (target: internal standard=9:1, 3:1, 1:1, 1:3, 1:9).

QProbe

Synthesis: by relying custom synthesis services (Espec oligoservices Inc.).

Sequence: 5'-CTCCT CTGGC CTTTC CGGAA CC-3'

Dye: BODIPY FL (Molecular probes Inc., D-6140).

Final concentration of each QProbe: 400 nM

Buffer: 10 mM Tris-HCl buffer (pH: 8.3), KCl: 50 mM, $MgCl_2$: 1.5 mM.

Used apparatus: fluorescence measurements were carried out by a fluorometer, LS50B (PerkinElmer Inc.) with a temperature-controlling instrument (Inc.); the measurements were conducted at 480 nm excitation wavelength and 520 nm fluorescence wavelength.

Fluorescence measurements on hybridization were conducted 60° C. A fluorescent intensity at the temperature (95° C.) as a reference, the temperature completely dehybridizing from a probe; fluorescent quenching rates were determined based on the following equation.

A fluorescent quenching rate (%)=(1−(F60/F95)/(only F60 probe/only F95))×100, wherein F60: a fluorescent intensity value at 60° C. in presence of a target gene;

F95: a fluorescent intensity value at 95° C. in presence of a target gene;

Only F60: a fluorescent intensity value at 60° C. in absence of a target gene

Only F95: a fluorescent intensity value at 95° C. in absence of a target gene.

(3) Experimental Results and Discussion

Figure 10:
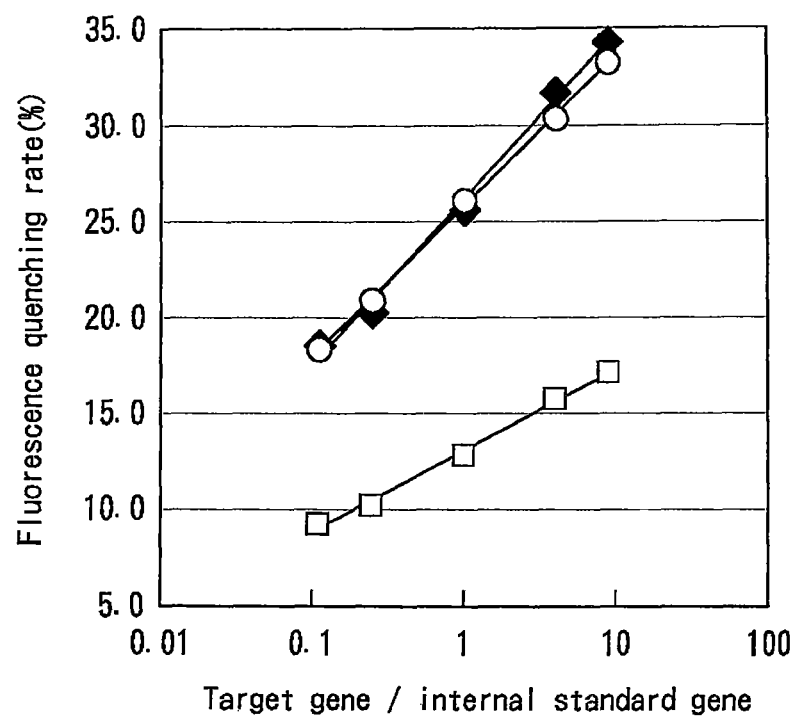
FIG. 10 illustrates the relation of a constituent ratio of genes and a fluorescence-quenching ratio in the use of a probe for a homogenous solution system.
  □ total gene-amount: 200 nM; ○ total gene-amount: 400 nM; ◆ total gene-amount: 800 nM

FIG. 10 shows the experimental results. When the total sum amount of the target gene and the internal standard gene was equal to the additive amount of the probe (400 nM), and when more than the additive amount of the probe (800 nM), the calibration curves agreed with each other. This showed that, when the amount of the probe was not more than the total sum of the amount of a gene, the gene-constituent ratio obtained on determination of a fluorescent quenching rate for the BODIPY dye was equaled regardless of a total sum of the amount of a gene. Accordingly, it is shown that, when the amount of a probe is not more than a total sum of the amount of a gene, a gene-constituent ratio can be accurately determined quantitatively based on an obtained fluorescent quenching rate for a BODIPY dye. The calibration curve in the case that the amount of a probe was more than the total sum of the amount of the gene (200 nM), however, was not agreed with the calibration curve in the case that the amount of the probe was not more than the total sum of the amount of the gene. This was interpreted by an because that, when a total sum of the amount of the gene was 200 nM, the additive amount of the probe was 400 nM; the non-hybridized probe was present 200 nM; thereby a fluorescent quenching rate was rendered about a half as compared with that in the case when the total sum of the amount of the gene was 400 nM or 800 nM.

Incidentally, in the case when a total sum of the amount of a gene (a concentration of a target nucleic acid) was not more than the amount of a probe, a measurement was preferable to conduct with a probe making its amount vary in order to solve a problem of the non-agreeable calibration curve.

Example 6

Method for assaying a gene using a novel mixture comprising a doubly-labeled nucleic acid probe and internal standard nucleic acid (part 2)

Although, in the method as described in Example 5 also, a target nucleic acid is capable of being assayed accurately by making the amount of a probe vary variously, this method can preferably assay a target nucleic acid using a probe making its amount vary variously.

(1) Experimental Method

Figure 11:
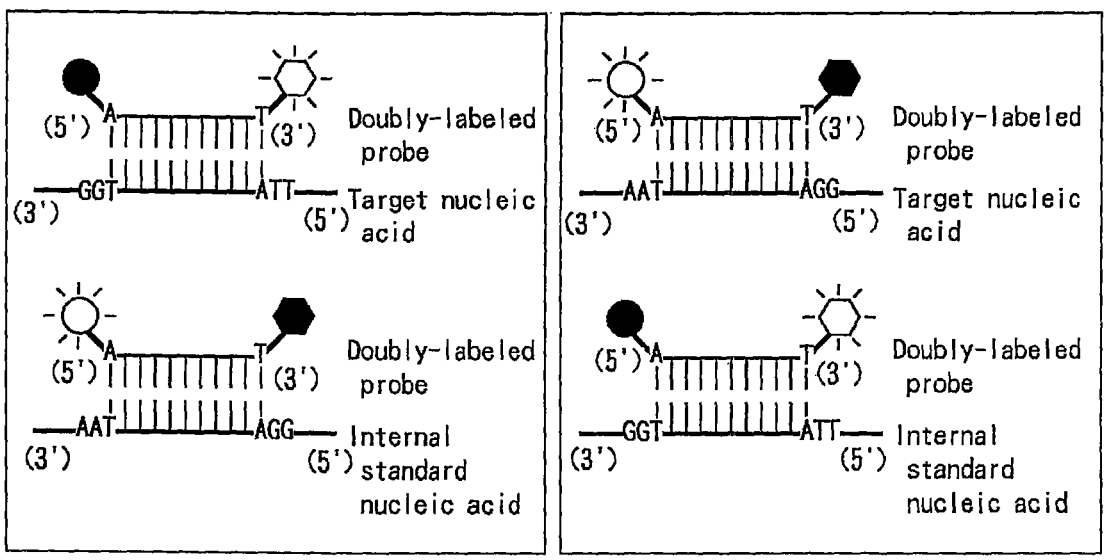
FIG. 11 illustrates a outline of the method for detecting a gene using a doubly-labeled nucleic acid probe (its part 2)

It was examined whether or not a existing ratio of target nucleic acids was capable of being assayed like the case of making use of the above-described doubly-labeled probe (a probe labeled at C or G self) by using a doubly-labeled probe of such a type that the probe was rendered variable in the fluorescent intensity by causing the number of G of a target nucleic acid and internal standard nucleic acid to change between the both in a range of from the $1^{st}$ base to the $3^{rd}$ from the base corresponding to a fluorescence-labeled portion (a base corresponding to a labeled base being counted as the $1^{st}$ base), wherein the doubly-labeled probe was completely complementary to the target nucleic acid and internal standard nucleic acid (FIG. 11).

Detailed experimental conditions is described in the following.

(2) Experimental Conditions

Target Gene and Internal Standard Gene

Target gene and internal standard gene: oligonucleotides were used.

Synthesis of oligonucleotide: by relying custom synthesis services (Espec oligoservices Inc.).

Base Sequence of Target Gene (a Sequence Underlined is Capable of Hybridizing to the Probe)

5'-TAA<u>TG ATGAC TGACT GACTC ACTGA CGATG</u> GT-3'

Base Sequence of Internal Standard Gene (a Sequence Underlined is Capable of Hybridizing to the Probe)

5'-TGG<u>TA TGACT GACTG ACTGA CTGAC GAGTA</u> AT-3'

Total final concentration as combined of internal standard gene and target gene: 200 nM, 400 nM, 800 nM (target: internal standard=9:1, 3:1, 1:1, 1:3, 1:9).

Doubly-labeled Nucleic Acid Probe

```
BODIPY FL-5' ACTAC TGACT GACTG ACTGA CTGCT CA
3'-TAMRA
```

Final concentration: 400 nM

Incidentally, used fluorescent dyes and relying custom synthesis services and the like were like Example 5.

Used apparatus, used instrument, conditions for assaying, and method for determining a fluorescent quenching rate were like those of Example 5.

Marked fluorescent quenching for BODIPY FL of the doubly-labeled probe was caused because of the presence of G in near proximity of a fluorescence-labeled end base on its hybridization to the target gene; but the hybridization of the doubly-labeled probe to the internal standard nucleic acid led to no fluorescent quenching because of the absence of G in near proximity of a fluorescence-labeled end base.

On the other hand, for BODIPY FL of the doubly-labeled probe, marked fluorescent quenching for was caused because of the presence of G in near proximity of a fluorescence-labeled end base on hybridization of the doubly-labeled probe to the internal standard nucleic acid. Therefore, a ratio between a fluorescent quenching rate for BODIDY FL and a fluorescent quenching rate for TAMRA was expected to be high co-relative to a ratio between a target gene and internal standard gene.

(3) Experimental Results and Discussion

Figure 12:
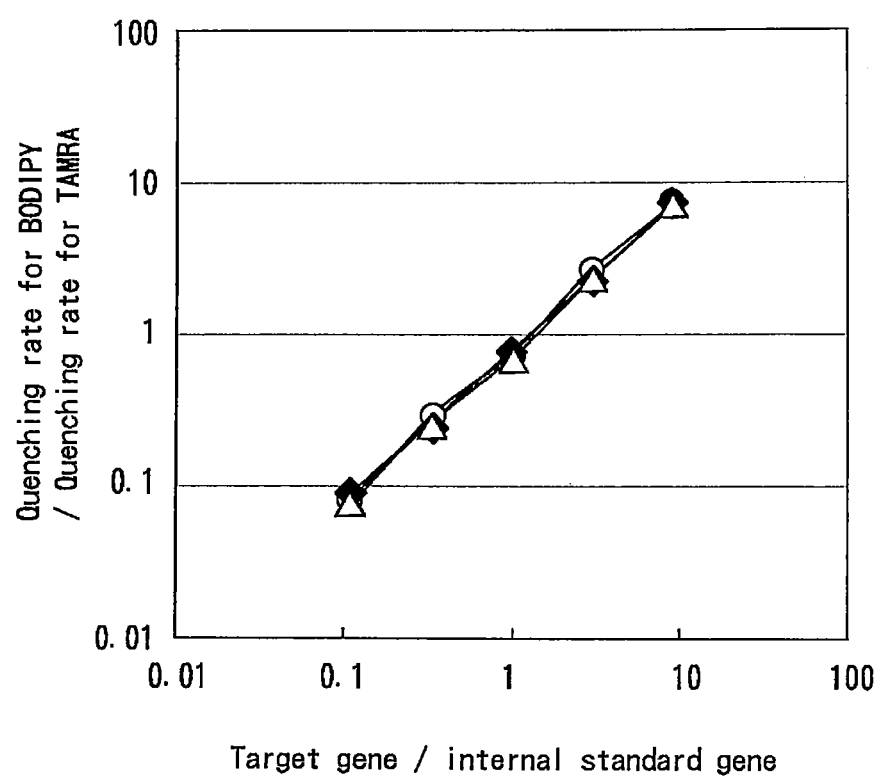
FIG. 12 illustrates the relation between a ratio of a fluorescence-quenching ratio in BODIPY FL dye to a fluorescence-quenching ratio in TAMURA dye and a constituent ratio of genes of a target gene/an internal standard gene.
  ○ gene amount: 200 nM; ◆ gene amount: 400 nM; Δ total gene amount: 800 nM

The experimental results are shown in FIG. 12. From the graphs, a ratio between a fluorescent quenching rate for BODIDY FL and a fluorescent quenching rate for TAMRA is ascertained to be high co-relative to a ratio between a target gene and internal standard gene. It is suggested from these results that the method using the doubly-labeled nucleic acid probe of this model is capable of accurately assaying a target gene quantitatively in any case where the total amount of a gene was larger than that of a probe, or smaller.

Example 7

Method for assaying a gene using a novel mixture comprising a doubly-labeled nucleic acid probe and internal standard nucleic acid (part 3)

(1) Experimental Method

It was examined whether or not an existing ratio of target nucleic acids was capable of being determined, like using the above described doubly-labeled probe, using also a doubly-labeled nucleic acid probe designed such that, in regard to a fluorescent dye labeled to one portion of two labeled portions of the a doubly-labeled nucleic acid probe, the change amount in a fluorescent character was caused in a similar degree on hybridization of the one portion to any of a target nucleic acid and an internal standard nucleic acid; but, in regard to a fluorescent dye labeled to the other portion, a difference between the change amount in a fluorescent character on hybridization of the other portion with the target nucleic acid and the change amount in a fluorescent character on hybridization of the other portion with the internal standard nucleic acid was caused (FIG. 13).

Detailed experimental conditions are described in the following;

(2) Experimental Conditions

Target Gene and Internal Standard Gene

Target gene and internal standard gene: oligonucleotides were used.

Synthesis of oligonucleotide: by relying custom synthesis services (Espec oligoservices Inc.).

Base Sequence of Target Gene (a Sequence Underlined is Capable of Hybridizing to the Probe)

```
5'-TAAGG ATGAC TGACT GACTG ACTGA CGATG GT-3'
```

Base Sequence of Internal Standard Gene (a Sequence Underlined is Capable of Hybridizing to the Probe)

```
5'-TAAGA TGACT GACTG ACTGA CTGAC GAGTA AT-3'
```

Total final concentration as combined of internal standard gene and target gene: 200 nM, 400 nM, 800 nM (target: internal standard=9:1, 3:1, 1:1, 1:3, 1:9).

Base Sequence and Structure of Doubly-labeled Nucleic Acid Probe

```
BODIPY FL-5'ACTAC TGACT GACTG ACTGA CTGCT CC
3'-TAMRA
```

Final concentration: 400 nM

Incidentally, used fluorescent dyes were like Example 5.

Used apparatus, used instrument, conditions for assaying, method for determining a fluorescent quenching rate, buffer and the like were like those of Example 5.

Marked fluorescent quenching for BODIPY FL labeled at the 5'-end of the doubly-labeled probe was caused because of the presence of G in near proximity of a fluorescence-labeled end base on its hybridization to the target gene; but the hybridization of the doubly-labeled probe to the internal standard nucleic acid led to no fluorescent quenching because of the absence of G in near proximity of a fluorescence-labeled end base. Thus, it is thought that a fluorescent quenching rate is in high correlation of an existing ratio of target nucleic acids. Further, if a proportion in quantity of a hybridized probe is known, the proportion of a probe hybridized to a target nucleic acid (or an internal standard nucleic acid) to the total amount of the hybridized probe comes to be possible to determine. This will be explained based on the following examples. In the case that it was calculated that the quenching rate for a fluorescent dye having a difference in a fluorescent quenching level caused on hybridization between a target nucleic acid and an internal standard nucleic acid in a practical sample was 40%; and the half of the total amount of an added probe was hybridized, if on paying attention to only a hybridized probe, the 80% amount of the hybridized probe comes to cause a fluorescent quenching. Provided that a probe used herein is taken to be a probe causing to quench completely a fluorescent emission of a BODIPY FL dye on hybridization of the probe to a target gene, the 80% amount of the hybridized probe is capable of being calculated based on the quenching rate (40%) in the practical sample. Thus determination of a proportion in quantity of a hybridized probe and a fluorescence-quenching made it possible to determine quantitatively a constituent ratio between a target gene and internal standard gene.

Fluorescent quenching for TAMRA labeled at the 3'-end of the doubly-labeled probe was markedly caused in similar levels on hybridization to a target gene and on hybridization to an internal standard gene because of the presence of G in near proximity of a fluorescence-labeled end base in the both of the target gene and the internal standard gene on its hybridization to the target gene. Because of this, the quenching rate for a TAMRA dye came to indicate a proportion of a hybridized probe.

As described above, it is thought that, if a proportion of a hybridized probe is known, a constituent ratio of a gene is capable of be determined quantitatively. A target gene was capable of be determined quantitatively by correction of a quenching rate for a BODIPY FL dye with a quenching rate for a TAMRA dye irrespective of a magnitude of the total amount of a gene.

(3) Experimental Results and Discussion

Figure 14:
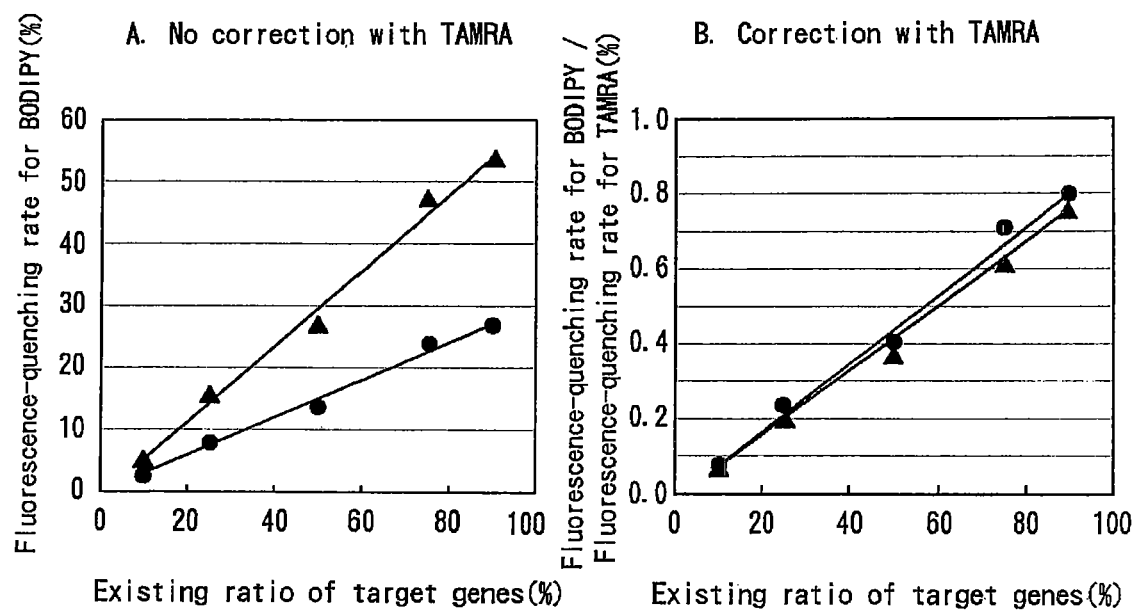
FIG. 14 illustrates a difference between a calculating curve with correction in TAMURA dye and a calculating curve with no correction in TAMURA dye.
  ● total gene-amount: 200 nm; ▲ total gene-amount: 800 nM
Figure 16:
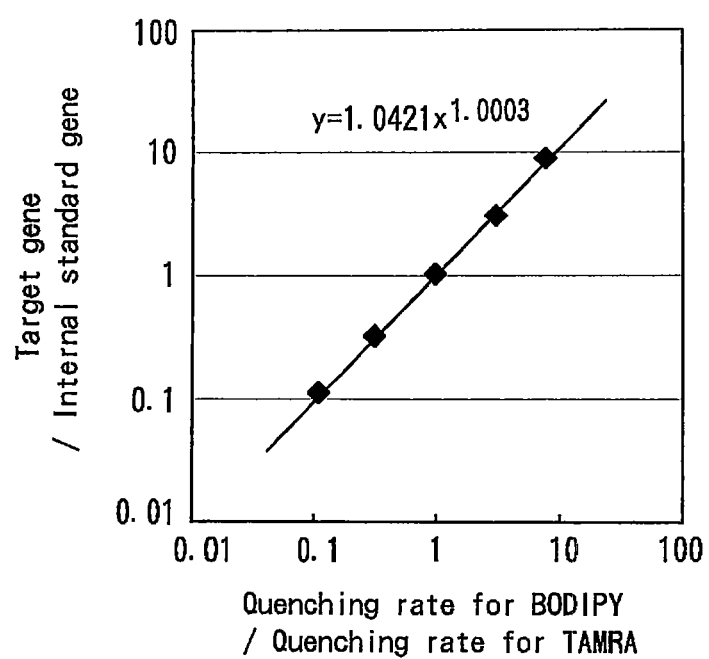
FIG. 16 illustrates an relative equation as to a proportion of a target gene and a fluorescence-quenching ratio

FIG. 14 shows experimental results. FIG. 14A shows a correlation of a fluorescence-quenching rate for a BODIPY dye and an existing ratio of a target gene. From this figure, it was understood that calibration curves each other was different with depending on the total amount of a target gene. These results indicate that a fluorescence-quenching varies with changed amounts of genes even if existing ratios of target genes are the same. From this, it is apparently impossible to determine an existing ratio of target genes. On the other hand, in a value (a fluorescence-quenching rate for a BODIPY dye/a fluorescence-quenching rate for a TAMRA dye) obtained by dividing a fluorescence-quenching rate for a BODIPY dye by a fluorescence-quenching rate for a TAMRA dye indicating a proportion in quantity of a hybridized probe, it is understood that these equations were almost in agreement irrespective of different amounts of a gene (FIG. 14B). In conclusion, a value of a fluorescence-quenching rate for a BODIPY dye/a fluorescence-quenching rate for a TAMRA dye was confirmed to change with depending on only a existing ratio of target genes and without depending on the total amount of a target gene. It is suggested from the above results that the method using a doubly-labeled probe of the above type is capable of determining an existing ratio of target genes accurately and quantitatively irrespective of a magnitude of the total amount of a target gene.

Insofar as that a probe usable in the method can have features such as follows: (1) the fluorescence amount of a dye labeled at one portion of the probe on hybridization of the probe with a target gene is different from that on hybridization of probe with an internal standard gene, and (2) in a dye labeled at another portion, the fluorescence amount (it may be a fluorescence-quenching or a fluorescence-emission) is caused in similar levels on hybridization with either a target gene or an internal standard gene, namely insofar as the probe has such properties, this method is capable of assaying any gene based on the above principal. Insofar as that a change in a fluorescent character in a dye usable for this method may be caused on hybridization of a probe with a gene, any dye may be usable, namely insofar as a dye has such properties, specifically no limitation is imposed on a dye.

Example 8

Method for accurately calculating concentration of target nucleic acid based on fluorescence measuring value Probes used in the above Examples (excluding Example 7) were probes such that fluorescence amounts for dyes with which the probes were labeled varied on hybridization of the probes with any one of a target gene and internal standard gene; on hybridization of the probes with the other gene, the fluorescence amounts were in similar levels as compared with that on no hybridization. That is, the existing forms of a probe were three forms wherein one of those is a target gene and probe hybridizing complex form, the other an internal standard gene and probe hybridizing complex form, and the further one a non-hybridizing form; but, upon the payment of attention to the fluorescence amount for every one molecule of a dye, the existing forms of a probe wherein the forms each were different in the fluorescence amount were only two forms (see FIG. 15). However, a probe has been recognized to be present during the above achievement of the invention, which probe had three existing forms which each were different in the fluorescence amount, wherein the forms were three forms of a target gene and probe hybridizing complex form, an internal standard gene and probe hybridizing complex form, and a non-hybridizing form (see FIG. 15). Because there were a probe having three existing forms different in the fluorescence amount in a reaction system using a probe of such above type, it was thought to be difficult to determine a target nucleic acid by making use of a simple calculating-equation as described above. Accordingly, a calculating method for determining a target gene quantitatively was invented, which method was designed on the premise of the use of a probe wherein the fluorescence amount for the probe was different independently in a target gene and probe hybridizing complex form, an internal standard gene and probe hybridizing complex form, and a non-hybridizing form; it will be illustrated in the following description.

<Calculating Equation>

A calculating equation is illustrated in the following description, which equation is usable in the case using a doubly-labeled probe designed such that the fluorescent intensity for a dye with which a probe is labeled at one portion thereof is reduced remarkably on hybridization with a target gene; that for a dye with which the probe was labeled at the other portion thereof was reduced remarkably on hybridization with an internal standard gene.

That detail is described as follows.

Signs usable in the calculating equation are defined as follows:

$y$: a proportion of a hybridized probe;

$1-y$: a proportion of a non-hybridized probe;

$x$: a proportion of a target gene;

$1-x$: a proportion of an internal standard gene;

$A$: a ratio of the fluorescent intensity of dye A of the doubly-labeled nucleic acid probe on no hybridization in use of a practical sample to the fluorescent intensity of dye A of the doubly-labeled nucleic probe on no hybridization;

$a$: a ratio of the fluorescent intensity of dye A of the doubly-labeled nucleic acid probe on its 100%-hybridization with a target nucleic acid to the fluorescent intensity of dye A of the doubly-labeled nucleic acid probe on no hybridization;

$a'$: a ratio of the fluorescent intensity of dye A of the doubly-labeled nucleic acid probe on its 100%-hybridization with an internal standard nucleic acid to the fluorescent intensity of dye A of the doubly-labeled nucleic acid probe on no hybridization;

B: a ratio of the fluorescent intensity of dye B of the doubly-labeled nucleic acid probe on hybridization in use of a practical sample to the fluorescent intensity of dye B of the doubly-labeled nucleic acid probe on no hybridization;

b: a ratio of the fluorescent intensity of dye B of the doubly-labeled nucleic acid probe on its 100%-hybridization with a target gene to the fluorescent intensity of dye B of the doubly-labeled nucleic acid probe on no hybridization;

b': a ratio of the fluorescent intensity of dye B of the doubly-labeled nucleic acid probe on its 100%-hybridization with an internal standard nucleic acid to the fluorescent intensity of dye B of the doubly-labeled nucleic acid probe on no hybridization.

The fluorescent intensity proportion (A) of dye A in use of a practical sample is capable of being represented as follows:

$$A=(1-y)+axy+(1-x)a'y=1-y+axy+a'y-a'xy \quad (1)$$

If the equation (a) is deformed, a proportion (y) of a hybridized probe is capable of being represented as follows:

$$y=(1-A)/(a'x-ax+1-a') \quad (2)$$

On the other hand, a fluorescent intensity (B) for dye B in use of a practical sample is capable of being represented.

$$B=(1-y)+(1-x)by+b'xy=1-y-bxy+by+b'xy \quad (3)$$

If the equation (3) is deformed, a proportion of a hybridized probe is capable of being represented as follows:

$$y=(1-B)/(b'x-bx+1-b') \quad (4)$$

The equation (2) is incorporated with the equation (4); the resultant equation is represented as follows:

$$(1-A)/(a'x-ax+1-a')=(1-B)/(b'x-bx+1-b') \quad (5)$$

The deformation of the equation (5) leads the equation (6):

$$X=(-a'-B+Ba'+b'+A-Ab')/(b'-b-Ab'+Ab-a'+a+Ba'-Ba) \quad (6)$$

The items other than x are determined experimentally; a proportion of a target gene is thought to be capable of being calculated by an equation (6).

Detailed experimental conditions will be described below.

In the experiment, a constituent ratio of target genes in samples prepared imitatively (hereinafter, called simply a "mimic sample".) was determined by (1) a method comprising, subsequent to preparation of a calibration curve, determining quantitatively a constituent ratio of target genes by the prepared calibrating curve; or (2) a method comprising determining quantitatively a constituent ratio of target genes by the above calculating equation; and, based on the obtained results, the above two methods for determining quantitatively a constituent ratio of target genes were compared and evaluated.

(2) Experimental Conditions
<Target Gene and Internal Standard Gene>
Target gene and internal standard gene: an oligonucleotide was used.

Synthesis of oligonucleotide: by relying custom synthesis services (Espec oligoservices Inc.).

Base Sequence of Target Gene (a Sequence Underlined is Capable of Hybridizing to the Probe)

```
5'-AATTC GTACC AACTA TCCTC GTCGT CAGCT ATG-3'
```

Base Sequence of Internal Standard Gene (a Sequence Underlined is Capable of Hybridizing to the Probe)

```
5'-GATTC GTACC AACTA TCCTC GTCGT CAGCT ATA-3'
```

Additive amount of the target gene and internal standard gene in the measurement of the fluorescent quenching rate Target gene: 800 nM Internal standard gene: 800 nM Total final concentration as combined of internal standard gene and target gene (analytical curve): 800 nM (target: internal standard=9:1, 3:1, 1:1, 1:3, 1:9).

Total final concentration as combined of internal standard gene and target gene (mimic sample): 200 nM, 800 nM (target: internal standard gene=4:1).

Base Sequence and Structure of Doubly-labeled Nucleic Acid Probe

```
BODIPY FL-5'CATAG CTGAC GACGA GGATA GTTGG TACGA
ATC 3'-TAMRA
```

Incidentally, used fluorescent dyes were like. Example 6. Final concentration of the probe was 400 nM.

The other conditions (used apparatus, used instrument, conditions for assaying, and the like) were like those of Example 7.

(3) Results and Discussion

<Measurement of Fluorescence-quenching Rate of Probe>

Firstly, the fluorescence-quenching rate—in a target gene and probe hybridizing complex form, an internal standard gene and probe hybridizing complex form, and a non-hybridizing form—of the probe used in this example were measured. Incidentally, in the measurement of the fluorescent quenching rate for a BODIPY FL dye, a fluorescent quenching rate obtained in an experimental system where an internal standard gene was added therein was used as a basal unit (the quenching rate=0%); the other quenching rates were calculated based on the basal unit. In the measurement of the fluorescent quenching rate for a TAMRA dye, a fluorescent quenching rate obtained in an experimental system where a target gene was added therein was used as a basal unit (the quenching rate=0%); the other quenching rates were calculated based on the basal unit. The results are shown in the following table. As understood from the table, the fluorescent quenching rates of an experimental system with no addition of a gene (a gene-non-additive system) were not 0% for both dyes. These findings indicate that, on hybridization of the probe with a target gene also—the gene not having a G in the base-sequence position complementary to a labeled base of the probe, the fluorescence amount emitted from the dye labeled to the probe was variable 1. From the above findings, it is ascertained that the fluorescence amount for the probe used in this example varies in a target gene and probe hybridizing complex form, an internal standard gene and probe hybridizing complex form, or a non-hybridizing form.

TABLE 4

Quenching rate in each conditions of probe used in Example

| | BODIPY FL | | | TAMRA | | |
|---|---|---|---|---|---|---|
| | No addition of gene | Addition of only target gene (800 nM) | Addition of only internal standard gene (800 nM) | No addition of gene | Addition of only target gene (800 nM) | Addition of only internal standard gene (800 nM) |
| Fluorescent intensity (95° C.) | 110 | 122 | 105 | 87 | 82 | 91 |
| Fluorescent intensity (60° C.) | 129 | 24 | 117 | 135 | 145 | 20 |
| 60° C./95° C. | 1.17 | 0.19 | 1.11 | 1.56 | 1.77 | 0.22 |
| Quenching rate (%) | −5.0 | 82.6 | 0.0 | 12.0 | 0.0 | 87.5 |

<Determination of Existing Ratio of Target Gene>

The below figure illustrates a calibrating curve. It is recognized that an existing ratio of a target gene is highly co-relative to a fluorescence-quenching rate. Accordingly, existing ratios of target genes in mimic samples were determined quantitatively based on the relative equation obtained from this calibrating curve.

The results of the determination are shown in the below table. From these results, it is understood that appropriate determining values come to having been obtained as determining values in the case that the total sum amount of a target gene was 800 nM, because the determining values were close to the theoretical value (a target, gene: an internal standard gene in the mimic samples were 4:1; the theoretical value was 4.0). When the total sum amount of genes was, however, 200 nM, the obtained constituent ratio of the target genes was about half of the theoretical value. Based on the above results, it is suggested that a constituent ratio of genes are capable of being appropriately determined in the case that the amount of a probe is smaller than the total sum amount of genes, and in the case that the determination was conducted using a probe designed such that the fluorescence amount for the probe used in the determination was different in no-hybridization with any gene, in hybridization with a target gene and in hybridization with an internal standard gene, respectively.

fluorescence amount for a dye labeled at the probe was different in no hybridization with any genes, in hybridization with a target gene and in hybridization with an internal standard gene, respectively; in the case when the total sum amount of genes is smaller than the amount of a probe, the change amount in the fluorescence for each dye labeled at the probe comes to be derived from the both of the change amount in the fluorescence on hybridization with an internal standard gene and the change amount in the fluorescence on hybridization with a target gene (in the case when the change amount in the fluorescence on no hybridization with any genes was taken as a basal value). That is, the change amount in the fluorescence in regard to each dye came to be affected by the both of a target gene and an internal standard gene. Because of such a situation, it is understood that a ratio of change amounts in fluorescence did not reflect a ratio of a constituent ratio of genes; and appropriate determining values were not capable of being obtained. On the other hand, in the case of the total sum amount of genes of 800 nM, a probe hybridized to any of a target gene and an internal standard; a probe not hybridized was not present. Thereby, the change amount in fluorescence was derived from only one gene of the target gene and the internal standard gene. Accordingly, a ratio of the change amount in fluorescence came to reflect appropriately on a constituent ratio of genes; an appropriate determining value is thought to have been obtained.

TABLE 5

Quantitative ratio of target genes existing in a system (target gene/internal standard gene), obtained by use of calibrating curve

| Total amount of gene | BODIPY FL Quenching rate | TAMRA Quenching rate | BODIPY-Quenching rate/TAMRA-Quenching rate | Quantitative value (target/internal standard) | Theoritical value (target/internal standard) |
|---|---|---|---|---|---|
| Mimic sample 1 (※1) | 63.4 | 17.3 | 3.66 | 3.82 | 4.0 (target:internal standard = 4:1) |
| Mimic sample 2 (※2) | 31.2 | 14.6 | 2.13 | 2.22 | |

Added amount of probe: 400 nM
(※1); Total amount of probe: 200 nM
(※2); Total amount of probe: 800 nM The additive amount of a probe in this example was 400 nM; in the case with the total sum amount of genes being 200 nM, the half of the additive amount of the probe does not hybridize to genes. In the probe used this example, the The following Table 6 shows the results of determination of a constituent ratio of genes using the above described calculating equation. The measuring values—those values were used for determining quantitatively by a calibrating curve—was divided by the fluorescence amount for a non-hybridized probe; the obtained values were incorporated in the calculating equation. Based on this table, it is recognized that an accurate constituent ratio of genes (the amount of a target gene/the amount of an internal standard gene) had be capable of being determined even in the case when the total sum amount of genes was smaller than the total amount like in the case when larger. Therefore, a constituent ratio of genes is clearly capable of being quantitatively determined using the above-described relative equation nevertheless of the total sum amount of genes.

TABLE 6

Quantitative gene-constituent ratio (target gene/internal standard gene), obtained by use of novel calculating equation

| | BODIPY Relative fluorescent intensity | TAMRA Relative fluorescent intensity | Quantitative value (target/internal standard) | Theoritical value (target/internal standard) |
|---|---|---|---|---|
| Non-hybridizing probe | 1.00 | 1.00 | — | — |
| 100% target gene (BODIPY: a, TAMRA: b) | 0.17 | 1.14 | — | — |
| 100% internal standard gene (BODIPY: a', TAMRA: b') | 0.95 | 0.14 | — | — |
| Mimic Sample 1 Total amount of gene: 200 nM (BODIPY: A, TAMRA: B) | 0.66 | 0.97 | 4.02 | 4.00 |
| Mimic Sample 2 Total amount of gene: 800 nM (BODIPY: A, TAMRA: B) | 0.35 | 0.94 | 4.00 | |

Example 9

Example determining a target gene by using novel mixture according to present invention, comprising quenching substance or probe labeled with quenching substance.

In the case when the amount of a total sum of genes is greatly smaller than the additive amount of a probe, it is expected that the amount of a change in fluorescence for the probe become smaller; and, as a results, a target gene could not be accurately determined quantitatively (see FIG. 17A). If fluorescent emission from non-hybridizing probe is, however, capable of being quenched, the amount of a change in fluorescence could be determined; as a result, even in the case when the amount of a total sum of genes was greatly smaller than the additive amount of a probe, a target gene was expected to be capable of being determined (see FIG. 17B). In order to achieve this object, it was thought to be effective to make use of a probe labeled with a fluorescence-quenching substance (called a "quenching substance-labeled probe"). As conditions for preferable use of the quenching substance-labeled probe, the following three requirements should be mentioned: (1) the quenching substance-labeled probe can hybridize to a target nucleic acid probe; (2) the quenching substance, with which the quenching substance-labeled probe is labeled, can be located in close proximity to a dye, with which the target nucleic acid probe is labeled, on hybridization of the quenching substance-labeled probe with the target nucleic acid probe; and (3) the dissociation temperature of a hybrid complex between the target nucleic acid probe and the quenching substance-labeled probe can be lower than that of a hybrid complex between the target nucleic acid probe and a target nucleic acid or that of a hybrid complex between the target nucleic acid probe and an internal standard nucleic acid. An additionally preferable applicable-example is shown in FIG. 17B. The quenching substance-labeled probe has the following features; (1) it has a base sequence complementary to that of a doubly-labeled probe; (2) on hybridization to the doubly-labeled probe, the base of the quenching substance-labeled probe complementary to a fluorescence-labeled base of the doubly-labeled probe is labeled with a quenching substance; and (3) it has two oligonucleotides shorter than that of a target nucleic acid probe; and each of the oligonucleotides can hybridize to a separate portion of the target nucleic acid probe without doubling.

The above features of (1), (2) and (3) can cause the fluorescence of a doubly-labeled nucleic acid probe to quench without inhibition of hybridization of the doubly-labeled nucleic acid probe to an internal standard nucleic acid and a target nucleic acid.

(1) Experimental Method

The experiment was conducted in a system with addition of the quenching substance-labeled nucleic acid probe and in a system without addition; the effect of the quenching substance-labeled nucleic acid probe was evaluated by comparison of determining values as to existing ratios of target genes in mimic samples. The determination of a existing ratio of target genes was carried out by making use of the calculating equation as described in Example 8.

Prior to the above experiment, ranges of specific temperature were in advance determined; at one of the ranges the doubly-labeled nucleic acid probe was capable of hybridizing enough to only a target gene and an internal standard gene, but of not hybridizing to the quenching substance-labeled nucleic acid probe; at the other range the doubly-labeled nucleic acid probe was capable of hybridizing enough to a target gene, an internal standard gene and the quenching substance-labeled nucleic acid probe. The temperature range was 55 to 60° C. in the former and not higher than 40° C. in the later. Based on the results, in ascertaining experiment, the temperature was changed to 95° C., 57° C., and 35° C. in this order and kept for one minute to an individual temperature. The object of keeping the temperature to 57° C. was to make the doubly-labeled nucleic acid probe hybridize to only a target gene and an internal standard gene. Subsequent to that, the keeping of 35° C. made the doubly-labeled nucleic acid hybridize to the quenching substance-labeled nucleic acid probe to cause the fluorescence for the doubly-labeled nucleic acid to be quenched.

(2) Experimental Conditions

<Target Gene, Internal Standard Gene, and Doubly-labeled Nucleic Acid Probe>

Target gene, internal standard gene, and doubly-labeled nucleic acid probe: the same as in Example 8 were used.

Quenching substance-labeled nucleic acid probe

DABCYL (Glean research Inc., USA) was used. The base sequence is described as follows.

Quenching Substance-labeled Nucleic Acid Probe A:

5'<u>CTCGT CGTCA GCTAT GG</u>3'-DABCYL

Quenching Substance-labeled Nucleic Acid Probe B:

DABCYL-5'<u>GGATT CGTAC CAACT ATC</u>

(a region underlined is capable of hybridizing to the doubly-labeled probe)

Synthesis of oligonucleotide: by relying custom synthesis services (Espec oligoservices Inc.)

Total final concentration as combined of internal standard gene and target gene in mimic sample: 20 nM, 40 nM, 80 nM (target: internal standard=4:1)

Final concentration of doubly-labeled probe: 400 nM

Final concentration of quenching substance-labeled probe: 800 nM (3) Results and Discussion The following table shows the results of determination of a constituent ratio of genes in a system with no addition of a quenching substance-labeled nucleic acid probe. The results show clearly that the amount of a change in fluorescence reduced with reducing amount of total genes because a ratio of fluorescent intensity (A and B) in the mimic samples came close to a ratio of fluorescent intensity of the non-hybridized probe. The determining values of the gene constituent ratio in the mimic samples were consequently apart from the theoretical value with the reducing amount of a total sum of genes.

TABLE 7

Result of quantitation of gene-constituent ratio (a system without addition of quenching substance-labeled probe)

|  | BODIPY Relative fluorescent intensity | TAMRA Relative fluorescent intensity | Quantitative value (target/ internal standard) | Theoritical value (target/ internal standard) |
|---|---|---|---|---|
| Non-hybridizing probe | 1.00 | 1.00 | — | — |
| 100% target gene (BODIPY: a, TAMRA: b) | 0.17 | 1.11 | — | — |
| 100% internal standard gene (BODIPY: a', TAMRA: b') | 0.96 | 0.14 | — | — |
| Mimic Sample 1 Total amount of gene: 80 nM (BODIPY: A, TAMRA: B) | 0.87 | 0.97 | 2.98 | 4.00 |
| Mimic Sample 2 Total amount of gene: 40 nM (BODIPY: A, TAMRA: B) | 0.94 | 0.98 | 2.27 |  |
| Mimic Sample 3 Total amount of gene: 20 nM (BODIPY: A, TAMRA: B) | 0.98 | 0.99 | 1.39 |  |

The following table shows the results of determination of a constituent ratio of genes in a system with addition of a quenching substance-labeled nucleic acid probe. Even in this system, a ratio of fluorescent intensity (A and B) in the mimic samples was reduced with reducing amount of total genes. Nevertheless, even in the case of the amount of a total sum of genes of the smallest 20 nM, the change in a fluorescent intensity was observed to be about 1.5 to 2.0 times greater as compared with that for a non-hybridized probe. In the case of the reduced amount of a total sum of genes also, the obtained determining values of gene constituent ratios were the ones about close to the theoretical value. From the above results, it has become apparent that a gene-constituent ratio can be accurately determined quantitatively by addition of a quenching substance-labeled probe to reduce fluorescence for the non-hybridized probe, and, as a result, a target gene can be accurately determined quantitatively.

The quenching substance-labeled probe enabled to measure exactly the fluorescence derived from a probe hybridized to a target gene or an internal standard gene by making the fluorescence for a non-hybridizing probe quench. On the basis of this reason, the quenching substance-labeled probe is in merit for all the target nucleic acid probes (including an internal standard nucleic acid probe and a doubly-labeled probe) as described in the present application, and for an assaying method making use thereof.

In addition, in the case such that products amplified by a gene amplification method are targeted, the quenching substance-labeled probe is usable based on the same reason as described above. In such a case, it is necessary to conduct such a treatment as phosphorylation of the 3'-end of a probe in the use of the quenching substance labeled probe, in which the 3'-end is not labeled, in order to inhibit to be used as a primer (but, provided that the same shall not apply to the case when, subsequent to gene amplification, a constituent ratio of target genes is determined by adding a target nucleic acid probe (including an internal standard nucleic acid probe and a doubly-labeled nucleic acid probe) and a quenching substance-labeled probe in the reaction mixture of the gene amplification).

TABLE 8

Result of quantitation of gene-constituent ratio (a system with addition of quenching substance-labeled probe)

|  | BODIPY Relative fluorescent intensity | TAMRA Relative fluorescent intensity | Quantitative value (target/ internal standard) | Theoritical value (target/ internal standard) |
|---|---|---|---|---|
| Non-hybridizing probe | 1.00 | 1.00 | — | — |
| 100% target gene (BODIPY: a, TAMRA: b) | 6.17 | 25.00 | — | — |
| 100% internal standard gene (BODIPY: a', TAMRA: b') | 33.33 | 3.75 | — | — |
| Mimic Sample 1 Total amount of gene: 80 nM (BODIPY: A, TAMRA: B) | 3.12 | 4.85 | 3.83 | 4.00 |
| Mimic Sample 2 Total amount of gene: 40 nM (BODIPY: A, TAMRA: B) | 2.04 | 3.03 | 4.36 |  |
| Mimic Sample 3 Total amount of gene: 20 nM (BODIPY: A, TAMRA: B) | 1.56 | 1.99 | 3.64 |  |

Example 10

Method for assaying a target nucleic acid using a novel mixture comprising exonuclease according to the present invention The example is below described, related to the additionally novel method making use of both of a target nucleic acid probe and internal standard nucleic acid probe. This method makes use together of both of a target nucleic acid probe and internal standard nucleic acid probe and additionally an enzyme having exonuclease activity (hereinafter, called simply "exonuclease"). Its preferable example is described in FIG. 18. This method is premised on making use of 3'→5' exonuclease.

In this method, a target nucleic acid probe and an internal standard probe, which are labeled doubly with a fluorescent dye and a quenching substance are used. Fluorescent dyes to be used for labeling the target nucleic acid probe and the internal standard probe are more preferable to be different each others. Further, on use of 3'→5' exonuclease, fluorescence-labeling portion of the probes are preferably 3'-end portions; quenching substance-labeling portion of the probes are preferable to be different from the fluorescence-labeled portions. The target nucleic acid probe is preferably a probe designed such that, on hybridization with one of the target gene and internal standard gene, the fluorescence-labeled 3'-end-base of the probe is at least non-complementary to the one gene; and on hybridization with the other gene, the fluorescence-labeled 3'-end base of the probe is complementary to the other gene. (In FIG. 18, the target nucleic acid probe is designed so that, on its hybridization to a target gene, the fluorescence-labeled 3'-end base of the probe is at least non-complementary to the target gene; and on hybridization with the internal standard gene, the fluorescence-labeled 3'-end base of the probe is complementary to the internal standard gene. On the other hand, the internal standard nucleic acid probe is designed so that, on its hybridization to an internal standard gene, the fluorescence-labeled 3'-end base of the probe is at least non-complementary to the internal standard gene; and on hybridization with the target gene, the fluorescence-labeled 3'-end base of the probe is complementary to the target gene.). In the target nucleic acid probe and internal standard nucleic acid probe, if the probes keep complete forms thereof, the fluorescence of the fluorescent dyes labeled at the probes is quenched with affection of the quenching substances labeled at a portion within the same molecules. However, if there is a mismatch at the 3'-end, the 3'→5' exonuclease cleaves out the 3'-end base from the probes by recognizing the mismatch on hybridization of the target nucleic acid probe and internal standard nucleic acid probe with a target gene and internal standard gene in the presence of the enzyme having a characteristic such that the enzyme cleaves out the 3'-end base only in the case of a mismatch of the 3'-end. Accordingly, each probe comes to emit specifically fluorescence on hybridization to any one of a target gene and an internal standard gene (in FIG. 18, the target nucleic acid probe is cleaved and emits fluorescence only on hybridization to a target gene; the internal standard nucleic acid probe is cleaved and emits only on hybridization to an internal standard gene). A difference between the number of base pairs between the target nucleic acid probe and the target gene and the number of base pairs between the target nucleic acid probe and the internal standard gene is only one base pair; that one base pair is the end base of the target nucleic acid; it can be understood that the target nucleic acid probe hybridizes to a target gene and an internal standard gene with indiscriminating those (the internal standard nucleic acid probe also is like this). Owing to this, a ratio between fluorescence-determining values for each probes can appropriately reflect a gene-constituent ratio between a target gene and an internal standard gene existing a system. Accordingly, it is considered that the amount of a target gene can be determined quantitatively by this method also.

(1) Experimental Method

It was examined whether or not an existing ratio between a target gene and an internal standard gene existing in a system can be determined by using the above described target nucleic acid probe, internal standard nucleic acid probe and 3'→5' exonuclease. In the experiment, a DNA solution was prepared, wherein the solution comprised a target gene and internal standard gene in various existing ratios between those; the target nucleic acid probe, internal standard nucleic acid probe and 3'→5' exonuclease was added in the solution; subsequent to the addition, the solution was incubated for a determined time; and then a fluorescence measurement was conducted. The fluorescence measurement was carried out 95° C. A relation between a ratio of the amount of fluorescence derived from each probes and a gene-constituent ratio between a target gene and an internal standard gene was examined; and it was examined whether or not a gene-constituent ratio could be determined based on the obtained relative equation.

The following description shows detailed experimental conditions.

(2) Experiment Conditions

Target Gene and Internal Standard Gene

Target gene and internal standard gene: oligonucleotides were used.

Synthesis of oligonucleotide by relying custom synthesis services (Espec oligoservices Inc.).

Base Sequence of Target Gene:

5'TTGTC CGGAA AGGCC AGAGG AG-3';

Base Sequence of Internal Standard Gene:

5'-ATGTC CGGAA AGGCC AGAGG AG-3';

Total final concentration as combined of standard gene and target gene: 100 nM, 800 nM (target: internal standard=9:1, 3:1, 1:1, 1:3, 1:9).

Target Nucleic Acid Probe

Synthesis: by relying custom synthesis services (Espec oligoservices Inc.).

Sequence: DABCYL-5' CTCCT CTGGC CTTTC CGGAC AT 3'-BODIPY FL

Dye: BODIPY FL (like the dye used above), labeled portion: the 3' end;

Quenching substance dye: DABCYL (like the dye used above), labeled portion: the 5' end;

Final concentration: 200 nM.

Internal Standard Nucleic Acid Probe

Synthesis: by relying custom synthesis services (Espec oligoservices Inc.).

Sequence: DABCYL-5' CTCCT CTGGC CTTTC CGGAC AA3'-TAMRA

Dye: TAMRA (like the dye used above), labeled portion: the 3' end;

Corrosive sublimate dye: DABCYL (like the dye used above) labeled portion: the 5' end;

Final concentration: 200 nM.

3'→5' exonuclease: TaKaRa LA Taq (Takara Bio Inc.).

Buffer: A buffer attached with TaKaRa LA Taq was used.

Reaction time: 1 hr.

(3) Results and Discussion

Figure 19:
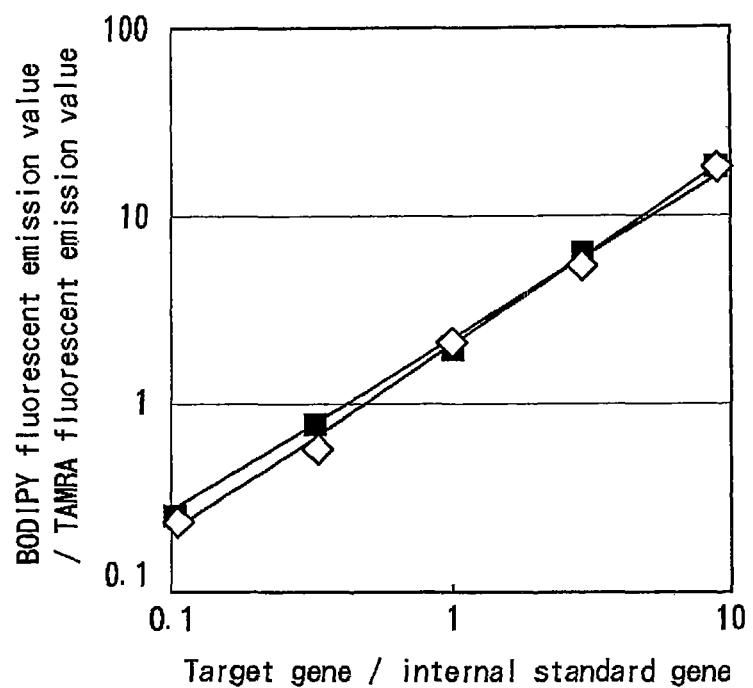
FIG. 19 illustrates a relation of a fluorescence-measuring-value ratio and a constituent ratio of genes.
  ■ 100 nM; ◇ 800 nM

FIG. 19 indicates the relation between a ratio of fluorescence-determining values and a gene-constituent ratio of genes. Based on this figure, it is ascertained that there is a high co-relation between an amount ratio of changes in fluorescence and a gene-constituent ratio regardless of the total amount of genes. From these findings, it is clear that a gene-constituent ratio can be determined accurately, and, by utilizing this ratio, a target gene can be determined quantitatively. Many heat-resistant enzymes for a PCR method are known to have a 3'→5' exonuclease activity. Because of these findings, the application of this method to a PCR method makes it unnecessary to add an enzyme having a 3'→5' exonuclease activity into an assaying system; this method could be carried out practically.

In this example, an instance utilizing a 3'→5' exonuclease activity has been described; if there is a mismatching base pair, the use of an enzyme having a 5'→3' exonuclease activity enables to determine a target gene like use of the enzyme, 3'→5' exonuclease. In this case, a fluorescence-labeling portion of a target nucleic acid probe and internal standard nucleic acid probe should be preferably a 5'-end base portion; a quenching substance-labeling portion is preferably a 3'-end base portion.

Example 11

Calculating equation for making it possible to accurately determine a concentration of target nucleic acid based on fluorescence measuring value (part 2).

The following description indicates an example making a doubly-labeled nucleic acid probe and a quenching substance-labeled probe in combination, wherein the doubly-labeled nucleic acid probe has the characteristics such that a difference between the fluorescent intensity in regard to a dye labeled at one portion of a doubly-labeled nucleic acid probe on hybridization of a doubly-labeled nucleic acid probe with a target gene and the fluorescent intensity on the hybridization of the above probe with an internal standard gene produces; and the fluorescent intensity in regard to a dye labeled at the other portion is in a similar degree on hybridization with any of the target gene and the internal standard gene. FIG. 20 illustrates a preferable example applied with this method. The one end of the doubly-labeled nucleic acid probe is labeled with a fluorescent dye (dye A) of such a type that the fluorescence for a fluorescent dye is capable of being quenched owing to an interaction of the dye with a G. Based on this labeling way, the fluorescence-quenching can occur because G is present in close proximity of the dye A on hybridization of the probe to a target gene; on hybridization to an internal standard gene, the fluorescence-quenching can not occur because G is absent in close proximity of the dye A. The other end should be labeled with a dye B, although any limitation should not be basically imposed on the dye, for which the fluorescent intensity becomes to be in the same level on hybridization of the probe with a target gene and on hybridization of the probe with an internal standard gene. Due to this labeling, the fluorescent intensity for dye. B labeled on the other end portion of the probe is not affected by a sort of gene on hybridization of the probe with the gene to become like; the fluorescence for a non-hybridizing probe can be made to quench by a quenching substance-labeled probe; this make it possible to determine quantitatively the proportion of a hybridized probe. As a dye for labeling the other end, a dye (dye B) which is difficult to be affected by a base sequence is preferable. Further, a dye difficult to be affected by a G is more preferable. In use of a dye for labeling a probe, for which dye the fluorescent intensity is easy to be affected by a G, in order to enhance the intensity of fluorescence emitted from the dye, it is preferable to select a base sequence region where a G is less in close proximity of the dye of the probe as a base sequence region of a target gene to which the probe hybridize. On the basis of this reason, the base sequences of a target nucleic acid and an internal standard nucleic acid imposes in an instance some limitation on a design of a probe. On the other hand, the use of a dye, for which the fluorescence is not affected by a G, broaden a free choice in a probe design to become more preferable, because, if a G exists in close proximity of dye B, the fluorescence for dye B is not affected by a G.

Illustrative are Cy dyes, Alexa dyes, Texas Red and the like as dyes for which fluorescent intensity is difficult to subject to the affection of a base sequence, (1) Experimental Method In the experiment, the effect of the quenching substance-labeled nucleic acid probe was evaluated by comparison of determining values of existing ratios of target genes in mimic samples. The determination of a existing ratio of target genes was carried out by making use of the calculating equation as described below.

Prior to the above experiment, a range of specific temperature was in advance determined; in the range, the doubly-labeled nucleic acid probe was capable of hybridizing enough to only a target gene and an internal standard gene, but of not hybridizing to the quenching substance-labeled nucleic acid probe. The temperature range was 52 to 57° C. in the former, and in the later not higher than 35° C. Based on the results, in ascertaining experiment, the temperature was changed to 95° C., 52° C., and 30° C. in this order and kept for one minute to an individual temperature. The object of keeping the temperature to 52° C. was to make the doubly-labeled nucleic acid probe hybridize to only a target gene and an internal standard gene. Subsequent to that, the keeping of 30° C. made the doubly-labeled nucleic acid hybridize to the quenching substance-labeled nucleic acid probe to cause the fluorescence for the doubly-labeled nucleic acid to be quenched.

<Calculating Equation>

This example illustrates a calculating method for determining a gene-constituent ratio quantitatively.

Signs usable in the calculating equation are below defined. A dye is defined as dye A, which dye causes a difference between the fluorescent intensity for the doubly-labeled probe on its hybridization to a target gene and the fluorescent intensity for the doubly-labeled probe on its hybridization to an internal standard gene; a dye is defined as dye B, which dye causes no difference.

y: a proportion of a hybridized probe;
1−y: a proportion of a non-hybridized probe;
x: a proportion of a target gene;
1−x: a proportion of an internal standard gene;
A: a ratio of the fluorescent intensity for dye A of the doubly-labeled nucleic acid probe on its 100%-hybridization with the quenching substance-labeled probe in use of a practical sample to the fluorescent intensity of dye A of the doubly-labeled nucleic probe on its 100%-hybridization with a quenching substance-labeled probe;
a: a ratio of the fluorescent intensity of dye A of the doubly-labeled nucleic acid probe on its 100%-hybridization with a target nucleic acid to the fluorescent intensity of dye A of the doubly-labeled nucleic acid probe on its 100%-hybridization with a quenching substance-labeled probe;
a': a ratio of the fluorescent intensity of dye A of the doubly-labeled nucleic acid probe on its 100%-hybridization with an internal standard nucleic acid to the fluorescent intensity of dye A of the doubly-labeled nucleic acid probe on its hybridization with a quenching substance-labeled probe;
B: a ratio of the fluorescent intensity of dye B of the doubly-labeled nucleic acid probe on its hybridization in use of a practical sample to the fluorescent intensity of dye B of the doubly-labeled nucleic probe on its 100%-hybridization with a quenching substance-labeled probe;

b: a ratio of the fluorescent intensity of dye B of the doubly-labeled nucleic acid probe on its 100%-hybridization with a target gene and an internal standard gene to the fluorescent intensity of dye B of the doubly-labeled nucleic acid probe on its 100%-hybridization with a quenching substance-labeled probe;

The fluorescent intensity proportion (A) of dye A in use of a practical sample is capable of being represented as follows:

$$A=(1-y)+axy+(1-x)a'y=1-y+axy+a'y-a'xy \quad (1)$$

If the equation (a) is deformed, a proportion (x) of a target gene is capable of being represented as follows:

$$x=(1-y-A+a'y)/(a'y-ay) \quad (2)$$

On the other hand, a fluorescent intensity (B) for dye B in use of a practical sample is capable of being represented.

$$B=by+1-y \quad (3)$$

If the equation (3) is deformed, a proportion (y) of a hybridized probe is capable of being represented as follows:

$$Y=(B-1)/(b-1) \quad (4)$$

The equation (2) is incorporated with the equation (4); the resultant equation is represented as follows:

$$x=(1-(B-1)/(b-1)-A+a'(B-1)/(b-1))/(a'(B-1)/(b-1)-a(B-1)/(b-1))=(b-B-Ab+A+a'B-a')/(a'B-a'-aB+a) \quad (5)$$

The items other than x are determined experimentally; a proportion of a target gene is thought to be capable of being calculated by an equation (5).

(2) Experimental Conditions
Target Gene and Internal Standard Gene
The same as in Example was used.
Total final concentration as combined of internal standard gene and target gene in a mimic sample: 20 nM, 40 nM, 80 nM (target:internal standard=4:1)
Base Sequence and Structure of Doubly-labeled Nucleic Acid Probe

```
BODIPY FL-5'ACTAC TGACT GACTG ACTGA CTGCT CC
3'-Cy5
```

Final concentration: 400 nM
Incidentally, those were like Example 6 except the 3'-end is labeled with Cy5.
Quenching Substance-labeled Probe:
DABCYL (Glean Research Inc., US) was used as a quenching substance. Base sequences are described as follows:
Quenching Substance-labeled Probe A:

```
5'GTCAG TCAGT AGTG3'-DABCYL
```

The 3'-end was labeled with DABCYL.
Quenching Substance-labeled Probe B:

```
DABCYL-5'GGGAG CAGTC AGTCA
```

The 5'-end was labeled with DABCYL.
(The underlined portions show the hybridization region of the doubly-labeled probe)
Synthesis of above oligonucleotides: by relying custom synthesis services (Espec oligoservices Inc.).

Final concentration of quenching substance-labeled probe: 800 nM
Fluorescence for Cy5 was measured by an exciting wavelength: 600 nm and measuring wavelength: 670 nm.
Other conditions (used buffer, used apparatus, used instrument, and the like) were like those of Example 9.

(3) Results and Discussion
The below table shows the results of quantitation of a constituent ratio of genes. In this system also, a ratio of fluorescent intensity (A and B) for BODIPY FL in the mimic samples was reduced with reducing amount of total genes. However, in the case of the amount of a total sum of genes of the smallest 20 nM also, the determining values of the gene constituent ratio in the mimic samples were almost close to the theoretical value. From the above results, it has become apparent that a gene-constituent ratio can be accurately determined quantitatively by addition of a quenching substance-labeled probe to reduce fluorescence for the non-hybridized probe, and, as a result, a target gene can be accurately determined quantitatively. In addition, the calculation method as described in this Example also was apparently useful for determining a gene-constituent ratio quantitatively.

Likewise in Example 9, the quenching substance-labeled probe makes fluorescence for the non-hybridized probe reduce; thereby, the probe makes it possible to determine accurately fluorescence derived from the hybridization of the probe with a target gene and an internal standard gene. On the basis of the above reason, the quenching substance-labeled probe is advantageous for all target nucleic acid probes (including an internal standard nucleic acid probe and a doubly-labeled nucleic acid probe) and all assaying methods making use thereof as described in this application.

Additionally, in the case of targeted amplification products amplified by any gene-amplification method also, the quenching substance-labeled probe is profitable based on the same reason as the above one.

TABLE 9

Result of quantitation of gene-constituent ratio

|  | BODIPY Relative fluorescent intensity | Cy5 Relative fluorescent intensity | Quantitative value (target/ internal standard) | Theoritical value (target/ internal standard) |
|---|---|---|---|---|
| Non-hybridizing probe | 1.00 | 1.00 | — | — |
| 100% target gene (BODIPY: a, Cy5: b) | 2.33 | 12.50 | — | — |
| 100% internal standard gene (BODIPY: a', Cy5: b) | 11.11 |  | — | — |
| Mimic Sample 1 Total amount of gene: 80 nM (BODIPY: A, Cy5: B) | 1.59 | 3.23 | 4.22 | 4.00 |
| Mimic Sample 2 Total amount of gene: 40 nM (BODIPY: A, Cy5: B) | 1.31 | 2.13 | 3.84 |  |
| Mimic Sample 3 Total amount of gene: 20 nM (BODIPY: A, Cy5: B) | 1.14 | 1.51 | 3.68 |  |

INDUSTRIAL APPLICABILITY

A novel mixture according to the present invention is capable of provide a method for assaying a nucleic acid, the method producing advantageous effects as described in the above description. The present invention, therefore, can greatly contribute to genetic engineering, medicals, medical arts, agricultural techniques, development of various biological techniques, development of complex microbes usable in wastes-treatment plants and the like.

The invention claimed is:

1. A method for assaying a target nucleic acid in a sample, which comprises:
   (I) adding (i) a fluorescence-quenching probe to the sample, wherein the fluorescence-quenching probe (i) has, as one of end bases thereof, a cytosine which is labeled with a first fluorescence-quenching dye, and the fluorescence-quenching probe (i) is hybridizable with the target nucleic acid and is designed such that at least one guanine exists in the target nucleic acid at a position of from a 1st base to a 3rd base, with the proviso that a base, which is base-paired with the cytosine, is counted as the 1st base, and
   wherein the first fluorescence-quenching dye is selected from the group consisting of 2',4,7,7'-tetra-chlorofluorescein, TBSF, 2',4,4',5',7,7'-hexachlorofluorescein, R6G and 2-oxo-6,8-difluoro-7-hydroxy-2H-1-benzopyran-3-carboxylic acid,
   (II) maintaining the sample under conditions that the fluorescence-quenching probe (i) is hybridizable with the target nucleic acid, and measuring fluorescence derived from the fluorescence-quenching probe (i),
   (III) maintaining the sample under conditions that the fluorescence-quenching probe (i) is not hybridizable with the target nucleic acid, and measuring fluorescence derived from the fluorescence-quenching probe (i), and
   (IV) assaying the target nucleic acid in the sample from fluorescent intensities determined in the step (II) and step (III),
   wherein the fluorescence-quenching probe (i) have cytosines as both the end bases, and the end base different from the one end base is labeled with a second fluorescence-quenching dye different from the first fluorescence-quenching dye.

2. The method according to claim 1, wherein the step (II) to step (IV) are conducted by a real-time monitoring, quantitative PCR method.

3. The method according to claim 1, wherein the second fluorescence-quenching dye is selected from the group consisting of 2',4,7,7'-tetra-chlorofluorescein, TBSF, 2',4,4',5',7,7'-hexachlorofluorescein, R6G, 2-oxo-6,8-difluoro-7-hydroxy-2H-1-benzopyran-3-carboxylic acid, 4,4-difluoro-5,7-dimethyl-4-bora-3a,4a-diaza-s-indacene-3-propionic acid and Carboxytetramethylrhodamine.

4. The method according to claim 1, wherein the target nucleic acid is a gene amplification product.

5. The method according to claim 1, wherein the target nucleic acid is a gene amplification product amplified by a method selected from a PCR method, LCR method, TAS method, ICAN method, LAMP method, NASBA method, RCA method, TAMA method and UCAN method.

6. A method for assaying, at the same time, a first and second target nucleic acid in a sample, which comprises:
   (I) adding (i) a first fluorescence-quenching probe and (ii) a second fluorescence-quenching probe to the sample, wherein the first fluorescence-quenching probe (i) has, as one of end bases thereof, a cytosine which is labeled with a first fluorescence-quenching dye, and the first fluorescence-quenching probe (i) is hybridizable with the first target nucleic acid and is designed such that a guanine exists in the first target nucleic acid at a position that is base-paired with the cytosine,
   wherein the second fluorescence-quenching probe (ii) has, as one of end bases thereof, a cytosine which is labeled with a second fluorescence-quenching dye different from the first fluorescence-quenching dye, and the second fluorescence-quenching probe (ii) is hybridizable with the second target nucleic acid and is designed such that a guanine exists in the second target nucleic acid that is base-paired with the cytosine, and
   wherein the first fluorescence-quenching dye is selected from the group consisting of 2-oxo-6,8-difluoro-7-hydroxy-2H-1-benzopyran-3-carboxylic acid,
   (II) maintaining the sample under conditions that the first and second fluorescence-quenching probes (i) and (ii) are hybridizable with the first and second target nucleic acids, respectively, and measuring fluorescence derived from the first fluorescence-quenching probe (i) and fluorescence derived from the second fluorescence-quenching probe (ii),
   (III) maintaining the sample under conditions that the first and second fluorescence-quenching probes (i) and (ii) are not hybridizable with the first and second target nucleic acids, respectively, and measuring fluorescence derived from the first fluorescence-quenching probe (i) and fluorescence derived from the second fluorescence-quenching probe (ii), and
   (IV) assaying the first and second target nucleic acids in the sample from fluorescent intensities determined in the step (II) and step (III).

7. The method according to claim 6, wherein the second fluorescence-quenching dye with which the second fluorescence-quenching probe (ii) is labeled is selected from the group consisting of 2',4,7,7'-tetra-chlorofluorescein, TBSF, 2',4,4',5',7,7'-hexachlorofluorescein, R6G, 4,4-difluoro-5,7-dimethyl-4-bora-3a,4a-diaza-s-indacene-3-propionic acid and Carboxytetramethylrhodamine.

8. The method according to claim 6, wherein the first and second target nucleic acids are gene amplification products, respectively.

9. The method according to claim 6, wherein the first and second target nucleic acids are gene amplification products, respectively, which have been amplified by a method selected from a PCR method, LCR method, TAS method, ICAN method, LAMP method, NASBA method, RCA method, TAMA method and UCAN method.

10. A method for assaying a target nucleic acid in a sample, which comprises:
   (I) adding (i) a fluorescence-quenching probe to the sample, wherein the fluorescence-quenching probe (i) has, as one of end bases thereof, a cytosine which is labeled with a first fluorescence-quenching dye, and the fluorescence-quenching probe (i) is hybridizable with the target nucleic acid and is designed such that a guanine exists in the target nucleic acid at a position that is base-paired with the cytosine, and
   wherein the first fluorescence-quenching dye is 2-oxo-6,8-difluoro-7-hydroxy-2H-1-benzopyran-3-carboxylic acid,
   (II) maintaining the sample under conditions that the fluorescence-quenching probe (i) is hybridizable with the target nucleic acid, and measuring fluorescence derived from the fluorescence-quenching probe (i),
   (III) maintaining the sample under conditions that the fluorescence-quenching probe (i) is not hybridizable with the target nucleic acid, and measuring fluorescence derived from the fluorescence-quenching probe (i), and
   (IV) assaying the target nucleic acid in the sample from fluorescent intensities determined in the step (II) and step (III).

11. The method according to claim 10, wherein the step (II) to step (IV) are conducted by a real-time monitoring, quantitative PCR method.

12. The method according to claim 10, wherein the fluorescence-quenching probe (i) have cytosines as both the end bases, and the end base different from the one end base is labeled with a second fluorescence-quenching dye different from the first fluorescence-quenching dye.

13. The method according to claim 12, wherein the second fluorescence-quenching dye is selected from the group consisting of 2',4,7,7'-tetra-chlorofluorescein, TBSF, 2',4,4',5',7,7'-hexachlorofluorescein, R6G, 4,4-difluoro-5,7-dimethyl-4-bora-3a,4a-diaza-s-indacene-3-propionic acid and Carboxytetramethylrhodamine.

14. The method according to claim 10, wherein the target nucleic acid is a gene amplification product.

15. The method according to claim 10, wherein the target nucleic acid is a gene amplification product amplified by a method selected from a PCR method, LCR method, TAS method, ICAN method, LAMP method, NASBA method, RCA method, TAMA method and UCAN method.

* * * * *

```
                          SEQUENCE LISTING

<160> NUMBER OF SEQ ID NOS: 34

<210> SEQ ID NO 1
<211> LENGTH: 22
<212> TYPE: DNA
<213> ORGANISM: Artificial Sequence
<220> FEATURE:
<223> OTHER INFORMATION: Synthetic DNA

<400> SEQUENCE: 1
agttccggaa aggccagagg ag                                              22

<210> SEQ ID NO 2
<211> LENGTH: 22
<212> TYPE: DNA
<213> ORGANISM: Artificial Sequence
<220> FEATURE:
<223> OTHER INFORMATION: Synthetic DNA

<400> SEQUENCE: 2
ggttccggaa aggccagagg aa                                              22

<210> SEQ ID NO 3
<211> LENGTH: 22
<212> TYPE: DNA
<213> ORGANISM: Artificial Sequence
<220> FEATURE:
<223> OTHER INFORMATION: Synthetic DNA

<400> SEQUENCE: 3
ctcctctggc ctttccggaa cc                                              22

<210> SEQ ID NO 4
<211> LENGTH: 18
<212> TYPE: DNA
<213> ORGANISM: Artificial Sequence
<220> FEATURE:
<223> OTHER INFORMATION: Synthetic DNA

<400> SEQUENCE: 4
aaaaaagggg gggggggg                                                   18

<210> SEQ ID NO 5
<211> LENGTH: 18
<212> TYPE: DNA
<213> ORGANISM: Artificial Sequence
<220> FEATURE:
<223> OTHER INFORMATION: Synthetic DNA

<400> SEQUENCE: 5
cccccccccc ccttttttt                                                  18

<210> SEQ ID NO 6
<211> LENGTH: 33
<212> TYPE: DNA
<213> ORGANISM: Artificial Sequence
<220> FEATURE:
<223> OTHER INFORMATION: Synthetic DNA

<400> SEQUENCE: 6
tttggatgac tgactgactg actgacgaga ttt                                  33
```

<210> SEQ ID NO 7
<211> LENGTH: 33
<212> TYPE: DNA
<213> ORGANISM: Artificial Sequence
<220> FEATURE:
<223> OTHER INFORMATION: Synthetic DNA

<400> SEQUENCE: 7
tttagatgac tgactgactg actgacgagg ttt                                    33

<210> SEQ ID NO 8
<211> LENGTH: 27
<212> TYPE: DNA
<213> ORGANISM: Artificial Sequence
<220> FEATURE:
<223> OTHER INFORMATION: Synthetic DNA

<400> SEQUENCE: 8
cctactgact gactgactga ctgctcc                                           27

<210> SEQ ID NO 9
<211> LENGTH: 27
<212> TYPE: DNA
<213> ORGANISM: Artificial Sequence
<220> FEATURE:
<223> OTHER INFORMATION: Synthetic DNA

<400> SEQUENCE: 9
cctactgact gactgactga ctgctcc                                           27

<210> SEQ ID NO 10
<211> LENGTH: 27
<212> TYPE: DNA
<213> ORGANISM: Artificial Sequence
<220> FEATURE:
<223> OTHER INFORMATION: Synthetic DNA

<400> SEQUENCE: 10
cctactgact gactgactga ctgctcc                                           27

<210> SEQ ID NO 11
<211> LENGTH: 22
<212> TYPE: DNA
<213> ORGANISM: Artificial Sequence
<220> FEATURE:
<223> OTHER INFORMATION: Synthetic DNA

<400> SEQUENCE: 11
agttccggaa aggccagagg ag                                                22

<210> SEQ ID NO 12
<211> LENGTH: 22
<212> TYPE: DNA
<213> ORGANISM: Artificial Sequence
<220> FEATURE:
<223> OTHER INFORMATION: Synthetic DNA

<400> SEQUENCE: 12
ggttccggaa aggccagagg aa                                                22

<210> SEQ ID NO 13
<211> LENGTH: 22
<212> TYPE: DNA
<213> ORGANISM: Artificial Sequence
<220> FEATURE:
<223> OTHER INFORMATION: Synthetic DNA

<400> SEQUENCE: 13
ctcctctggc ctttccggaa cc                                              22

<210> SEQ ID NO 14
<211> LENGTH: 24
<212> TYPE: DNA
<213> ORGANISM: Artificial Sequence
<220> FEATURE:
<223> OTHER INFORMATION: Synthetic DNA

<400> SEQUENCE: 14
cctttaggat ttcagcatca gtgg                                            24

<210> SEQ ID NO 15
<211> LENGTH: 18
<212> TYPE: DNA
<213> ORGANISM: Artificial Sequence
<220> FEATURE:
<223> OTHER INFORMATION: Synthetic DNA

<400> SEQUENCE: 15
gacttgtcgc cgggaatg                                                   18

<210> SEQ ID NO 16
<211> LENGTH: 22
<212> TYPE: DNA
<213> ORGANISM: Artificial Sequence
<220> FEATURE:
<223> OTHER INFORMATION: Synthetic DNA

<400> SEQUENCE: 16
agttccggaa aggccagagg ag                                              22

<210> SEQ ID NO 17
<211> LENGTH: 22
<212> TYPE: DNA
<213> ORGANISM: Artificial Sequence
<220> FEATURE:
<223> OTHER INFORMATION: Synthetic DNA

<400> SEQUENCE: 17
ggttccggaa aggccagagg aa                                              22

<210> SEQ ID NO 18
<211> LENGTH: 22
<212> TYPE: DNA
<213> ORGANISM: Artificial Sequence
<220> FEATURE:
<223> OTHER INFORMATION: Synthetic DNA

<400> SEQUENCE: 18
ctcctctggc ctttccggaa cc                                              22

<210> SEQ ID NO 19
<211> LENGTH: 32
<212> TYPE: DNA
<213> ORGANISM: Artificial Sequence
<220> FEATURE:
<223> OTHER INFORMATION: Synthetic DNA

<400> SEQUENCE: 19
taatgatgac tgactgactg actgacgatg gt                                   32

<210> SEQ ID NO 20

<211> LENGTH: 32
<212> TYPE: DNA
<213> ORGANISM: Artificial Sequence
<220> FEATURE:
<223> OTHER INFORMATION: Synthetic DNA

<400> SEQUENCE: 20
tggtatgact gactgactga ctgacgagta at                          32

<210> SEQ ID NO 21
<211> LENGTH: 27
<212> TYPE: DNA
<213> ORGANISM: Artificial Sequence
<220> FEATURE:
<223> OTHER INFORMATION: Synthetic DNA

<400> SEQUENCE: 21
actactgact gactgactga ctgctca                                27

<210> SEQ ID NO 22
<211> LENGTH: 32
<212> TYPE: DNA
<213> ORGANISM: Artificial Sequence
<220> FEATURE:
<223> OTHER INFORMATION: Synthetic DNA

<400> SEQUENCE: 22
taaggatgac tgactgactg actgacgatg gt                          32

<210> SEQ ID NO 23
<211> LENGTH: 32
<212> TYPE: DNA
<213> ORGANISM: Artificial Sequence
<220> FEATURE:
<223> OTHER INFORMATION: Synthetic DNA

<400> SEQUENCE: 23
taagatgact gactgactga ctgacgagta at                          32

<210> SEQ ID NO 24
<211> LENGTH: 27
<212> TYPE: DNA
<213> ORGANISM: Artificial Sequence
<220> FEATURE:
<223> OTHER INFORMATION: Synthetic DNA

<400> SEQUENCE: 24
actactgact gactgactga ctgctcc                                27

<210> SEQ ID NO 25
<211> LENGTH: 33
<212> TYPE: DNA
<213> ORGANISM: Artificial Sequence
<220> FEATURE:
<223> OTHER INFORMATION: Synthetic DNA

<400> SEQUENCE: 25
aattcgtacc aactatcctc gtcgtcagct atg                         33

<210> SEQ ID NO 26
<211> LENGTH: 33
<212> TYPE: DNA
<213> ORGANISM: Artificial Sequence
<220> FEATURE:
<223> OTHER INFORMATION: Synthetic DNA

<400> SEQUENCE: 26
gattcgtacc aactatcctc gtcgtcagct ata                                         33

<210> SEQ ID NO 27
<211> LENGTH: 33
<212> TYPE: DNA
<213> ORGANISM: Artificial Sequence
<220> FEATURE:
<223> OTHER INFORMATION: Synthetic DNA

<400> SEQUENCE: 27
catagctgac gacgaggata gttggtacga atc                                         33

<210> SEQ ID NO 28
<211> LENGTH: 17
<212> TYPE: DNA
<213> ORGANISM: Artificial Sequence
<220> FEATURE:
<223> OTHER INFORMATION: Synthetic DNA

<400> SEQUENCE: 28
ctcgtcgtca gctatgg                                                           17

<210> SEQ ID NO 29
<211> LENGTH: 18
<212> TYPE: DNA
<213> ORGANISM: Artificial Sequence
<220> FEATURE:
<223> OTHER INFORMATION: Synthetic DNA

<400> SEQUENCE: 29
ggattcgtac caactatc                                                          18

<210> SEQ ID NO 30
<211> LENGTH: 22
<212> TYPE: DNA
<213> ORGANISM: Artificial Sequence
<220> FEATURE:
<223> OTHER INFORMATION: Synthetic DNA

<400> SEQUENCE: 30
ttgtccggaa aggccagagg ag                                                     22

<210> SEQ ID NO 31
<211> LENGTH: 22
<212> TYPE: DNA
<213> ORGANISM: Artificial Sequence
<220> FEATURE:
<223> OTHER INFORMATION: Synthetic DNA

<400> SEQUENCE: 31
atgtccggaa aggccagagg ag                                                     22

<210> SEQ ID NO 32
<211> LENGTH: 22
<212> TYPE: DNA
<213> ORGANISM: Artificial Sequence
<220> FEATURE:
<223> OTHER INFORMATION: Synthetic DNA

<400> SEQUENCE: 32
ctcctctggc ctttccggac at                                                     22

<210> SEQ ID NO 33
<211> LENGTH: 14
<212> TYPE: DNA

```
<213> ORGANISM: Artificial Sequence
<220> FEATURE:
<223> OTHER INFORMATION: Synthetic DNA

<400> SEQUENCE: 33
gtcagtcagt actg                                                    14

<210> SEQ ID NO 34
<211> LENGTH: 15
<212> TYPE: DNA
<213> ORGANISM: Artificial Sequence
<220> FEATURE:
<223> OTHER INFORMATION: Synthetic DNA

<400> SEQUENCE: 34
ggaacgagtc agtca                                                   15
```